(12) United States Patent
Balin et al.

(10) Patent No.: US 11,096,965 B2
(45) Date of Patent: Aug. 24, 2021

(54) COMPOSITIONS AND METHODS RELATED TO POLYCYTOTOXIC T CELLS

(71) Applicants: The Regents of the University of California, Oakland, CA (US); ULM UNIVERSITY, Ulm (DE)

(72) Inventors: Samuel J. Balin, Playa Del Rey, CA (US); Robert L. Modlin, Sherman Oaks, CA (US); Steffen Stenger, Ulm (DE); Matteo Pellegrini, Sherman Oaks, CA (US)

(73) Assignees: The Regents of the University of California, Oakland, CA (US); ULM UNIVERSITY, Ulm (DE)

( * ) Notice: Subject to any disclaimer, the term of this patent is extended or adjusted under 35 U.S.C. 154(b) by 149 days.

(21) Appl. No.: 16/091,029

(22) PCT Filed: Apr. 4, 2017

(86) PCT No.: PCT/US2017/025842
§ 371 (c)(1),
(2) Date: Oct. 3, 2018

(87) PCT Pub. No.: WO2017/176672
PCT Pub. Date: Oct. 12, 2017

(65) Prior Publication Data
US 2019/0117689 A1      Apr. 25, 2019

Related U.S. Application Data

(60) Provisional application No. 62/317,941, filed on Apr. 4, 2016.

(51) Int. Cl.
| | |
|---|---|
| *A61K 35/17* | (2015.01) |
| *G01N 33/569* | (2006.01) |
| *G01N 33/50* | (2006.01) |
| *C12N 5/0783* | (2010.01) |
| *A61K 38/20* | (2006.01) |
| *C12Q 1/6883* | (2018.01) |
| *C12Q 1/6886* | (2018.01) |
| *A61K 45/06* | (2006.01) |
| *C07K 16/28* | (2006.01) |
| *C12Q 1/6888* | (2018.01) |
| *G01N 15/06* | (2006.01) |
| *G01N 15/00* | (2006.01) |

(52) U.S. Cl.
CPC .............. *A61K 35/17* (2013.01); *A61K 38/20* (2013.01); *A61K 38/2013* (2013.01); *A61K 38/2046* (2013.01); *A61K 38/2086* (2013.01); *A61K 45/06* (2013.01); *C07K 16/2866* (2013.01); *C12N 5/0638* (2013.01); *C12Q 1/6883* (2013.01); *C12Q 1/6886* (2013.01); *C12Q 1/6888* (2013.01); *G01N 15/0656* (2013.01); *G01N 33/505* (2013.01); *G01N 33/56972* (2013.01); *C12Q 2600/158* (2013.01); *G01N 2015/008* (2013.01); *G01N 2015/0693* (2013.01); *G01N 2800/24* (2013.01)

(58) Field of Classification Search
None
See application file for complete search history.

(56) References Cited

FOREIGN PATENT DOCUMENTS

| | | | |
|---|---|---|---|
| EP | 2982746 A1 * | 2/2016 | ........... C12N 5/0637 |
| WO | WO-2007/071388 A1 | 6/2007 | |
| WO | WO-2009/149539 A1 | 12/2009 | |
| WO | WO-2012/160448 A2 | 11/2012 | |
| WO | WO-2013/017653 A1 | 2/2013 | |
| WO | WO-2014/066527 A2 | 5/2014 | |

OTHER PUBLICATIONS

Busch et al., "Lipoarabinomannan-Responsive Polycytotoxic T Cells are Associated with Protection in Human Tuberculosis," American Journal of Respiratory and Critical Care Medicine, 194(3):345-355 (2016).
Extended European Search Report for EP Application No. 17779615.8 dated Apr. 28, 2020.
Novais et al., "Cytotoxic T Cells Mediate Pathology and Metastasis in Cutaneous Leishmaniasis," PLoS Pathogens, 9(7):e1003504 (2013).
Balin et al., "010 Polycytotoxic T cells protect against intracellular infection," J Invest Dermatol, 136(5): Supplement 1, p. S2 (2016).
International Search Report and Written Opinion for International Application No. PCT/US2017/025842 dated Jul. 12, 2017.
Novais et al., "Cytotoxic T cells mediate pathology and metastasis in cutaneous leishmaniasis," PLoS Pathog, 9(7): e1003504 (2013).
Rosenthal et al., "Differential responsiveness to IL-2, IL-7, and IL-15 common receptor gamma chain cytokines by antigen-specific peripheral blood naive or memory cytotoxic CD8+ T cells from healthy donors and melanoma patients," J Immunother, 32(3): 252-261 (2009).
Sarwal et al., "Granulysin expression is a marker for acute rejection and steroid resistance in human renal transplantation," Hum Immunol, 62(1): 21-31 (2001).
Umemura et al., "Overexpression of IL-15 in vivo enhances protection against Mycobacterium bovis bacillus Calmette-Guérin infection via augmentation of NK and T cytotoxic 1 responses," J Immunol, 167(2): 946-956 (2001).
Yap et al., "Expansion of highly differentiated cytotoxic terminally differentiated effector memory CD8+ T cells in a subset of clinically stable kidney transplant recipients: a potential marker for late graft dysfunction," J Am Soc Nephrol, 25(8): 1856-1868 (2014).

* cited by examiner

*Primary Examiner* — Daniel C Gamett
(74) *Attorney, Agent, or Firm* — Foley Hoag LLP

(57) ABSTRACT

Various aspects of the invention relate to compositions comprising polycytotoxic T cells. Some aspects relate to methods for obtaining a composition comprising polycytotoxic T cells. Some aspects relate to methods of administering a composition comprising polycytotoxic T cells to a subject. Some aspects relate to methods for monitoring an immune response in a subject, comprising determining the concentration of polycytotoxic T cells in the blood of the subject. Some aspects relate to methods for treating a condition or disease in a subject, comprising administering to the subject a composition comprising an antibody, or an antigen-binding portion thereof, that specifically binds to a protein expressed by a polycytotoxic T cell.

20 Claims, 23 Drawing Sheets

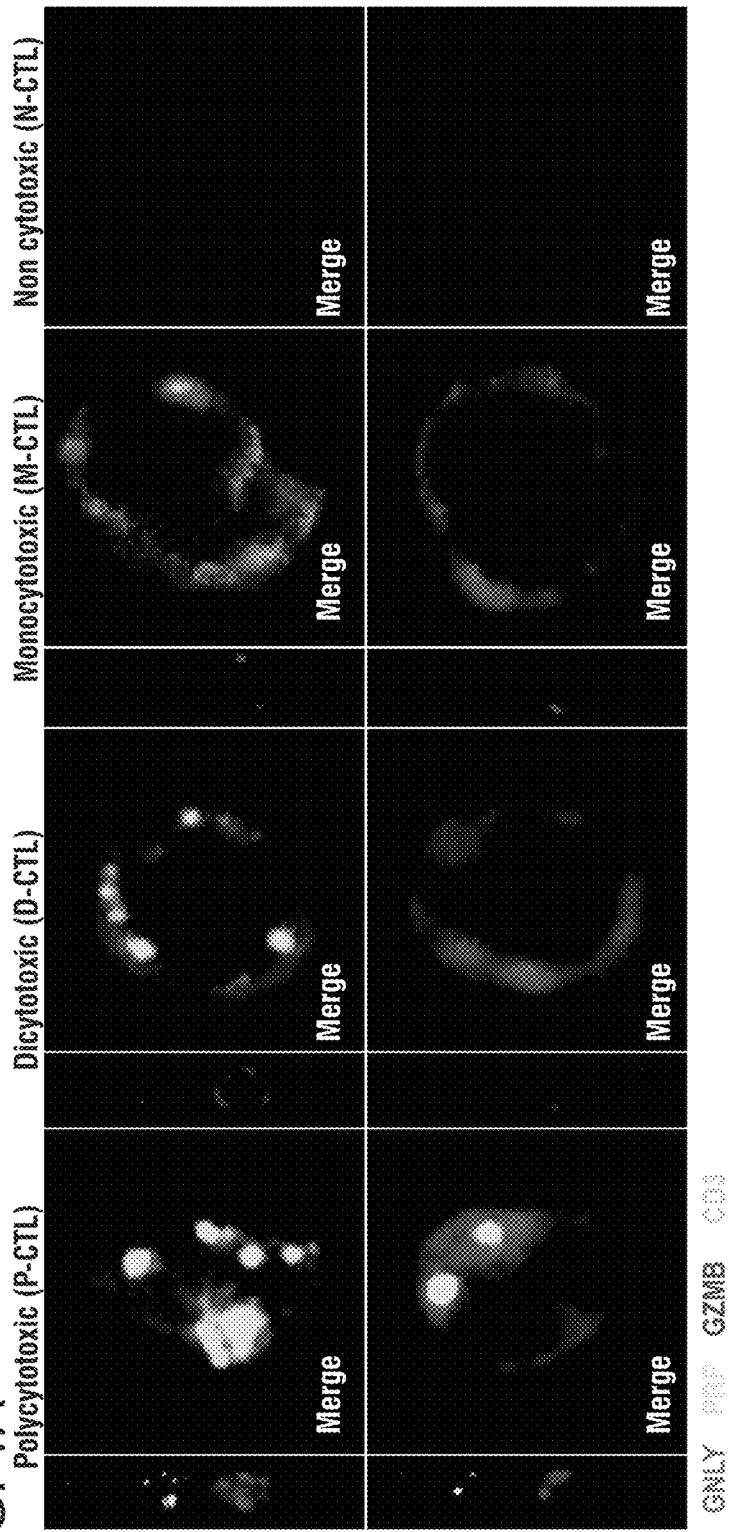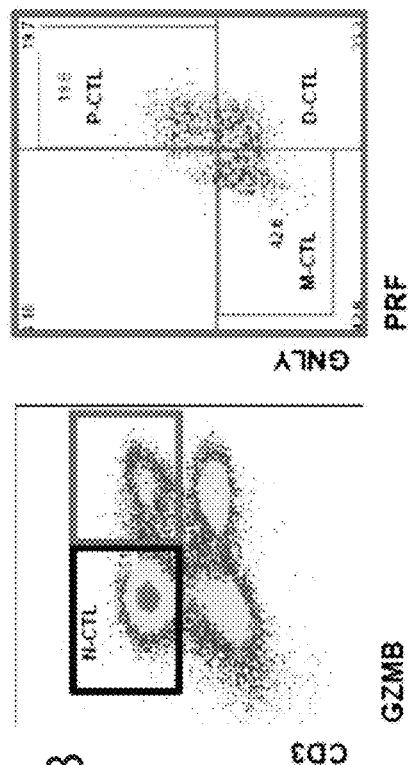

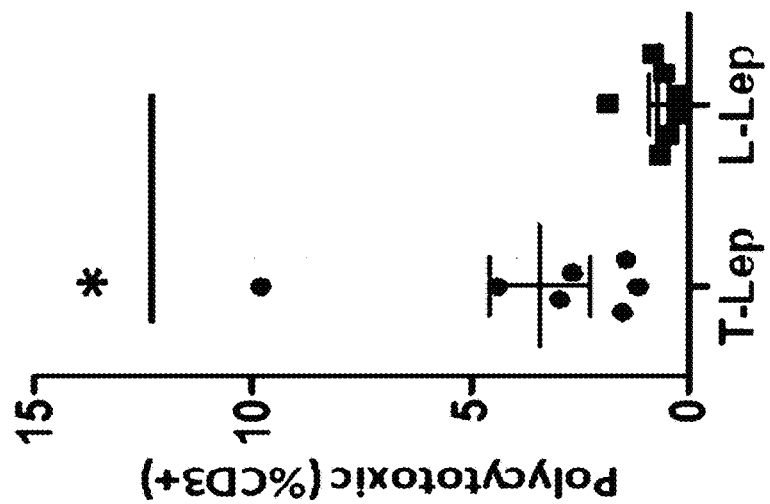
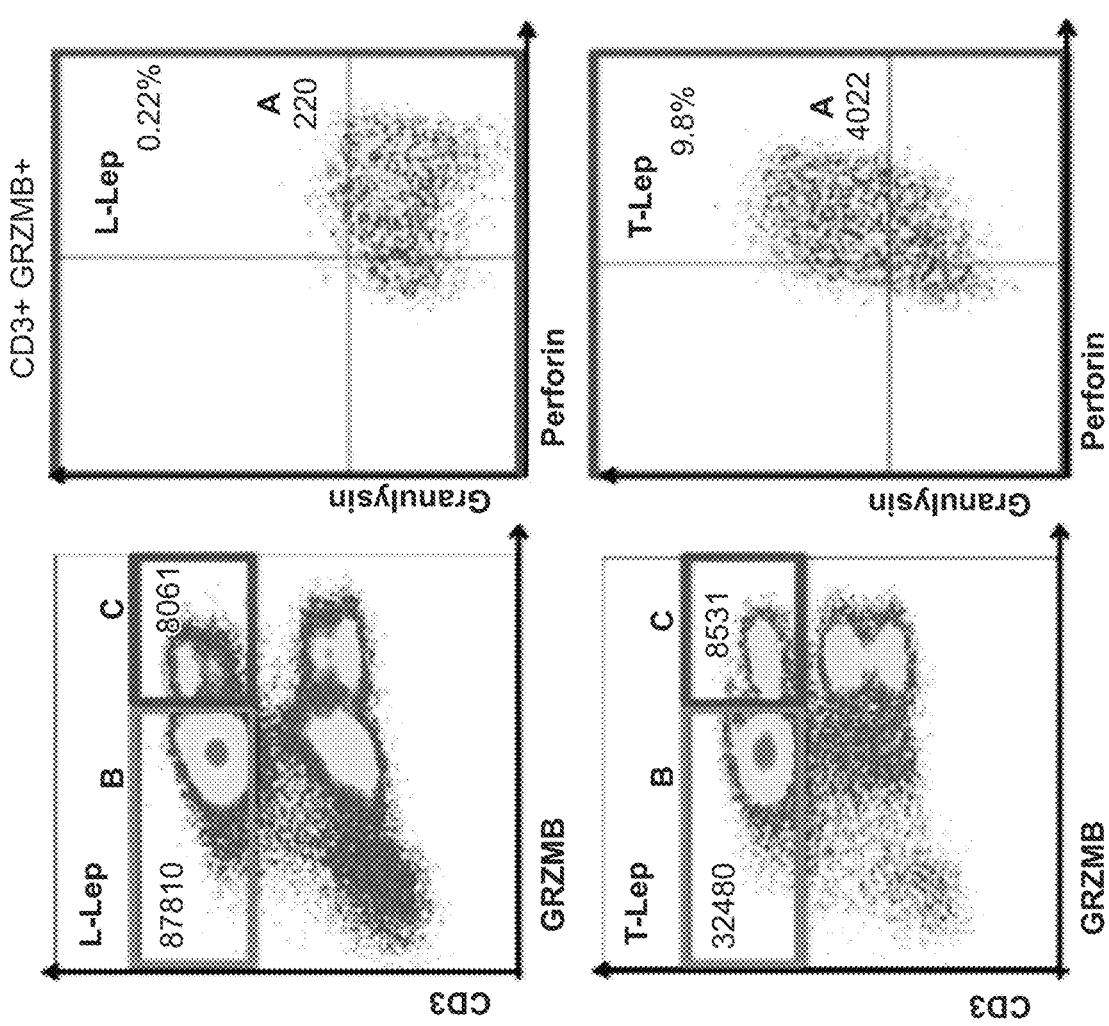

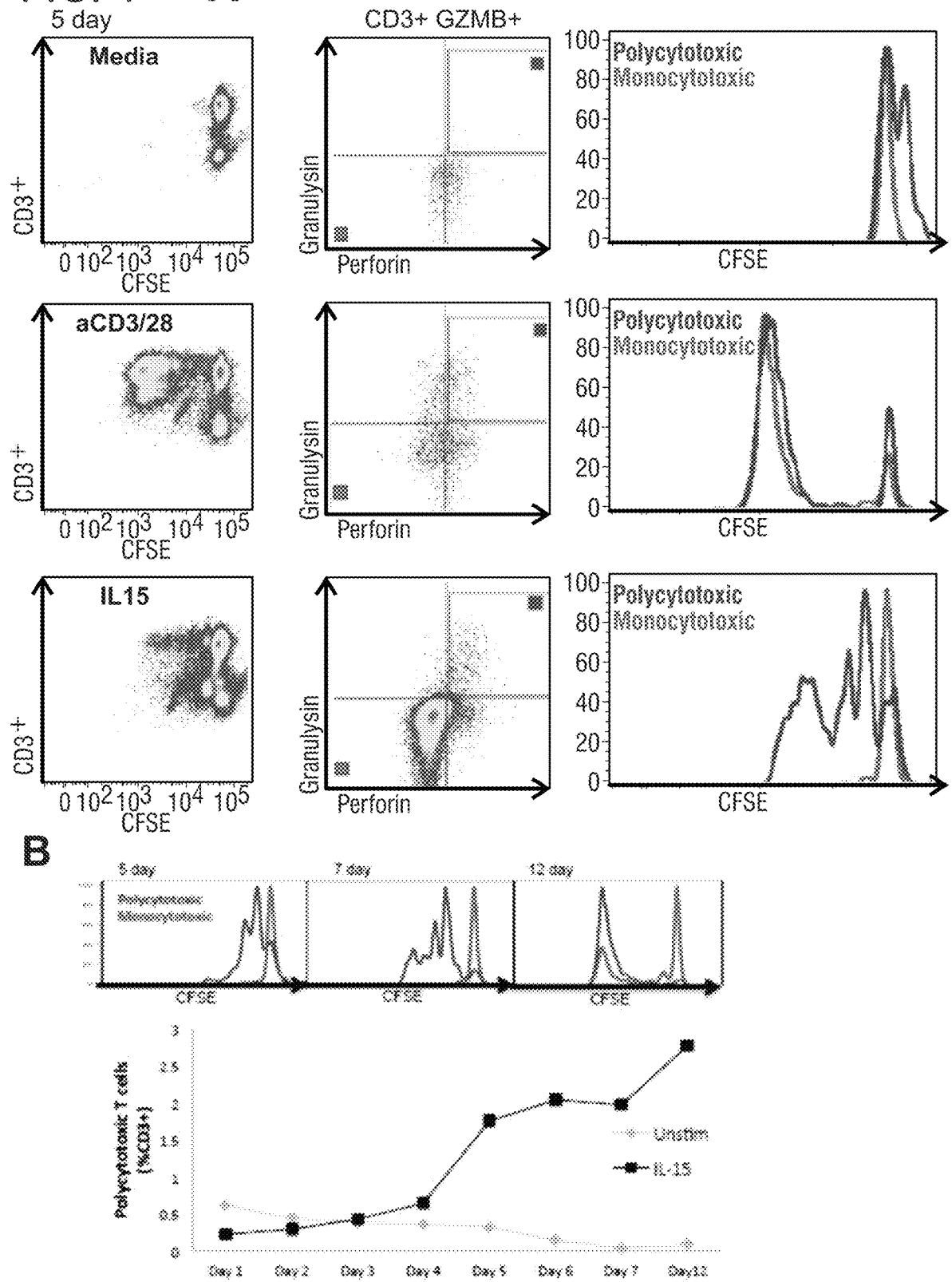

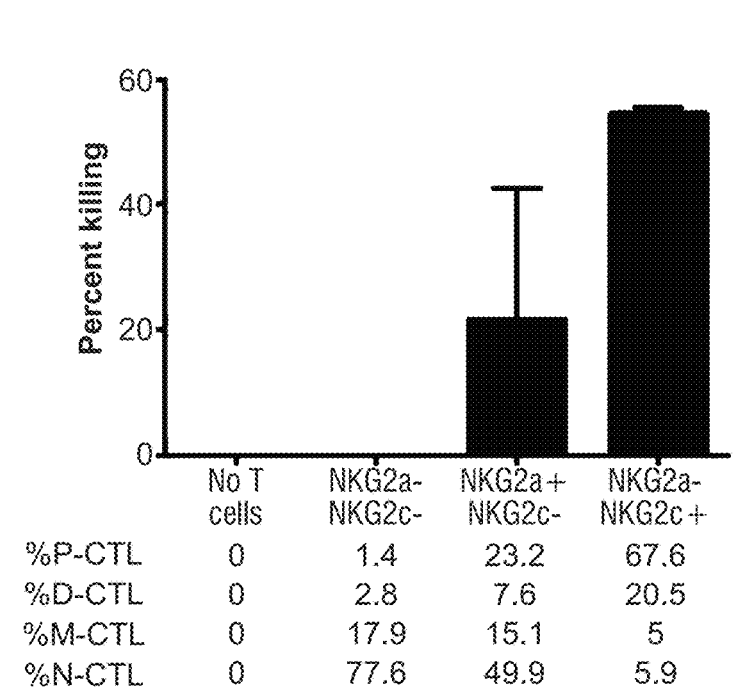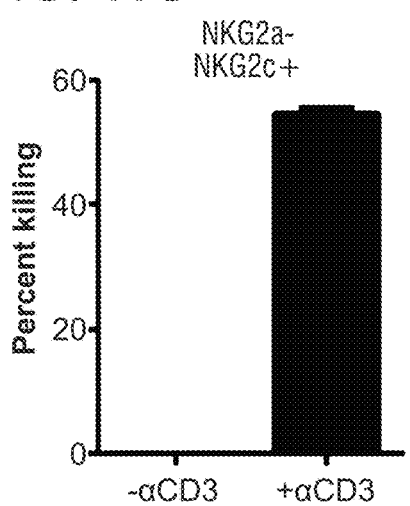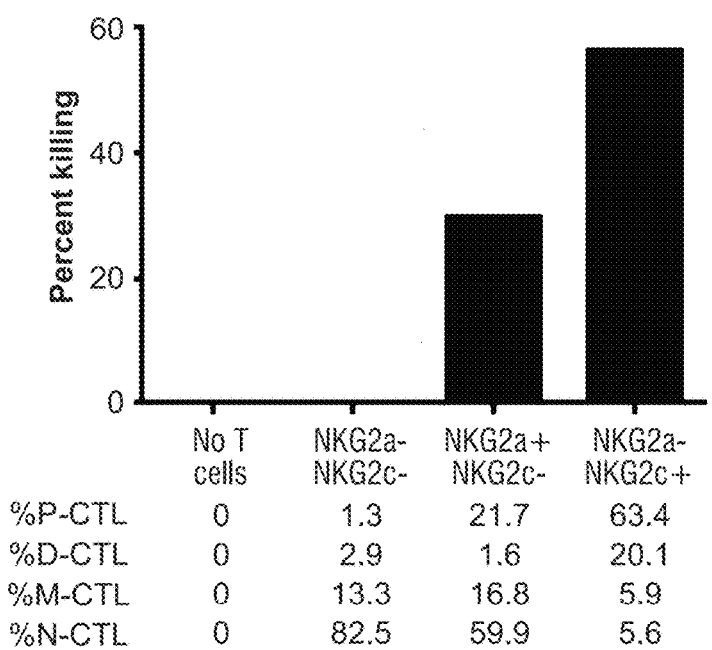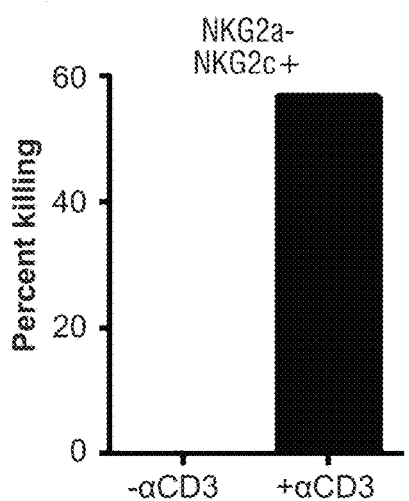
FIG. 11A
FIG. 11B
FIG. 11C
FIG. 11D

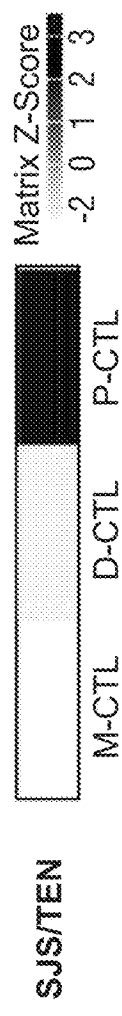
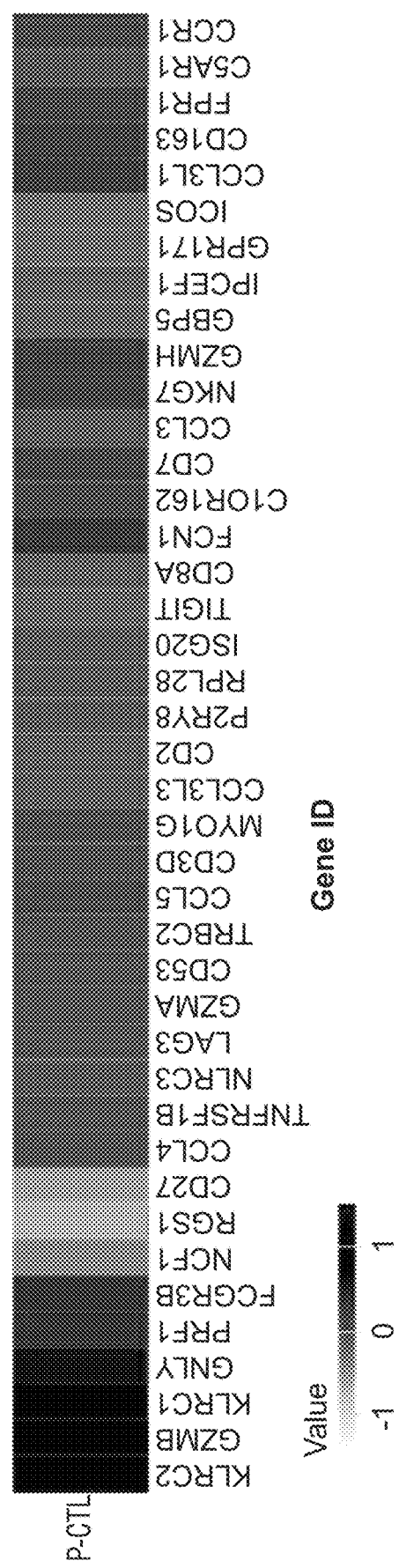
FIG. 12A
FIG. 12B

FIG. 16
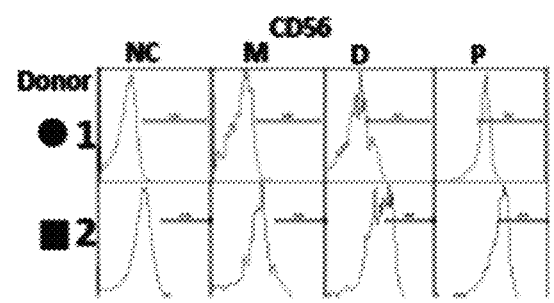
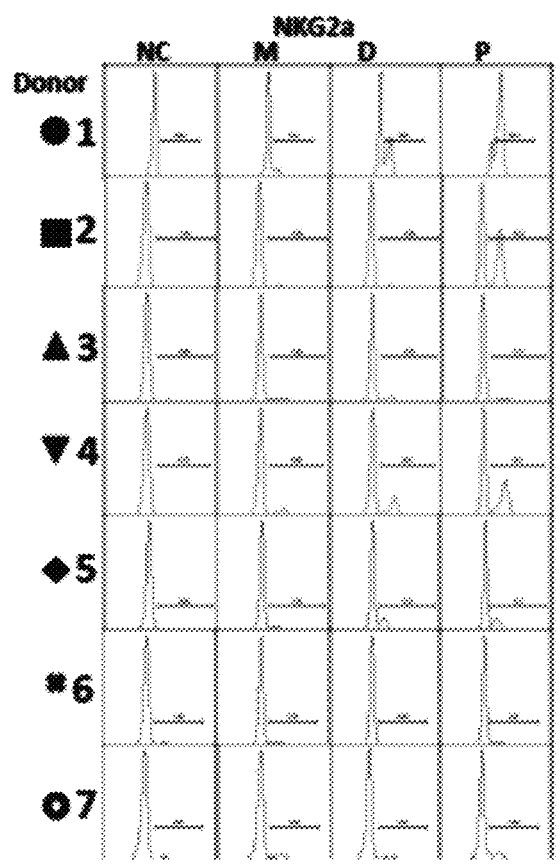
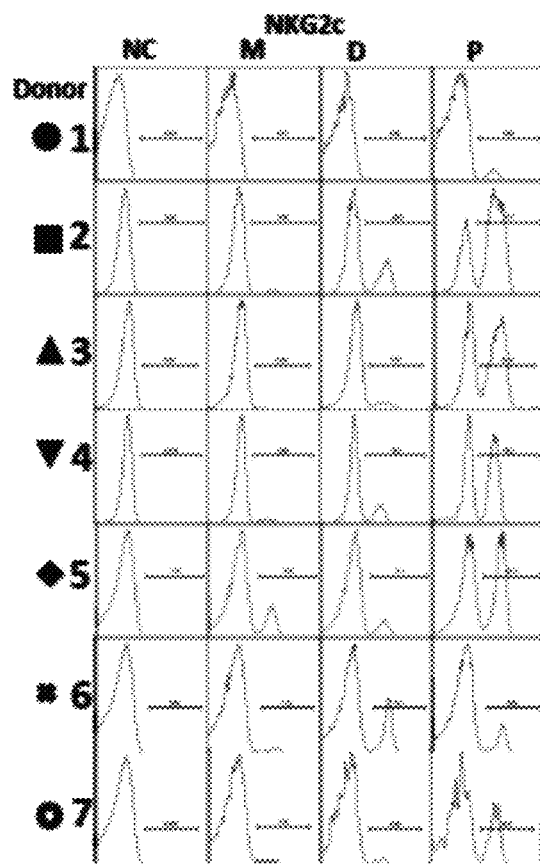

Figure 18

Top Canonical Pathways→Donor-1:-Polycytotoxic-Signature¶

| Name | p-value | Overlap |
|---|---|---|
| Natural Killer Cell Signaling | 1.12E-13 | 29.1% 32/110 |
| Crosstalk between Dendritic Cells and Natural Killer Cells | 3.08E-12 | 30.3% 27/89 |
| Germ Cell-Sertoli Cell Junction Signaling | 2.80E-10 | 21.2% 34/160 |
| Integrin Signaling | 9.08E-10 | 18.9% 38/201 |
| Antigen Presentation Pathway | 2.22E-09 | 40.5% 15/37 |

Top Canonical Pathways→Donor-2:-Polycytotoxic-Signature¶

| Name | p-value | Overlap |
|---|---|---|
| Natural Killer Cell Signaling | 5.81E-16 | 29.1% 32/110 |
| Crosstalk between Dendritic Cells and Natural Killer Cells | 2.32E-08 | 22.5% 20/89 |
| Integrin Signaling | 5.04E-08 | 15.4% 31/201 |
| Germ Cell-Sertoli Cell Junction Signaling | 6.05E-08 | 16.9% 27/160 |
| T Helper Cell Differentiation | 5.60E-07 | 22.5% 16/71 |

US 11,096,965 B2

COMPOSITIONS AND METHODS RELATED TO POLYCYTOTOXIC T CELLS

RELATED APPLICATIONS

This application is a § 371 national-stage application based on PCT/US2017/25842, filed Apr. 4, 2017, which claims the benefit of priority to U.S. Provisional Patent Application Ser. No. 62/317,941, filed Apr. 4, 2016, which is incorporated by reference herein in its entirety.

GOVERNMENT SUPPORT

This invention was made with government support under Grant No. AR068067, awarded by the National Institutes of Health. The government has certain rights in the invention.

BACKGROUND

CD8$^+$ cytotoxic T lymphocytes (CTL) are believed to contribute to host defenses against intracellular pathogens, but the specific CD8$^+$ cytotoxic subsets that are directly responsible for mediating antimicrobial effects remain unknown. The cytotoxic molecules granzyme B (GZMB) and perforin (PRF) act in concert with granulysin (GNLY). The importance of the role of CD8$^+$ CTLs in host defenses against intracellular pathogens is apparent from the clinical use of infliximab. This drug binds to surface TNF on granulysin-expressing cytotoxic CD8$^+$ T effector memory RA ($T_{EMRA}$) cells, resulting in their depletion, which is associated with susceptibility to reactivation of *M. tuberculosis*. Because granulysin is not expressed in mice, however, human models of infection are difficult to study. Further, staining for granulysin requires fixation, which precludes functional studies. Accordingly, cells expressing granulysin remain largely unexplored.

SUMMARY

Various aspects of the invention relate to compositions comprising polycytotoxic T cells. Some aspects relate to methods for obtaining a composition comprising polycytotoxic T cells. Some aspects relate to methods of administering a composition comprising polycytotoxic T cells to a subject. Some aspects relate to methods for monitoring an immune response in a subject, comprising determining the concentration of polycytotoxic T cells in the blood of the subject. Some aspects relate to methods for treating a condition or disease in a subject, comprising administering to the subject a composition comprising an antibody, or an antigen-binding portion thereof, that specifically binds to a protein expressed by a polycytotoxic T cell.

In some aspects, provided herein are methods of adoptive immunotherapy comprising administering compositions disclosed herein (e.g., compositions comprising polycytotoxic T cells, such as autologous or allogenic T cells).

In some aspects, provided herein are methods for monitoring an immune response in a subject by determining the concentration of polycytotoxic T cells in the blood of the subject. Determining the concentration of polycytotoxic T cells in the blood of the subject may be accomplished using any suitable method, such as flow cytometry, fluorescence-activated cell sorting, magnetic-activated cell sorting, immunohistochemistry, or RNA sequencing. In some embodiments, determining the concentration of polycytotoxic T cells in the blood of the subject comprises determining the frequency at which cells in the blood of the subject express one or more of granzyme B, perforin, granulysin, CD45RA, IL-15α receptor, IL-15β receptor, NKG2a, NKG2c, KIR2DL1, KIR2DS4, KIR3DL1, KLRC4, KLRF1, KLRC3, COL13A1, CHRNA7, TRDV2, LGR4, LAT2, ADAM28, SCN4A, GPR25, GPR75, KCNA6, TYROBP, ITGAX, RAMP1, KCNT1, CCR3 SIGLEC7, OTOF, ABCB4, CD300A, CD300C, CD3, CD8, CD56, CD94, ASCL2, ATP8B4, B3GAT1, BTBD17, C19orf35, C1orf21, CCL3, CCL4, CCL4L1, CD300LB, CLDND2, CMKLR1, CTBP2, CX3CR1, CXCR1, CYP1B1, EMR3, FAM20C, FAM49A, FCGR2A, FCGR2C, FCGR3A, FCGR3B, FCRL6, FGFBP2, FGR, GAS7, GLT1D1, GNLY, GPR141, GPR153, GPR56, GPR97, GSC, GZMB, GZMH, HBA1, HHEX, ISL2, ITGAM, ITGAX, KIR2DL1, KIR2DL3, KIR2DS4, KIR3DL1, KIR3DL2, KLRC1, KLRC2, KLRC3, KLRC4, KLRD1, KLRF1, LGALS9B, LILRA1, LILRA3, LILRB1, LILRB5, LRFN2, LRRC16B, LYN, MAFB, MGAM, MLC1, MYO3B, MYOM2, NCAM1, NCR1, NCS1, NKG7, NME8, NMUR1, NUAK1, PCDH1, PDGFD, PDGFRB, PIK3AP1, PODN, PRF1, PROK2, PRSS23, QPCT, RAB38, RASSF4, RCAN2, S1PR5, SETBP1, SGCD, SH2D1B, SH3RF1, SIGLEC7, SLC1A7, SLCO4C1, SORCS2, SPON2, SPRY2, TBX21, TFCP2L1, TM6SF1, TMCC3, TMEM255A, TRDV2, TRGJP2, TRGV, TRGV9, TYROBP, ZEB2, and ZNF683.

In some embodiments, determining the concentration of polycytotoxic T cells in the blood of the subject comprises determining the frequency at which cells in the blood of the subject express one or more of ADAMTS14, ADRB2, ARHGEF10L, ASCL2, ASGR2, BFSP1, BOK, BTBD17, C1orf177, C1orf21, CATSPER1, CCL3, CCL4, CCL4L2, CD160, CD1D, CD244, CD300LB, CD86, CDCl42EP1, CEBPA, CLDND2, CLEC17A, CMKLR1, COL13A1, CST7, CSTA, CTBP2, CX3CR1, CXCR1, CXXC4, DAB2, EFNA5, F7, FAM131B, FAM20C, FAM49A, FASLG, FBN2, FCGR2A, FCGR2B, FCGR2C, FCGR3A, FCGR3B, FCRL6, FGFBP2, FGR, FRMPD3, FZD2, GLT1D1, GNLY, GPR114, GPR141, GPR56, GPR97, GSC, GZMB, GZMH, HBA1, HBA2, HHEX, HSPA6, IGFBP7, IGHV1-69, IGLV2-11, IGLV3-10, IL1RN, ITGAM, KIF19, KIR2DL3, KIR2DS4, KIR3DL1, KLRC2, KLRD1, KLRF1, KYNU, LGALS2, LGR6, LILRA1, LILRA2, LILRB1, LILRB2, LILRB5, LIM2, LOXL3, LRP3, LRRC16B, LYN, MLC1, NCAM1, NCR1, NCS1, NKG7, NME8, NMUR1, NUAK1, OLIG1, PCDH1, PDGFD, PDGFRB, PIK3AP1, PLEK, PLOD1, PODN, PPP1R14C, PRF1, PRSS23, RAB38, RASSF4, RCVRN, RGS9, S1PR5, SDPR, SERPING1, SETBP1, SGCE, SH2D1B, SIGLEC7, SLAMF7, SLC1A7, SLCO4C1, SORCS2, SPRY2, STEAP3, STON2, STXBP6, TBX21, TCL1A, TFCP2L1, TLR4, TM4SF19, TM6SF1, TMCC3, TNNI2, TNS1, TRDC, TRDV2, TRGV8, TRGV9, TYROBP, VNN1, ZEB2, and ZNF683.

In some embodiments, the subject received an immune-modulating therapy prior to determining the concentration of polycytotoxic T cells. An immune-modulating therapy may be administered to the subject before and/or after determining the concentration of polycytotoxic T cells. The immune-modulating therapy may be a vaccine, interleukin (e.g., IL-2, IL-7, or IL-15), cytokine (e.g., interferon, G-CSF), chemokine (e.g., CCL3, CCL26, CXCL7), adoptive cell therapy (e.g., TIL or CAR-T therapy), or immunosuppressive therapy (e.g., corticosteroid, cytostatic, or anti-TNFα antibody or other antibody-based immunosuppressive therapy).

In some embodiments, the subject has an infection caused by an intracellular pathogen, an extracellular pathogen, a bacterial infection, a parasitic infection, a pathogenic strain of *E. coli*, leprosy, tuberculosis, Stevens-Johnson syndrome, toxic epidermal necrolysis, melanoma, or other cancer. In some embodiments, the subject has undergone an organ transplant. The subject may have had an allogeneic transplant or a xenogeneic transplant before or after determining the concentration of polycytotoxic T cells.

In some aspects, provided herein are methods of obtaining compositions comprising polycytotoxic T cells. In some embodiments, these methods comprise incubating a composition comprising T cells in media comprising interleukin 2, interleukin 7, or interleukin 15. The compositions comprising T cells disclosed herein (e.g., compositions comprising polycytotoxic T cells) may be substantially free of other cell types. In some embodiments, these methods comprise isolating peripheral blood mononuclear cells from whole blood, such as by separating peripheral blood mononuclear cells from red blood cells, fibrinogen, and platelets. In some embodiments, the T cells are sorted (e.g., T cells may be sorted by fluorescence-activated cell sorting or magnetic-activated cell sorting), e.g., by selecting cells that are positive for one or more of CD45RA, IL-15α receptor, IL-15β receptor, NKG2a, NKG2c, KIR2DL1, KIR2DS4, KIR3DL1, KLRC4, KLRF1, KLRC3, COL13A1, CHRNA7, TRDV2, LGR4, LAT2, ADAM28, SCN4A, GPR25, GPR75, KCNA6, TYROBP, ITGAX, RAMP1, KCNT1, CCR3 SIGLEC7, OTOF, ABCB4 CD300A, CD300C, CD3, CD8, CD56, CD94, and/or negative for CCR7.

In some aspects, provided herein are compositions comprising polycytotoxic T cells, e.g., wherein at least 10% of the T cells are polycytotoxic T cells. Compositions of polycytotoxic T cells prepared according to any of the methods disclosed herein are also contemplated.

Provided herein are methods of treating and/or preventing a disease or condition (e.g., an infection caused by an intracellular pathogen, an extracellular pathogen, a bacterial infection, a parasitic infection, a pathogenic strain of *E. coli*, leprosy, tuberculosis, melanoma, or other cancer) in a subject, comprising administering to the subject a composition disclosed herein (e.g., a composition comprising polycytotoxic T cells). T cells may be autologous or allogenic (e.g., allogeneic T cells selected from a cell bank). In some embodiments, the methods disclosed herein further comprise administering an immune-modulating therapy to the subject.

Disclosed herein are methods for increasing polycytotoxic T cells in a subject by administering to the subject a composition comprising an interleukin 2 receptor agonist, an interleukin 7 receptor agonist, or an interleukin 15 receptor agonist.

Also disclosed herein are methods of treating or preventing a disease (e.g., an infection caused by an intracellular pathogen, an extracellular pathogen, a bacterial infection, a parasitic infection, a pathogenic strain of *E. coli*, leprosy, tuberculosis, melanoma, or other cancer) in a subject by administering to the subject a composition comprising an interleukin 2 receptor agonist, an interleukin 7 receptor agonist, or an interleukin 15 receptor (e.g., IL-15Rα or IL-15Iσ) agonist. In some embodiments, the interleukin 2 receptor agonist is IL-2 or a fragment thereof; the interleukin 7 receptor agonist is IL-7 or a fragment thereof; or the interleukin 15 receptor agonist is IL-15 or a fragment thereof. In some embodiments, the agonist is a recombinant protein (e.g., recombinant IL-2, recombinant IL-7, and recombinant IL-15).

In some aspects, disclosed herein are methods of inhibiting polycytotoxic T cells in a subject, comprising administering to the subject an antibody, or an antigen-binding portion thereof, that specifically binds to CD45RA, IL-15α receptor, IL-15β receptor, NKG2a, NKG2c, KIR2DL1, KIR2DS4, KIR3DL1, KLRC4, KLRF1, KLRC3, COL13A1, CHRNA7, TRDV2, LGR4, LAT2, ADAM28, SCN4A, GPR25, GPR75, KCNA6, TYROBP, ITGAX, RAMP1, KCNT1, CCR3 SIGLEC7, OTOF, ABCB4 CD300A, CD300C, CD3, CD8, CD56, or CD94.

In some embodiments, provided herein are methods for treating or preventing an autoimmune disease (e.g., an autoimmune disease such as Stevens-Johnson syndrome or toxic epidermal necrolysis) in a subject, comprising administering to the subject an antibody, or an antigen-binding portion thereof, that specifically binds to CD45RA, IL-15α receptor, IL-15β receptor, NKG2a, NKG2c, KIR2DL1, KIR2DS4, KIR3DL1, KLRC4, KLRF1, KLRC3, COL13A1, CHRNA7, TRDV2, LGR4, LAT2, ADAM28, SCN4A, GPR25, GPR75, KCNA6, TYROBP, ITGAX, RAMP1, KCNT1, CCR3 SIGLEC7, OTOF, ABCB4 CD300A, CD300C, CD3, CD8, CD56, or CD94.

BRIEF DESCRIPTION OF THE DRAWINGS

FIG. 1A: Types of cytotoxic T cells. T cells from a healthy donor were sorted from PBMCs and stained with granulysin, perforin and granzyme cells were examined by confocal microscopy and representative images are shown of the types of cells seen.

FIG. 1B: PBMCs were stained with αCD3, GZMB, PRF, and GNLY, P-CTL, D-CTL, M-CTL and N-CTL cells were delineated by flow cytometry.

FIG. 2A: P-CTLs are enriched in T-lep vs. L-lep and induced by IL-15. PBMC from T-Lep or L-lep patients were examined for the % of $CD3^+$ T cells which co-express granzyme B perforin and granulysin (P-CTL).

FIG. 2B: Percentages of P-CTL in 7 T-lep patients were compared with 7 L-lep patients. P=0.004.

FIG. 4A: IL-15 induces the select proliferation of polycytotoxic T cells. PBMC were labeled with CFSE then treated with media, IL-15 or αCD3/CD28 for 5 d, then labeled with antibodies for CD3, granzyme B, perforin and granulysin. The number of P-CTLs was quantified, and the proliferation of P-CTL and M-CTL populations was measured and compared by CFSE dilution.

FIG. 4B: PBMC were prepared as in A and treated with IL-15 for 5, 7 or 12 days. Proliferation of P-CTLs was measured daily at each time point by CFSE dilution.

FIG. 7: P-CTLs selectively express NK markers. PBMC from a healthy donor were subjected to flow cytometry analyzing CTL populations for expression of CD56, NKG2c, and NKG2a.

FIG. 11A: Polycytotoxic T cells are more adept at killing as compared with other $CD8^+$ T cells. mlep infected MDMs were admixed with sorted populations of T cells in an E:T ratio of 2:1. The P-CTL, D-CTL, M-CTL and N-CTL composition of each sorted population was delineated by flow cytometry and is indicated below the x-axis. After 24 hours RNA and DNA was isolated from the target cells and the ratio of bacterial RNA to DNA was calculated to determine alive bacteria. This was used to calculate the percent killing as compared with infected MDMs alone without T cells ("No T cells") achieved under each condition.

FIG. 11B: the experiment was repeated as in FIG. 11A, but mTB infected macrophages were used as targets, the E:T ratio was 1:1, and after 24 hours lysates were plated on 7H10 agar plates and 3 weeks later colonies were counted. The percent killing over baseline was calculated.

FIG. 11C: Percent killing achieved in FIG. 11A with and without coating of targets with αCD3.

FIG. 11D: Percent killing achieved in FIG. 11B with and without coating of targets with αCD3.

FIG. 12A: The P-CTL signature is enriched in SJS/TEN. The gene signatures of P-CTL cells was compared with composite gene signatures derived from gene chip or whole exome sequencing of biopsy specimens from patients with either Stevens-Johnson syndrome or Toxic Epidermal Necrolysis using the programs DermDB and Savant http://pellegrini.mcdb.ucla.edu/Lab/Resources.html. The relative association of the matrices is indicated by Z score.

FIG. 12B: Individual genes identified in the P-CTL signature were examined for relative expression in SJS/TEN.

FIG. 16: CD56, NKG2c and NKG2a selective mark P-CTLs. 7 donors (NKG2c, a) and 2 donors (CD56) were analyzed for the selected NK markers. The percent P-CTL, D-CTL, M-CTL and N-CTL cells expressing these markers in each respective donor is shown. This data was used to generate FIG. 8.

FIG. 18: In silica signature analysis using Ingenuity (Qiagen) unexpectedly identified "Natural Killer Cell signaling" and "Cross talk between Dendritic Cells and Natural Killer Cells" as the top 2 canonical pathways in the two donors analyzed.

DETAILED DESCRIPTION

Figure 2D:
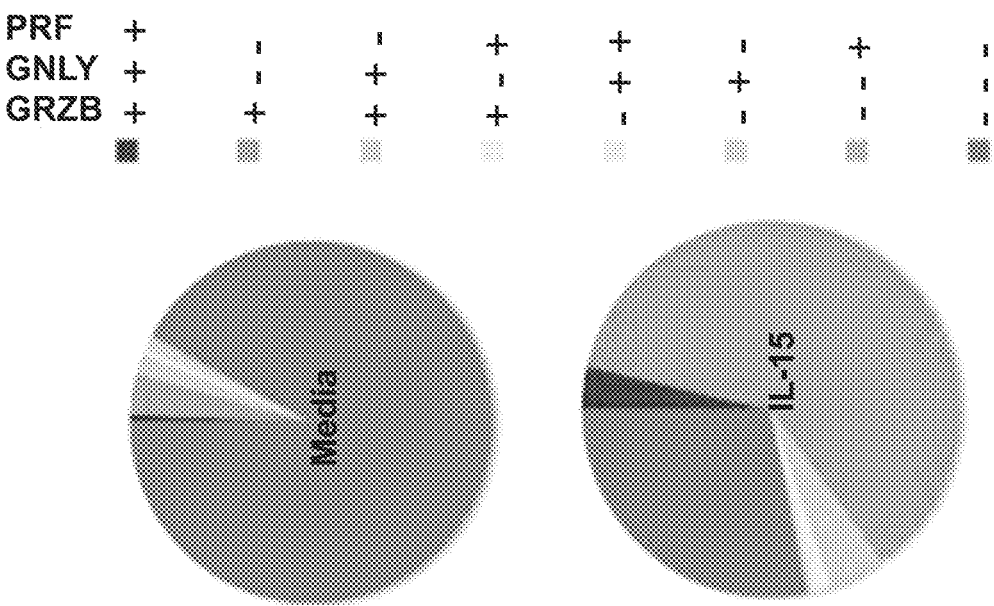
FIG. 2D: All cytotoxic cell populations were determined after treatment with media or IL-15 for 5 days. Shown are average results of 12 donors.

Polycytotoxic T cells are T lymphocytes that express granzyme B, perforin, and granulysin. Various aspects of the invention relate to the finding that polycytotoxic T cells may be isolated and expanded from peripheral blood mononuclear cells (PBMCs). Specifically, polycytotoxic T cells may be expanded by incubating them with interleukin 2 (IL-2), interleukin 7 (IL-7), or interleukin-15 (IL-15). Additionally, aspects of the invention relate to transcriptome of polycytotoxic T cells, which allows for their isolation.

In some embodiments, the invention relates to a method for monitoring an immune response in a subject, comprising determining the concentration of polycytotoxic T cells (i.e., T lymphocytes that express granzyme B, perforin, and granulysin) in the blood of the subject. Determining the concentration of polycytotoxic T cells in the blood of a subject may comprise determining the concentration of polycytotoxic T cells in a blood sample, obtained from the subject. The method may or may not comprise drawing blood from the subject. Determining the concentration of polycytotoxic T cells in the blood of the subject may be accomplished, for example, using flow cytometry, fluorescence-activated cell sorting, magnetic-activated cell sorting, immunohistochemistry, in situ hybridization, Northern blotting, Western blotting, reverse transcription-PCR, and/or RNA sequencing (e.g., whole transcriptome shotgun sequencing). In certain preferred embodiments, the method comprises flow cytometry or fluorescence-activated cell sorting.

In some embodiments, the invention relates to a method for monitoring an immune response in a subject, comprising determining the concentration of polycytotoxic T cells in a tissue sample obtained from the subject.

Determining the concentration of polycytotoxic T cells in the blood of the subject (or in a tissue sample) may comprise determining the frequency at which cells in the blood (or tissue sample) of the subject expresses one or more of CD45RA, IL-15α receptor, IL-15β receptor, NKG2a, NKG2c, KIR2DL1, KIR2DS4, KIR3DL1, KLRC4, KLRF1, KLRC3, COL13A1, CHRNA7, TRDV2, LGR4, LAT2, ADAM28, SCN4A, GPR25, GPR75, KCNA6, TYROBP, ITGAX, RAMP1, KCNT1, CCR3 SIGLEC7, OTOF, ABCB4 CD300A, CD300C, CD3, CD8, CD56, and CD94. The foregoing proteins are each membrane proteins, which may be monitored on live cells, for example, by flow cytometry or fluorescence-activated cell sorting. Nevertheless, any other protein that is enriched in polycytotoxic T cells, as identified herein, may be used to determine the concentration of polycytotoxic T cells in blood or in another sample. For example, granzyme B, perforin, and/or granulysin expression may be used to determine whether a cell is a polycytotoxic T cell, optionally, in combination with other markers. Granzyme B, perforin, and granulysin are intracellular proteins, however, and thus, their expression in a cell cannot be directly monitored without permeabilizing the cell membrane, which may compromise cell viability.

Determining the concentration of polycytotoxic T cells in the blood of the subject (or in a tissue sample) may comprise determining the frequency at which cells in the blood (or tissue sample) of the subject expresses one or more of ASCL2, ATP8B4, B3GAT1, BTBD17, C19orf35, C1orf21, CCL3, CCL4, CCL4L1, CD300LB, CLDND2, CMKLR1, CTBP2, CX3CR1, CXCR1, CYP1B1, EMR3, FAM20C, FAM49A, FCGR2A, FCGR2C, FCGR3A, FCGR3B, FCRL6, FGFBP2, FGR, GAS7, GLT1D1, GNLY, GPR141, GPR153, GPR56, GPR97, GSC, GZMB, GZMH, HBA1, HHEX, ISL2, ITGAM, ITGAX, KIR2DL1, KIR2DL3, KIR2DS4, KIR3DL1, KIR3DL2, KLRC1, KLRC2, KLRC3, KLRC4, KLRD1, KLRF1, LGALS9B, LILRA1, LILRA3, LILRB1, LILRB5, LRFN2, LRRC16B, LYN, MAFB, MGAM, MLC1, MYO3B, MYOM2, NCAM1, NCR1, NCS1, NKG7, NME8, NMUR1, NUAK1, PCDH1, PDGFD, PDGFRB, PIK3AP1, PODN, PRF1, PROK2, PRSS23, QPCT, RAB38, RASSF4, RCAN2, S1PR5, SETBP1, SGCD, SH2D1B, SH3RF1, SIGLEC7, SLC1A7, SLCO4C1, SORCS2, SPON2, SPRY2, TBX21, TFCP2L1, TM6SF1, TMCC3, TMEM255A, TRDV2, TRGJP2, TRGV2, TRGV9, TYROBP, ZEB2, and ZNF683.

Determining the concentration of polycytotoxic T cells in the blood of the subject (or in a tissue sample) may comprise determining the frequency at which cells in the blood (or tissue sample) of the subject expresses one or more of ADAMTS14, ADRB2, ARHGEF10L, ASCL2, ASGR2, BFSP1, BOK, BTBD17, C1orf177, C1orf21, CATSPER1, CCL3, CCL4, CCL4L2, CD160, CD1D, CD244, CD300LB, CD86, CDC42EP1, CEBPA, CLDND2, CLEC17A, CMKLR1, COL13A1, CST7, CSTA, CTBP2, CX3CR1, CXCR1, CXXC4, DAB2, EFNA5, F7, FAM131B, FAM20C, FAM49A, FASLG, FBN2, FCGR2A, FCGR2B, FCGR2C, FCGR3A, FCGR3B, FCRL6, FGFBP2, FGR, FRMPD3, FZD2, GLT1D1, GNLY, GPR114, GPR141, GPR56, GPR97, GSC, GZMB, GZMH, HBA1, HBA2, HHEX, HSPA6, IGFBP7, IGHV1-69, IGLV2-11, IGLV3-10, IL1RN, ITGAM, KIF19, KIR2DL3, KIR2DS4, KIR3DL1, KLRC2, KLRD1, KLRF1, KYNU, LGALS2, LGR6, LILRA1, LILRA2, LILRB1, LILRB2, LILRB5, LIM2, LOXL3, LRP3, LRRC16B, LYN, MLC1, NCAM1, NCR1, NCS1, NKG7, NME8, NMUR1, NUAK1, OLIG1, PCDH1, PDGFD, PDGFRB, PIK3AP1, PLEK, PLOD1, PODN, PPP1R14C, PRF1, PRSS23, RAB38, RASSF4, RCVRN, RGS9, S1PR5, SDPR, SERPING1, SETBP1, SGCE, SH2D1B, SIGLEC7, SLAMF7, SLC1A7, SLCO4C1, SORCS2, SPRY2, STEAP3, STON2, STXBP6, TBX21, TCL1A, TFCP2L1, TLR4, TM4SF19, TM6SF1, TMCC3, TNNI2, TNS1, TRDC, TRDV2, TRGV8, TRGV9, TYROBP, VNN1, ZEB2, and ZNF683.

In some embodiments, the subject may have received an immune-modulating therapy prior to determining the concentration of polycytotoxic T cells. Thus, monitoring an immune response may comprise monitoring whether an immune-modulating therapy increased or decreased the concentration of polycytotoxic T cells. For example, an immune-modulating therapy may be administered to increase an immune response, e.g., against a pathogen or against cancer, and the concentration of polycytotoxic T cells may be monitored to assess the efficacy of the therapy. Alternatively, an immune-modulating therapy may be administered to decrease an immune response, e.g., in an auto-immune disease, such as Stevens-Johnson syndrome or toxic epidermal necrolysis, and the concentration of polycytotoxic T cells may be monitored to assess the efficacy of the therapy.

The method may further comprise administering an immune-modulating therapy to the subject, e.g., before or after determining the concentration of polycytotoxic T cells. The immune-modulating therapy may be, for example, a vaccine, interleukin (e.g., IL-2, IL-7, or IL-15, IL-21), cytokine (e.g., interferon, G-CSF), chemokine (e.g., CCL3, CCL26, CXCL7), adoptive cell therapy (e.g., TIL or CAR-T therapy), or immunosuppressive therapy (e.g., corticosteroid, cytostatic, or anti-TNFα antibody or other antibody-based immunosuppressive therapy). The immune-modulating therapy may be, for example, infliximab, golimumab, adalimumab, certolizumab pegol, or etanercept. The immune-modulating therapy may be basiliximab, daclizumab, or rituximab. The immune-modulating therapy may be, for example, interleukin 2 (IL-2), interleukin 7 (IL-7), or interleukin 15 (IL-15). In preferred embodiments, the immune-modulating therapy may be a vaccine.

In some embodiments, the subject may have an infection caused by an intracellular pathogen, such as a bacterial infection or a parasitic infection. For example, the subject may have leprosy or tuberculosis. In some embodiments, the subject may have an infection caused by an extracellular pathogen, such as a bacterial infection or a parasitic infection. The subject may have cancer, such as melanoma.

The subject may have an auto-immune disease, such as Stevens-Johnson syndrome or toxic epidermal necrolysis. The subject may have hepatitis B. The subject may have arthritis. The subject may have transplant rejection (e.g., the subject may have received a kidney, liver, heart, lung, skin, bone marrow, or cornea transplant). The subject may have graft versus host disease or the subject may be at risk of developing graft versus host disease. The subject may have druginduced hypersensitivity syndrome, or the subject may be at risk for developing druginduced hypersensitivity syndrome.

In some embodiments, the subject may have undergone an organ or tissue transplant, such as an allogeneic transplant or a xenogeneic transplant. The polycytotoxic T cells may be monitored in a subject who has undergone an organ or tissue transplant, for example, to determine whether the subject is mounting a polycytotoxic T cell-mediated immune response against the transplant. The method may further comprise administering an allogeneic transplant or a xenogeneic transplant to the subject before or after determining the concentration of polycytotoxic T cells.

In some embodiments, the invention relates to a method for obtaining a composition comprising polycytotoxic T cells, comprising incubating a composition comprising T cells in media comprising interleukin 2, interleukin 7, or interleukin 15. In preferred embodiments, the composition comprising T cells is substantially free from other cell types. For example, T cells may be isolated from whole blood using known methods. The method may comprise isolating peripheral blood mononuclear cells from whole blood. Isolating peripheral blood mononuclear cells from whole blood may comprise separating the peripheral blood mononuclear cells from cells and cell fragments of the myeloid lineage, such as erythrocytes, basophils, neutrophils, eosinophils, macrophages, and/or platelets. Isolating peripheral blood mononuclear cells from whole blood may comprise separating the peripheral blood mononuclear cells from clotting factors, such as fibrinogen and/or fibrin. The method may comprise sorting the T cells, e.g., by magnetic-activated cell sorting or fluorescence-activated cell sorting.

Sorting T cells may comprise selecting cells that are positive for one or more of CD45RA, IL-15α receptor, IL-15β receptor, NKG2a, NKG2c, KIR2DL1, KIR2DS4, KIR3DL1, KLRC4, KLRF1, KLRC3, COL13A1, CHRNA7, TRDV2, LGR4, LAT2, ADAM28, SCN4A, GPR25, GPR75, KCNA6, TYROBP, ITGAX, RAMP1, KCNT1, CCR3 SIGLEC7, OTOF, ABCB4 CD300A, CD300C, CD3, CD8, CD56, CD94, and/or negative for CCR7, e.g., using an antibody that specifically binds to the extracellular region of one of the foregoing.

In some aspects, the invention relates to a composition comprising polycytotoxic T cells. In some embodiments, at least 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, 96%, 97%, 98%, or 99% of the cells in the composition may be polycytotoxic T cells. In preferred embodiments, at least 10% of the cells in the composition comprise polycytotoxic T cells, more preferably, at least 50%. In some embodiments, at least 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, 96%, 97%, 98%, or 99% of the T cells in the composition may be polycytotoxic T cells. In preferred embodiments, at least 10% of the T cells in the composition comprise polycytotoxic T cells, more preferably, at least 50%.

In some aspects, the invention relates to a method of treating or preventing a disease or condition in a subject, comprising administering to the subject a composition comprising T cells, wherein the composition comprises polycytotoxic T cells (e.g., as described herein). For example, at least 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, 96%, 97%, 98%, or 99% of the cells in the composition are polycytotoxic T cells. In preferred embodiments, at least 10% of the cells in the composition are polycytotoxic T cells, more preferably, at least 50%. In some embodiments, at least 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, 96%, 97%, 98%, or 99% of the T cells in the composition are polycytotoxic T cells. In preferred embodiments, at least 10% of the T cells in the composition are polycytotoxic T cells, more preferably, at least 50%. In some aspects, provided herein are methods of adoptive immunotherapy comprising administering compositions disclosed herein (e.g., compositions comprising polycytotoxic T cells). Polycytotoxic T cells may be allogenic or autologous. In some embodiments, the polycytotoxic T cells may be selected from a cell bank and administered to the subject (e.g., a subject in need thereof).

The term "preventing" as used herein, refers to delaying the onset of a disease or condition or a symptom thereof, reducing the severity of a disease or condition or a symptom thereof, reducing the likelihood that a disease or condition or a symptom thereof will occur in a subject, reducing the frequency that a disease or condition or a symptom thereof occurs in a population, and/or slowing or halting the progression of a disease or condition or the likelihood that the disease or condition will progress. The subject may be, for example, a primate, preferably a human.

The disease or condition may be an infection caused by an intracellular pathogen, such as a bacterial infection or a parasitic infection. For example, the disease or condition may be leprosy or tuberculosis. The disease or condition may be an infection caused by an extracellular pathogen, such as a bacterial infection or a parasitic infection. The disease or condition may be cancer, such as melanoma.

The method may further comprising administering an immune-modulating therapy to the subject.

In some aspects, the invention relates to a method for increasing the number of polycytotoxic T cells in a subject, comprising administering to the subject an interleukin 2 receptor agonist (e.g., interleukin 2), an interleukin 7 receptor agonist (e.g., interleukin 7), or an interleukin 15 receptor agonist (e.g., interleukin 15). The interleukin 15 receptor may be IL-15Rα or IL-15Rβ. In some embodiments, the interleukin receptor (e.g., interleukin 2 receptor, interleukin 7 receptor, or interleukin 15 receptor) agonist is a polypeptide. In some embodiments, polypeptides, or fragments thereof, can be modified according to well-known pharmacological methods in the art (e.g., pegylation, glycosylation, oligomerization, etc.) In some embodiments, the agonist is a recombinant polypeptide (e.g., recombinant IL-2, recombinant IL-7, and recombinant IL-15). The term "recombinant" polypeptide means a polypeptide which either does not occur in nature or is linked to another polypeptide in a non-natural arrangement. In some embodiments, the polypeptide is a chimeric or fusion polypeptide. A fusion or chimeric polypeptide can be produced by standard recombinant DNA techniques. For example, DNA fragments coding for the different polypeptide sequences are ligated together in-frame in accordance with conventional techniques, for example by employing blunt-ended or staggerended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, Current Protocols in Molecular Biology, Ausubel et al., eds., John Wiley & Sons: 1992). Moreover, many expression vectors are commercially available that already encode a fusion moiety. The agonist may be a polypeptide, and the polypeptide may have at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 95%, or at least 100% homology to IL-2. The agonist may be a polypeptide, and the polypeptide may have at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 95%, or at least 100% homology to IL-7. The agonist may be a polypeptide, and the polypeptide may have at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 95%, or at least 100% homology to IL-15.

In preferred embodiments, the interleukin 2 receptor agonist is IL-2. In preferred embodiments, the interleukin 7 receptor agonist is IL-7. In preferred embodiments, the interleukin 15 receptor agonist is IL-15. In some embodiments, IL-15 comprises an amino acid substitutions of the asparagine residue at position 72. More information on IL-15 agonists can be found in Xu et al. J Immunol. (2009) 183(6): 3598, hereby incorporated in its entirety.

In some aspects, the invention relates to a method of treating or preventing a disease in a subject, comprising administering to the subject a composition comprising an interleukin 2 receptor agonist (e.g., interleukin 2), an interleukin 7 receptor agonist (e.g., interleukin 7), or an interleukin 15 receptor agonist (e.g., interleukin 15). The interleukin 15 receptor may be IL-15Rα or IL-15Rβ. The disease or condition may be an infection caused by an intracellular pathogen, such as a bacterial infection or a parasitic infection. The disease or condition may be an infection caused by an extracellular pathogen, such as a bacterial infection (e.g., caused by a pathogenic strain of E. coli) or a parasitic infection. For example, the disease or condition may be leprosy or tuberculosis. The disease or condition may be cancer, such as melanoma.

In some embodiments, the agonist is a recombinant protein (e.g., recombinant IL-2, recombinant IL-7, and recombinant IL-15). An agonist may be a fusion or chimeric protein.

IL-15 is an immunostimulatory cytokine trans-presented with the IL-15 receptor a chain to the shared IL-2/IL-15Rβ and common γ chains displayed on the surface of T cells and NK cells. To further define the functionally important regions of this cytokine, activity and binding studies were conducted on human IL-15 muteins generated by site-directed mutagenesis. Amino acid substitutions of the asparagine residue at position 72, which is located at the end of helix C, were found to provide both partial agonist and superagonist activity, with various non-conservative substitutions providing enhanced activity. Particularly, the N72D substitution provided a 4-5 fold increased in biological activity of the IL-15 mutein compared to the native molecule based on proliferations assays with cells bearing human IL-15Rβ and common γ chains. More information on IL-15 agonists can be found in Xu et al. J Immunol. 2009 Sep. 15; 183(6): 3598, hereby incorporated in its entirety.

In some embodiments, the invention relates to a method of inhibiting polycytotoxic T cells in a subject, comprising administering to the subject an antibody, or an antigen-binding portion thereof, that specifically binds to a protein expressed by a polycytotoxic T cell. In some embodiments, the invention relates to a method for treating or preventing an autoimmune disease in a subject, comprising administering to the subject an antibody, or an antigen-binding portion thereof, that specifically binds to a protein expressed by a polycytotoxic T cell. The method may comprise administering to the subject an antibody, or an antigen-binding portion thereof, that specifically binds to the extracellular portion of a membrane protein that displays elevated expression on polycytotoxic T cells relative to other T cells (such as non-cytotoxic T cells). The protein (e.g., membrane protein) may be, for example, CD45RA, IL-15α receptor, IL-15β receptor, NKG2a, NKG2c, KIR2DL1, KIR2DS4, KIR3DL1, KLRC4, KLRF1, KLRC3, COL13A1, CHRNA7, TRDV2, LGR4, LAT2, ADAM28, SCN4A, GPR25, GPR75, KCNA6, TYROBP, ITGAX, RAMP1, KCNT1, CCR3 SIGLEC7, OTOF, ABCB4 CD300A, CD300C, CD3, CD8, CD56, or CD94. The autoimmune disease may be, for example, Stevens-Johnson syndrome or toxic epidermal necrolysis. In certain embodiments, the antibody is a chimeric antibody. In preferred embodiments, the antibody is a humanized antibody or a human antibody.

Having now described the present invention in detail, the same will be more clearly understood by reference to the following examples, which are included herewith for purposes of illustration only and are not intended to limit the invention.

EXEMPLIFICATION

Introduction

CD8+ cytotoxic T lymphocytes (CTL) are thought to contribute to host defense against intracellular pathogens but which specific CD8+ cytotoxic subsets are directly responsible for mediating antimicrobial effects are unknown. The importance of the role of CD8+ CTLs in host defense against intracellular pathogens from the clinical use of infliximab. This drug binds to surface TNF on granulysin expressing cytotoxic CD8+ T effector memory RA ($T_{EMRA}$) cells resulting in their depletion, and this is associated with susceptibility to reactivation of M. tuberculosis (1). It has been shown that the cytotoxic molecules granzyme B (GZMB) and perforin (PRF) act in concert with granulysin (GNLY) to facilitate elimination of intracellular pathogens (2, 3) and recently, T cells expressing these three cytotoxic molecules (GZMB, GNLY and PRF)—termed 'polycytotoxic' (P-CTL)—have been shown to correlate with protection against M. tuberculosis (4). Because granulysin is not expressed in mice (5), human models of infection are difficult to study, and staining for GNLY requires fixation, which precludes functional studies, these cells are largely unexplored. Therefore, the uniquely human disease leprosy caused by infection with Myocobacetrium leprae to was used investigate this subset of cells.

Leprosy, has provided an extraordinary model, because of its accessible localization to skin, to investigate the human immune system. The disease presents with a clinical and immunologic spectrum (6, 7), providing an opportunity to study resistance vs. susceptibility to widespread infection. Patients with the resistant tuberculoid form (T-lep) manifest strong cell mediated immunity (CMI) to the pathogen, skin lesions are few and bacilli rare. CMI, however, is absent/diminished in the susceptible lepromatous form (L-lep) (7, 8), skin lesions are numerous and growth of the pathogen is unabated.

Clinical presentations of leprosy correlate with the cytokine profile within the host (8). In the T-lep form, T cells that produce IL-2 and IFN-γ, termed Th1 cells, activate a CMI response to kill or inhibit the growth of the pathogen resulting in the mild or self-curing disease. In the L-lep state T cells that produce IL-4, IL-5 and IL-10, termed Th2 cells, inhibit the intracellular CMI responses and direct a predominantly humoral immune response, resulting in progressive infection. The "type 1" cytokine pattern, typified by IL-2, IFN-γ, and IL-15 is found in lesions of resistant T-lep patients (8). In contrast the "type 2" cytokines, such as IL-4, IL-5 and IL-10, predominate in the lesions of susceptible L-lep patients (8). Therefore, type-1 cytokine responses appear to be necessary for the generation of immunologic resistance in leprosy.

Mechanisms leading to resistance in the T-lep state may include direct activation of macrophages to kill intracellular bacteria through cytokine release by Th1 cells (9), however mycobacteria have evolved defenses to evade such mechanisms (10) and thus require alternate methods of killing including delivery of antimicrobial peptides via cytotoxic granules. In support of this, the cytotoxic molecule granulysin has been shown to correlate with host defense against *M. leprae* (11), have direct cytotoxic effects on mycobacteria (12), and is upregulated along with perforin after BCG vaccination (13). This prompted our examination of these three molecules within CTLs from healthy donors initially, and subsequently across resistant and susceptible states of leprosy.

The disease leprosy was used to examine heterogenous cytotoxic T cell subsets across the spectrum of infection. P-CTLs are increased in resistant vs. susceptible state of leprosy. It is shown herein that these cells are CD8$^+$ T$_{EMRA}$ cells which are controlled by IL-15, IL-2 and IL-7. Using RNA sequencing, surface markers that specifically mark this population were identified and it is shown that these are enriched for numerous modulatory (activating or inhibiting) NK cell receptors. The number of modulatory NK receptors expressed directly correlates with the number of cytotoxic molecules expressed by a population. It is also shown that P-CTLs are more efficient at killing than other CD8$^+$ T cells. Finally, it is shown herein that the P-CTL signature is enriched in the disease states of Stevens-Johnson syndrome and Toxic Epidermal Necrolysis.

Methods

Patients and healthy subjects. Leprosy skin biopsy and blood specimens were obtained through collaborations with Drs. Thomas Rea, and Maria Theresa Ochoa at the Los Angeles County/University of Southern California Medical Center and Dr. Euzenir Sarno at the Oswaldo Cruz Institute in Brazil. The diagnosis of leprosy was established by means of clinical criteria according to Ridley (6). Healthy donors served as controls and were used for baseline examination. The race of the leprosy patients was concealed, but based on epidemiology of the leprosy patients in Los Angeles, the majority of patients are of Hispanic or Asian descent; a large proportion of healthy donor blood comes from donors in these ethnic/gender categories to best match the population of leprosy donors.

Isolation and expansion of P-CTL from PBMC and human T cells using cytokines. PBMCs were isolated from the peripheral blood of healthy donors, or patients with a diagnosis of leprosy using Ficoll-Paque gradients (Amersham Biosciences) and either cultured directly or T cells were negatively selected by subjecting to magnetic bead separation using immunomagnetic negative selection (Easy Sep, Stem cell technologies) and then cultured in RPMI 1640 with 10% fetal calf serum (FCS, Hyclone) with or without cytokines 5, 7, or 12 days. The following cytokines were used IL-15 15 ng/mL (R&D systems), IL-7 long/mL (BioLegend), IL-2 50 nM (Chiron), αCD3/28 microbeads (Dynabeads, Gibco), IL-10 10 ng/mL (R&D systems).

Calculating the percentage of P-CTLs. Polycytotoxic T lymphocytes (P-CTL) were defined as CD3+ cells co-expressing GZMB, PRF, and GNLY. The % P-CTL of CD3$^+$ T cells was calculated using multicolor flow cytometry examining by dividing the number of P-CTL events by dividing the total number of CD3$^+$ events. Flowjo (Flowjo, Enterprise) software was used to analyze flow cytometry data.

Analysis of memory subpopulations. Florescence activated cell sorting (FACS) was used to analyze memory subpopulations of P-CTLs. Cells were labeled with combinations of CD3, CD8, CCR7, CD45RA, and in some cases CD45RO if to distinguish between naïve, T$_{CM}$ T$_{EM}$ and T$_{EMRA}$ cells.

Proliferation. PBMCs were isolated from donors as described above. Cells were labeled ex-vivo with CFSE XmM (Cell Trace, Invitrogen) and cultured with IL-15 15 ng/mL, media, or αCD3/28 microbeads. Flow cytometry was employed examining CD3, CD8, CD4, GZMB, PRF, GNLY and CFSE staining to interrogate proliferation within the P-CTL, D-CTL, M-CTL and N-CTL compartments by examining CFSE dilution. Flowjo software (Flowjo, Enterprise) was used to analyze flow cytometry data.

Cell sorting of cytotoxic cell populations and RNA isolation from fixed and sorted cells. RNA was isolated from fixed sorted cells based on the MARIS (method for analyzing RNA following intracellular sorting) protocol as described by Hrvatin et al (14). Briefly, florescence activated cell sorting (FACS) was used to obtain highly purified populations of P-CTL, D-CTL, M-CTL and N-CTL cells from donors based on staining with CD3, GZMB, PRF, and GNLY as described above. Prior to sorting cells were fixed in 2% EM grade paraformaldehyde (Electron Microscopy Sciences) and permeabilized with 0.5% DNAse/RNAse free saponin (Sigma) to permit intracellular staining. All staining and sorting took place in DNAse/RNAse free PBS supplemented with microbiology grade BSA (Gemini-Bio products) in the constant presence of RNAsin plus RNAase inhibitor (Promega) 1:25 to 1:100 (1:100 for washes, 1:25 for staining and sorting). After sorting RNA was isolated using Recover All Total Nucleic Acid Isolation kit (Ambion) as per manufacturer's instructions, with the same modification to the protocol used as described by Hrvatin et al. (14).

RNA sequencing of cytotoxic cell populations. Sequencing libraries were constructed from mRNA using Illumina TruSeq Stranded Total RNA Sample Prep and sequenced at the Neurogenomics Core at UCLA by single-end sequencing on an Illumina HiSeq2500.

Analysis of RNA sequencing data. RNA seq analysis was performed as described (need ref). Briefly, sequence reads were be mapped to each gene in the human genome, gene expression was calculated based on the number of aligned reads, and was normalized by the total reads per sample and length, reads per kilobase per million reads (RPKM). Once the expression level of each gene was determined, downstream mRNA sequencing data analysis was performed as outlined below.

Analysis of genes expressed across cytotoxic cell populations and generation of the specific P-CTL signature. Once gene expression data for each cytotoxic population was obtained, expression in each of the cytotoxic populations was compared with the non-cytotoxic population and select genes that were expressed 2 fold or greater to create a 'population signature.' Three way comparisons between each CTL 'population signature' were performed to generate specific signatures for each CTL population. For example, to generate the "specific P-CTL signature" P-CTL genes were first compared with N-CTL genes and selected all genes expressed 2 fold or greater over a threshold of 10 normalized counts to obtain the 'P-CTL signature.' The 'P-CTL signature' was compared with the 'D-CTL' and 'M-CTL signatures' generated and select genes that are specifically enriched in P-CTLs over the other 2 populations (2 fold over M-CTL and 1.5 over D-CTL). This specific signature was then analyzed by Ingenuity (Qiagen) to sort genes expressed on the cell membrane as candidate P-CTL markers to test for validation.

Validation of P-CTL markers by flow cytometry. Once identified (as outlined above), surface markers were validated. PBMCs or T cells isolated as described above were interrogated by flow cytometry for expression of CD56, NKG2a and NKG2c across P-CTL, D-CTL, M-CTL and N-CTL populations.

Generation of target cells. To assess killing of M. leprae, or M. tuberculosis infected cells were used to infected myeloid derived monocytes (MDMs) as targets. MDMs are known to have a high capacity to engulf and become infected by mycobacteria but a low intrinsic ability to kill without presence of IFNγ (15) making them ideal targets for the assays. Briefly, 5-7 days prior to infection with bacteria monocytes were be purified from peripheral blood using Ficoll-Paque gradients (Amersham Biosciences) followed by negative selection of CD14+CD16+ cells using the EasySep Human Monocyte Enrichment Kit without CD16 Depletion (Stem Cell Technologies). Negatively selected cells were cultured for 5-7 days in RPMI 1640 with 10% super low Ig FCS without antibiotics in the presence of M-CSF to differentiate into MDMs as previously described (15-17). After 5 days MDMs were infected with M. leprae or M. tuberculosis at an MOI of 10.

Coating MDMs with αCD3. Because isolated effector CTL subsets were of varying TCR specificities, MDM target cells were coated with αCD3 10-20 ng/mL by incubating with this antibody for 15 minutes prior to admixing effector cells as previously described (3, 18). Breifly, 24 hours after infection with bacteria MDMs were washed and then admixed with 10 ng-20 ng/mL αCD3 in complete media. Cells were subsequently washed and then ready to be mixed with effector cells.

Cell sorting of viable cytotoxic cell populations. Florescence activated cell sorting (FACS) was used to purify CD8+ P-CTLs from other populations of CTLs by labeling cells with CD3, CD8 and combinations of the identified surface markers as were validated above. Staining was performed in sterile PBS with 10% FCS and sorting was performed in complete media.

Cytotoxicity assays. P-CTLs and other CTL subsets were admixed with differentiated, infected, and αCD3 coated (or not) MDMs as described above in effector to target ratios of either 2:1 or 1:1, depending on yield after sorts. After 24 hours of incubation all cells were lysed and bacterial cell death was quantified as described below.

Quantification of killing of M. leprae. To determine the killing of M. leprae RNA and DNA were extracted from lysates and adherent cells. qPCR was used to determine the RNA to DNA ratio as previously described (19), which was used as a surrogate to measure viability.

Quantificiation of killing of M. tuberculosis. To determine killing of M. tuberculosis cell lysates were plated on 7H10 agar plates at varying dilutions between $10^1$ and $10^4$, bacterial colonies were enumerated after 21 days of growth at 37 degrees.

Flow Cytometry Antibodies. The following antibodies were used: αCD3-PerCp (clone SK7 BD Biosciences), αCD3-Pacific Blue (clone UCHT1 BioLegend), αCD3 UV395 (clone SK7 BD Biosciences), αCD8-BV605 (clone RPA-T8 BioLegend), αCD4 Pe-Cy7 (clone OKT4 BioLegend), αGZMB APC (clone GRB05 Invitrogen), αGZMB Pacific Blue (clone GB11 BioLegend), αPRF FITC (BD Biosceinces), αPRF PeCy7 (clone dG9 eBioscience), αGNLY PE (clone DH2 eBioscience), αCCR7 BV605 (clone GO43H7 BioLegend), αCCR7 APC Cy7 (clone G043H7 BioLegend), αCD45RA PeCy7 (clone H1100 eBiosceince), αCD45RO BV421 (clone UCHL1 BioLegend), αCD56 PerCp (clone HCD56 BioLegend), αCD56 APC (clone CMSSB eBioscience), αNKG2a FITC (Miltenyi), αNKG2c APC (Miltenyi).

Comparison of P-CTL genes with SJS/TEN genes. We compared gene signatures of P-CTL cells with composite gene signatures derived from gene chip or whole exome sequencing of biopsy specimens from patients with either Stevens-Johnson syndrome or Toxic Epidermal Necrolysis using the programs DermDB and Savant http://pellegrin-i.mcdb.ucla.edu/Lab/Resources.html.

Results

Heterogeneity in the cytotoxic T cell compartment and defining the polycytotoxic T cell (P-CTL). To elucidate which cells may be responsible for delivering the necessary cytotoxic payload to control intracellular infection healthy donors were examined by confocal microscopy (FIG. 1A) and flow cytometry (FIG. 1B). In general, it was found that cytotoxic cells came in one of three types. Monocytotoxic (M-CTL) cells expressed only GZMB, dicytotoxic (D-CTL) cells expressed PRF and GZMB and polycytotoxic (P-CTL) cells expressed GNLY, PRF and GZMB (FIG. 1A and FIG. 1B).

Figure 2C:
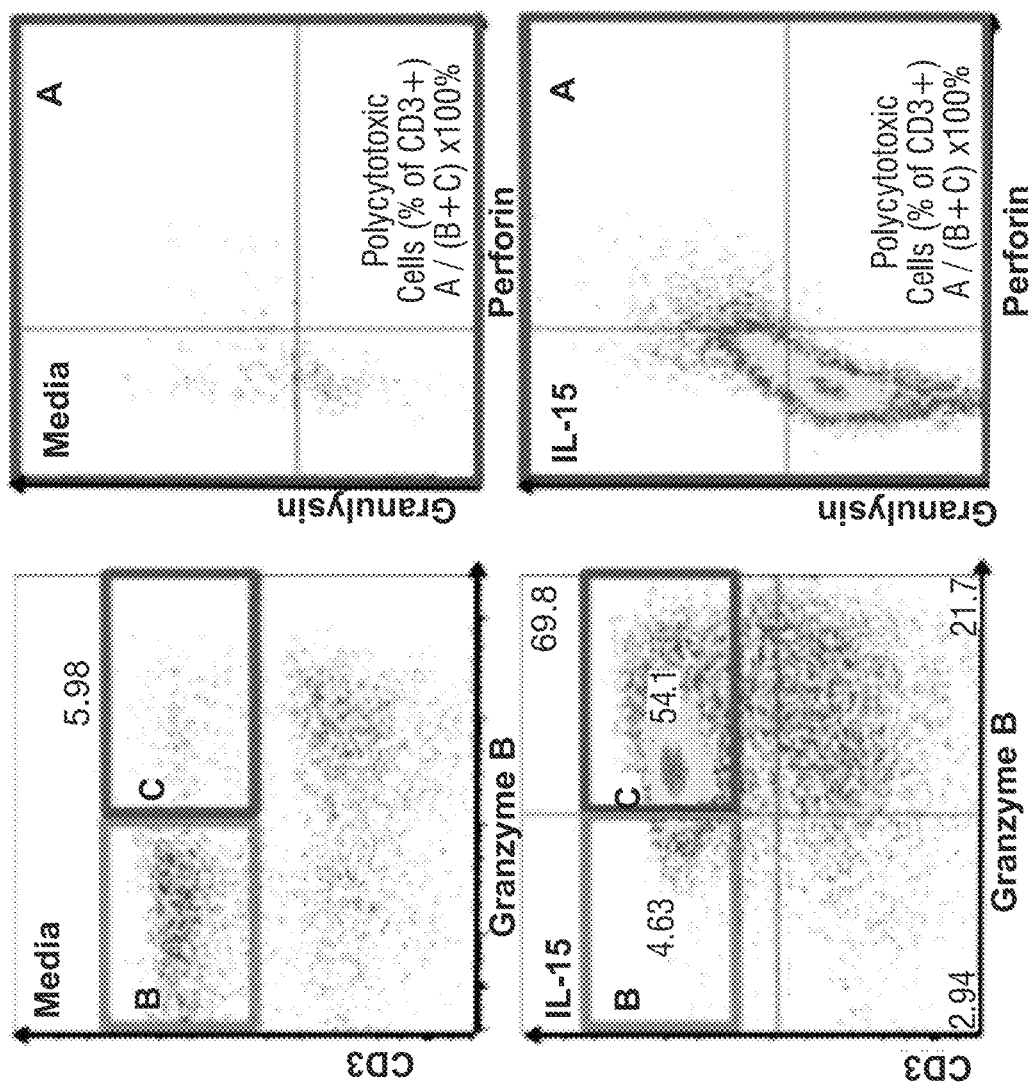
FIG. 2C: PBMCs from a healthy donor was treated with IL-15 or media for 5 days and % P-CTL were calculated.
Figure 3:
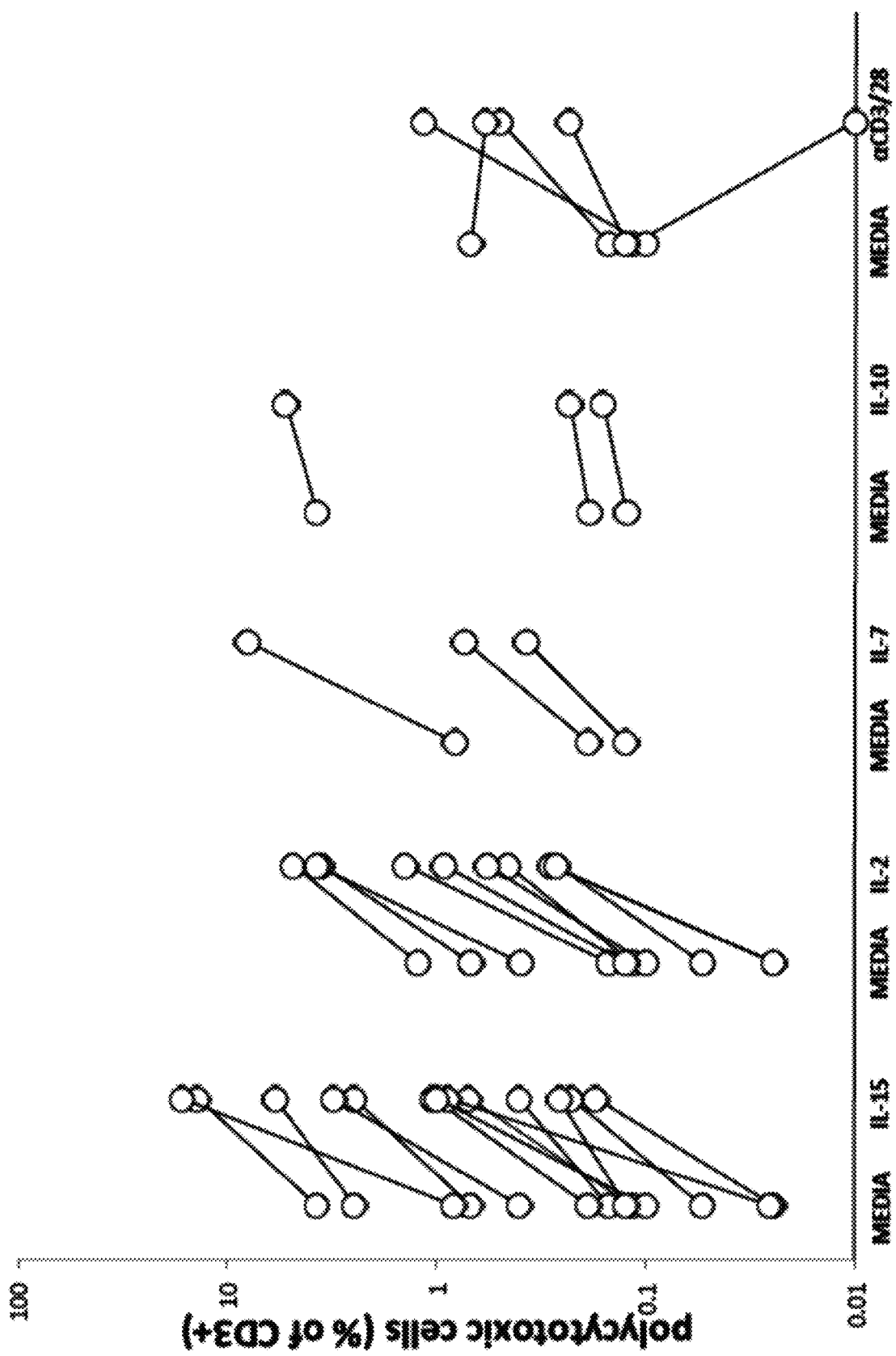
FIG. 3: IL-15, IL-2, IL-7 expand the P-CTL compartment while IL-10 and αCD3/28 have no effect. PBMCs from healthy donors were treated with either IL-15 (N=12), IL-2 (N=8), IL-7 (N=3), IL-10 (N=3), or αCD3/28 (N=4) for 5 days, and compared with media treatment. The % P-CTL was determined by flow cytometry. P<0.05

P-CTLs correlate with T-lep and are influenced by T-lep cytokines. It was examined the percentage of P-CTL across the spectrum of leprosy and found that the P-CTL population was greatly expanded in T-lep vs. L-lep states of infection (FIG. 2A, FIG. 2B). Because states of infection correlate with cytokine profiles (8), it was reasoned that the difference in percentage of P-CTLs found in T-lep as opposed to L-lep might be explained by the different cytokines expressed in those states. Literature search identified IL-15 to independently be reported to induce granulysin (20), perforin (21, 22) and granzyme B (22) expression in T cells, as well as be up regulated in T-lep as opposed to L-lep lesions (23). The effect of this cytokine on the P-CTL compartment was examined. Treatment of healthy donor PBMC with this cytokine induces ex-vivo expansion of P-CTLs (FIG. 2C, FIG. 2D). Because IL-15 has been shown to influence the CD8+ memory T cell compartment (24), other cytokines known to influence this compartment were examined. IL-2, and IL-7 like IL-15 induced expansion within the P-CTL compartment, however IL-10 and non-specific stimulation through the TCR with αCD3/28 micro beads did not cause an expansion within the P-CTL compartment (FIG. 3).

IL-15 causes selective proliferation of P-CTLs. Because IL-15 and IL-7 have been shown to induce proliferation in memory cells (24), these cytokines ability to induce proliferation specifically within the P-CTL subset was examined. To this end, PBMCs were labeled with CFSE and interrogated specific division by CFSE dilution within subpopulations of cytotoxic cells using flow cytometry. It was found that IL-15 (FIG. 4A), and IL-2 (not shown) induced specific proliferation within the P-CTL compartment over a 12-day time frame (FIG. 4B).

Figure 5A:
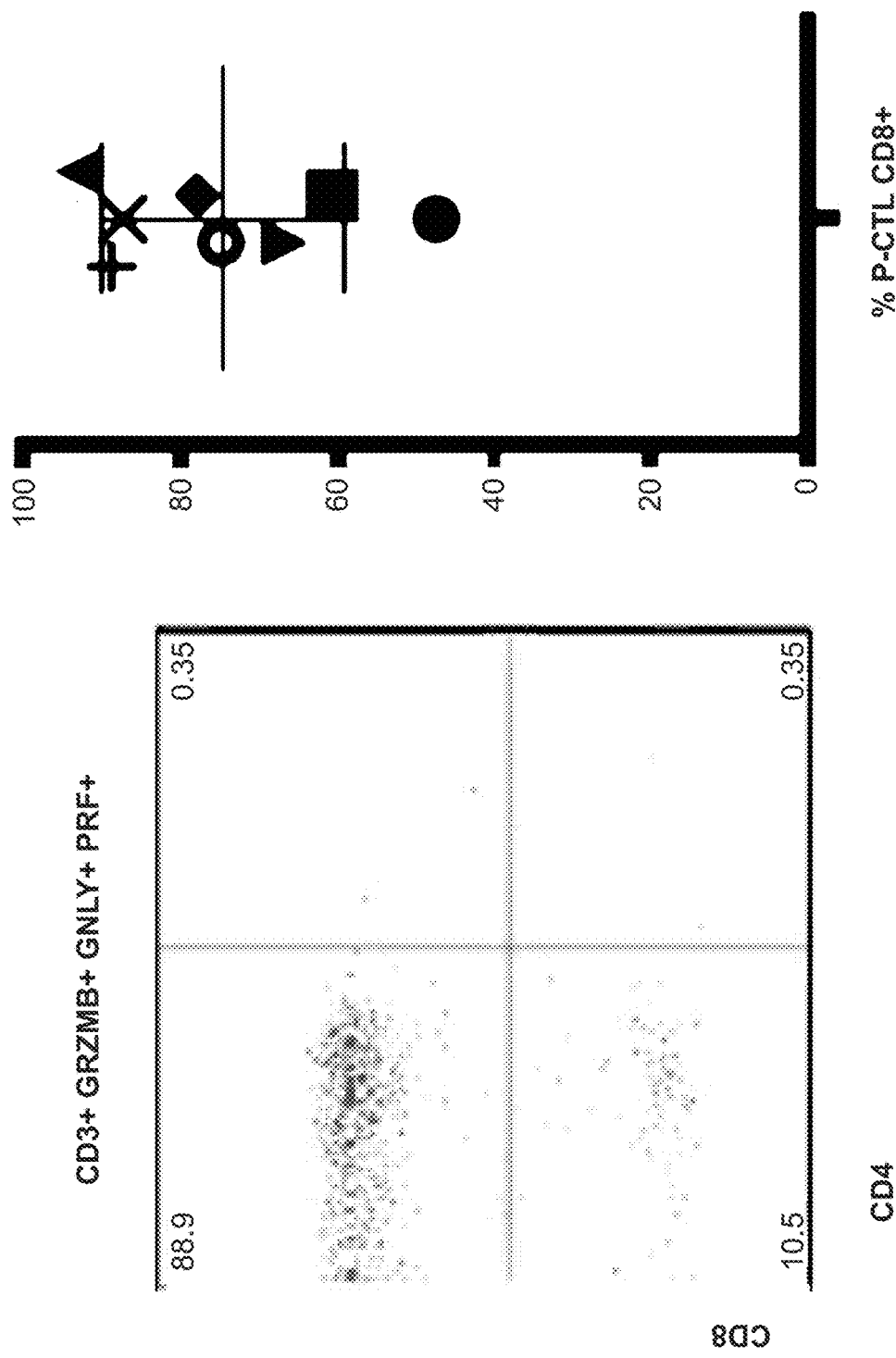
FIG. 5A: P-CTLs are $CD8^+$ $T_{EMRA}$ cells that constitutively express IL2Rβ and upregulate IL-15Rα with stimulation.
Figure 5B:
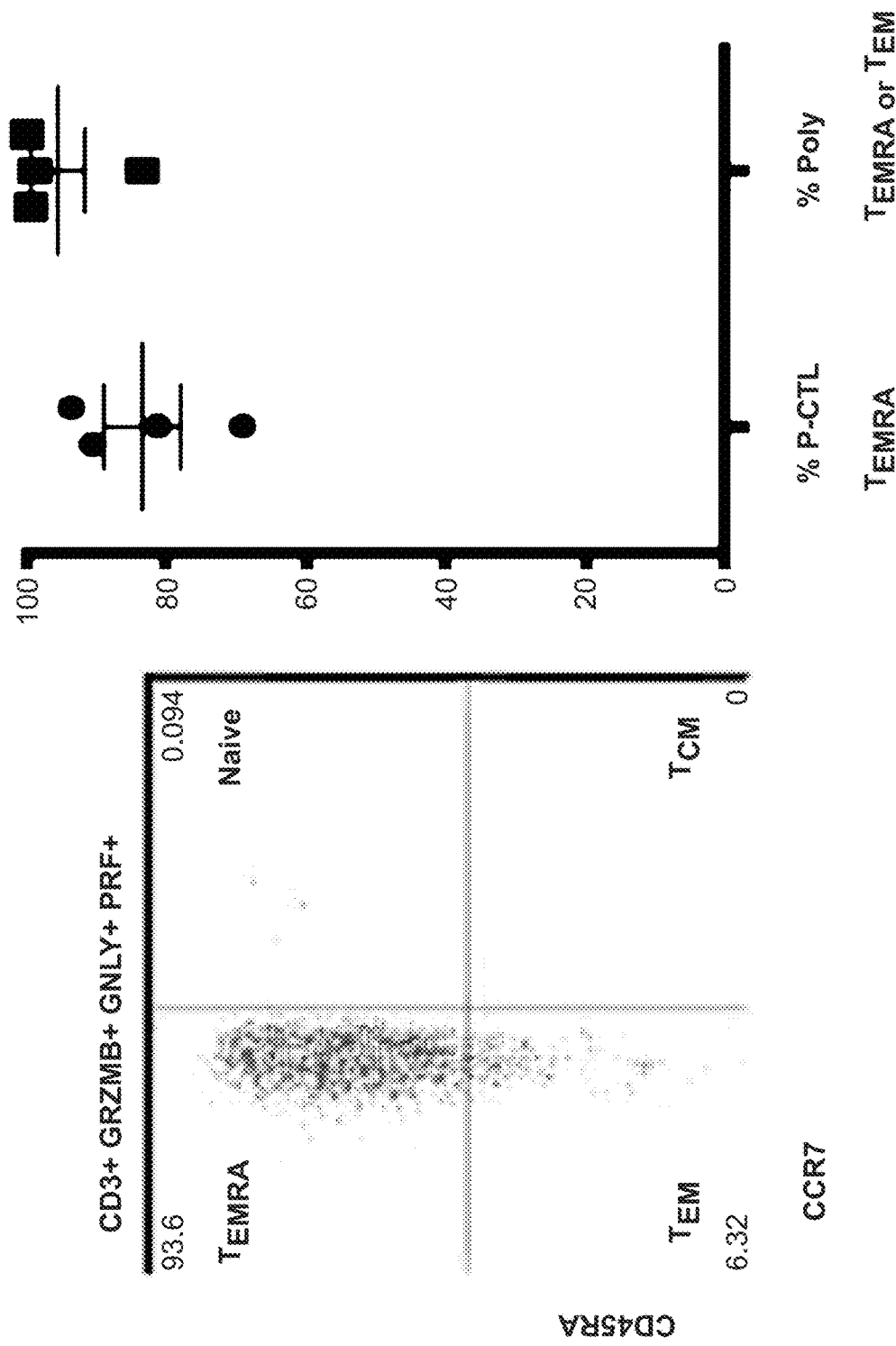
FIG. 5B: The P-CTL compartment was examined in multiple donors and found to consist primarily of $CD8^+$ $CCR7^-$ $CD45Ra^+$ ($T_{EMRA}$) cells.
Figure 5C:
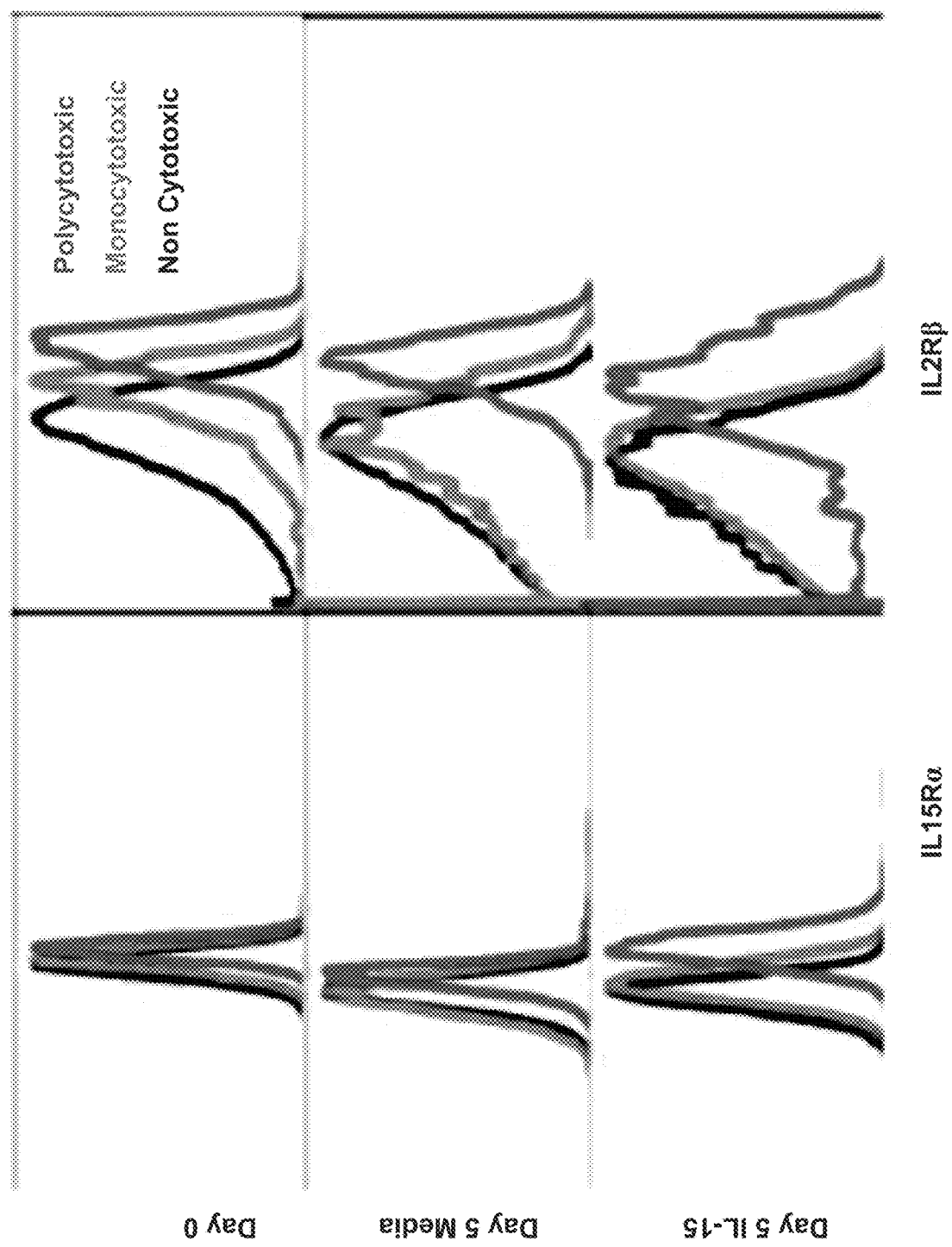
FIG. 5C: P-CTLs were found to constitutively express IL2Rβ and upregulate IL-15Rα with IL-15 stimulation after 5 days.

Phenotypic analysis of P-CTLs. In an effort to define the P-CTL compartment, these cells were phenotyped and find that they are primarily CD8$^+$ cells, (FIG. 5A). Additionally, collaborators have implicated P-CTLs as important in controlling infection of M. tuberculosis (25). Because it has been shown that treatment with infliximab leads to contractions of the CD8$^+$ T$_{EMRA}$ compartment correlating with an increased susceptibility towards infection with M. tuberculosis (1), and because it was shown that cytokines known to influence the memory compartment selectively expand the P-CTL compartment (FIG. 3, FIG. 4A, and FIG. 4B), it was hypothesized that P-CTLs are likely subsets of T$_{EMRA}$ cells. The P-CTL population was interrogated for CCR7 and CD45RA expression and found that indeed these cells almost exclusively are comprised of CCR7$^-$, CD45RA$^+$ T$_{EMRA}$ cells (FIG. 5B). Finally, because P-CTLs preferentially divided in response to IL-15, the expression of the components of the IL-15 receptor on these cells was examined. As expected, up regulation of the IL-15α receptor with stimulation on P-CTLs and constitutive expression of the IL-15β receptor on P-CTLs was found (FIG. 5C).

Figure 13A:
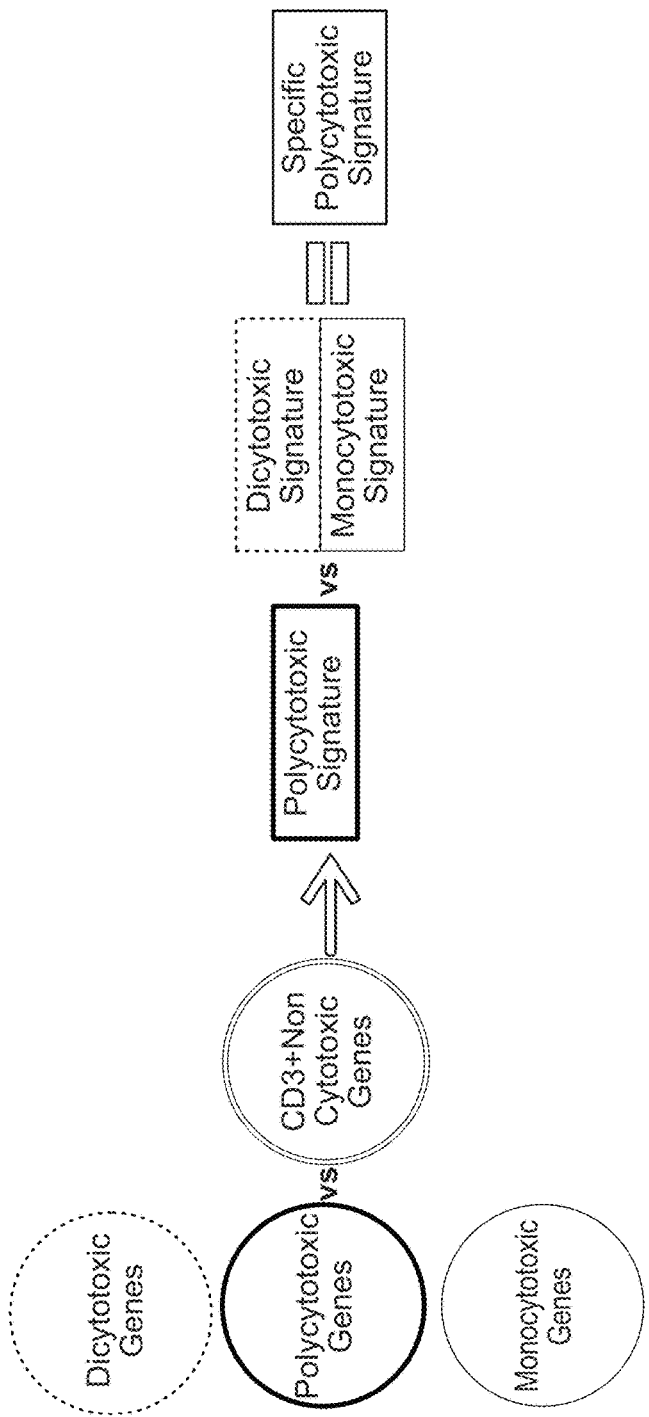
FIG. 13A: RNA sequencing of cytotoxic cell populations identifies NK pathways on P-CTLs. T cells were enriched from PBMCs and stained with CD3, granulysin, granzyme B and perforin. Fixed cells were sorted into populations of P-CTL, D-CTL, M-CTL, N-CTL cells. RNA was isolated from these cells and RNA sequencing performed. Genes signatures of P-CTL, M-CTL and D-CTL cells were created by selecting genes 2 fold up in each population over each other compared population except P-CTL to D-CTL which were 1.5 fold up.
Figure 13B:
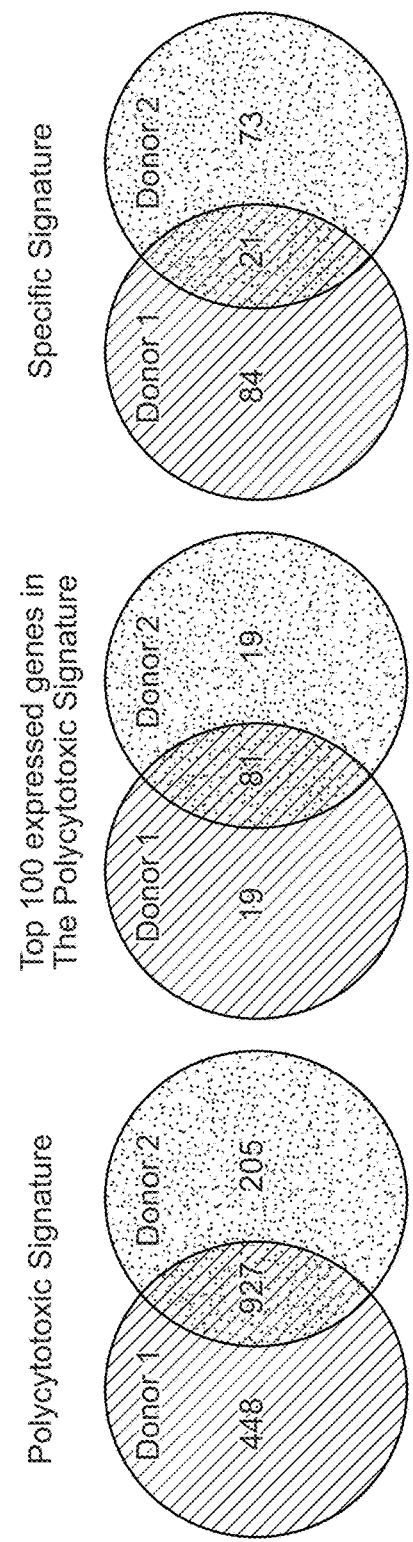
FIG. 13B: P-CTL gene signatures from two donors were compared using Venny. Oliveros, J. C. (2007-2015) *Venny. An interactive tool for comparing lists with Venn's diagrams.* http://bioinfogp.cnb.csic.es/tools/venny/index.html.

Identification of P-CTL surface markers by RNA sequencing. Initial methods identifying the P-CTL compartment required intracellular staining, which necessitated fixation and precluded functional studies. In an effort to circumvent this barrier, surface markers that may define the P-CTL population to permit sorting of live cells were identified. RNA sequencing was performed on fixed and sorted CTL subsets by using an adapted protocol for RNA isolation after PFA fixation (14). By transcriptome sequencing of P-CTL, D-CTL, M-CTL, and N-CTL populations, a specific P-CTL signature was generated in two donors as outlined (FIG. 13A). Analysis of two donors showed excellent overlap in P-CTL gene signatures (FIG. 13B), as well as excellent overlap between other cytotoxic subsets (not shown). In silica signature analysis using Ingenuity (Qiagen) unexpectedly identified "Natural Killer Cell signaling" and "Cross talk between Dendritic Cells and Natural Killer Cells" as the top 2 canonical pathways in the two donors analyzed (See FIG. 18).

Figure 6:
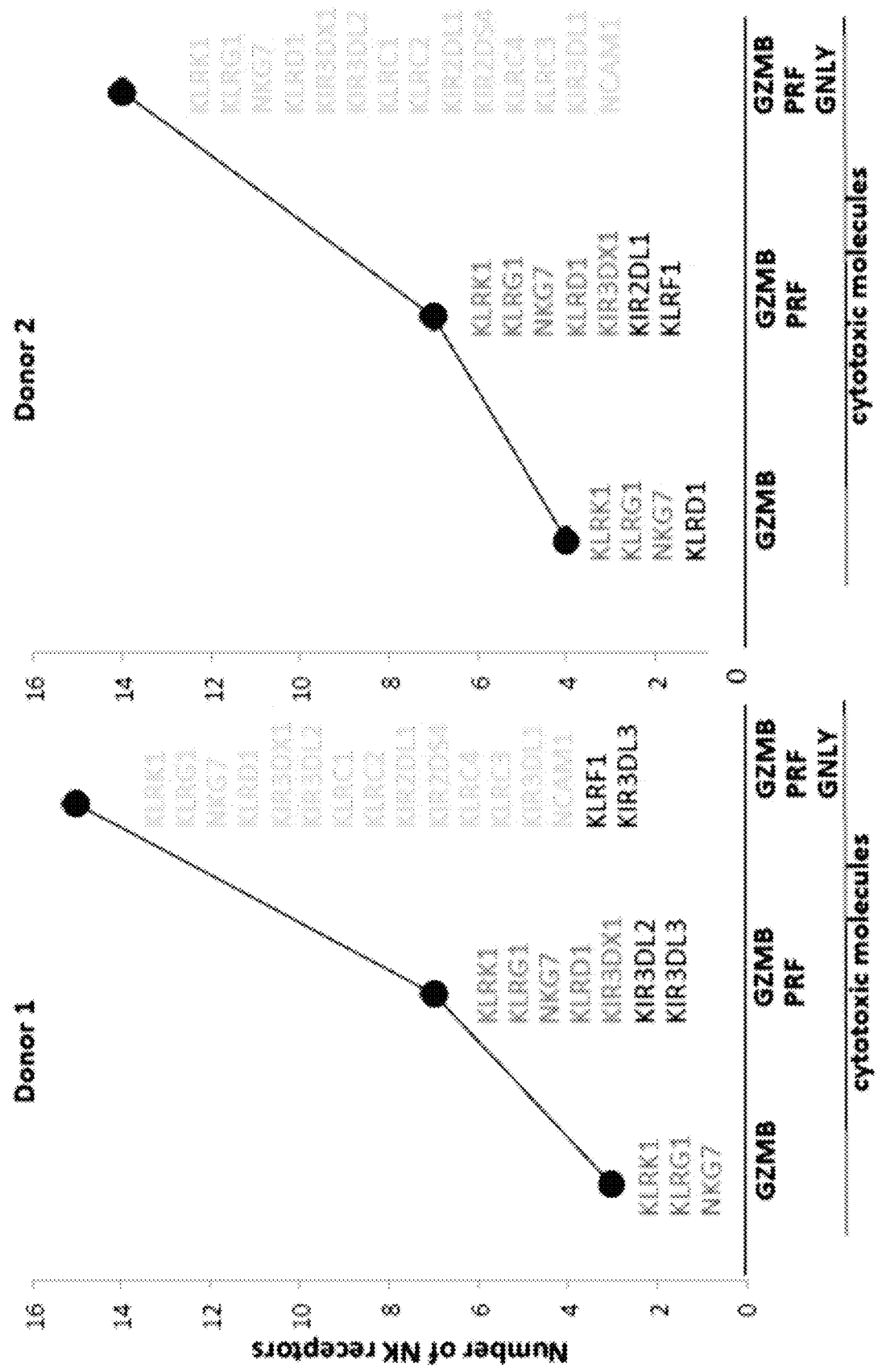
FIG. 6: The number of modulatory NK surface receptor is correlated with the number of cytotoxic molecules expressed. The number of surface NK receptors expressed in a population (y-axis) is graphed as a function of the number of cytotoxic molecules expressed by that population (x-axis). NK receptor expression by a population is defined by greater than 2 fold expression over each preceding population (or 1.5 fold for P-CTL vs D-CTL). Similar colors represent the similar NK receptors between donors.
Figure 14:
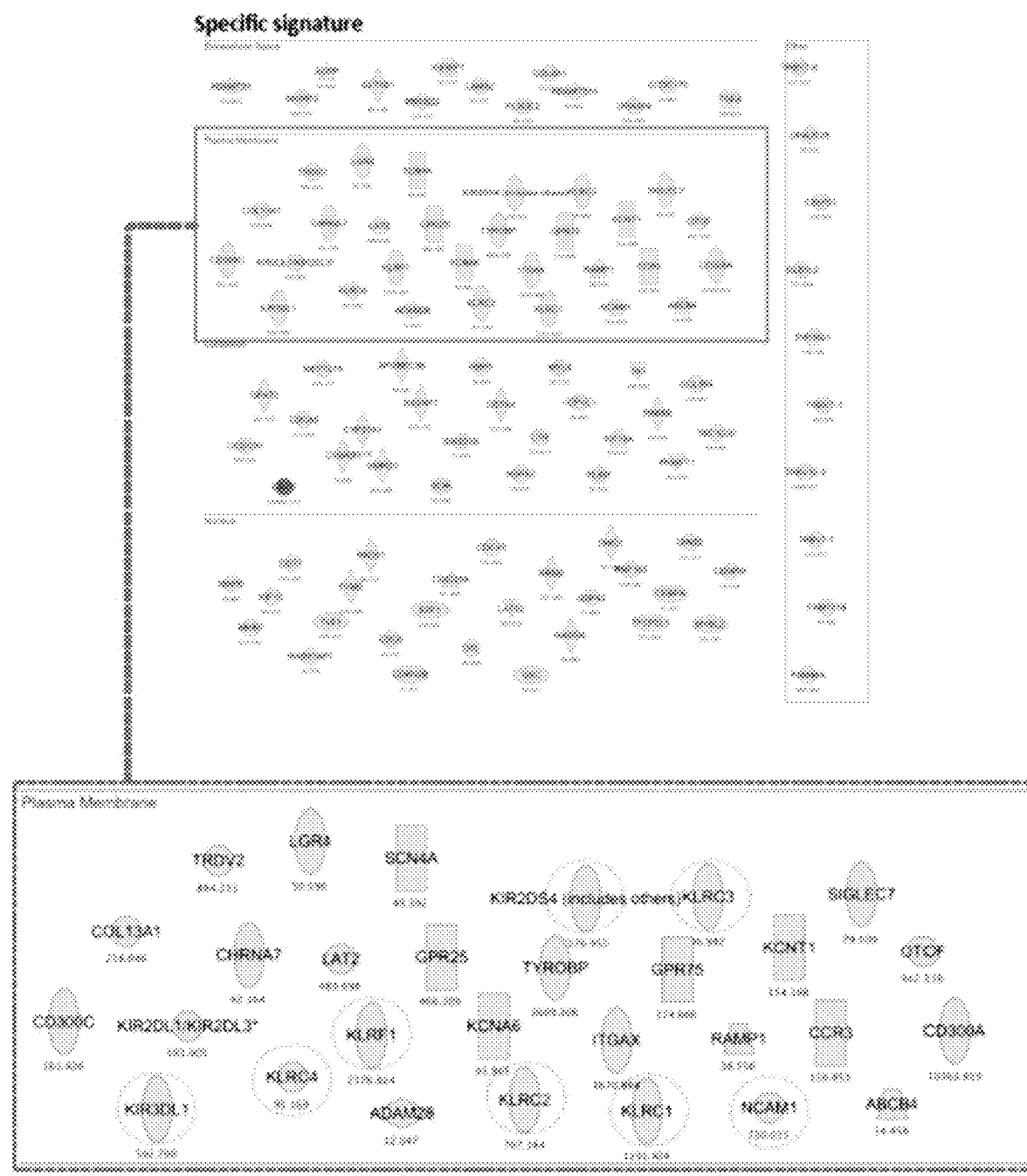
FIG. 14: Analysis of the P-CTL specific signature reveals an enrichment of NK surface modulatory receptors. Genes identified as specific to P-CTLs and comprising the P-CTL 'specific signature' were analyzed by Ingenuity (Qiagen) and sorted for surface expression (insert). NK receptors are circled.
Figure 15:
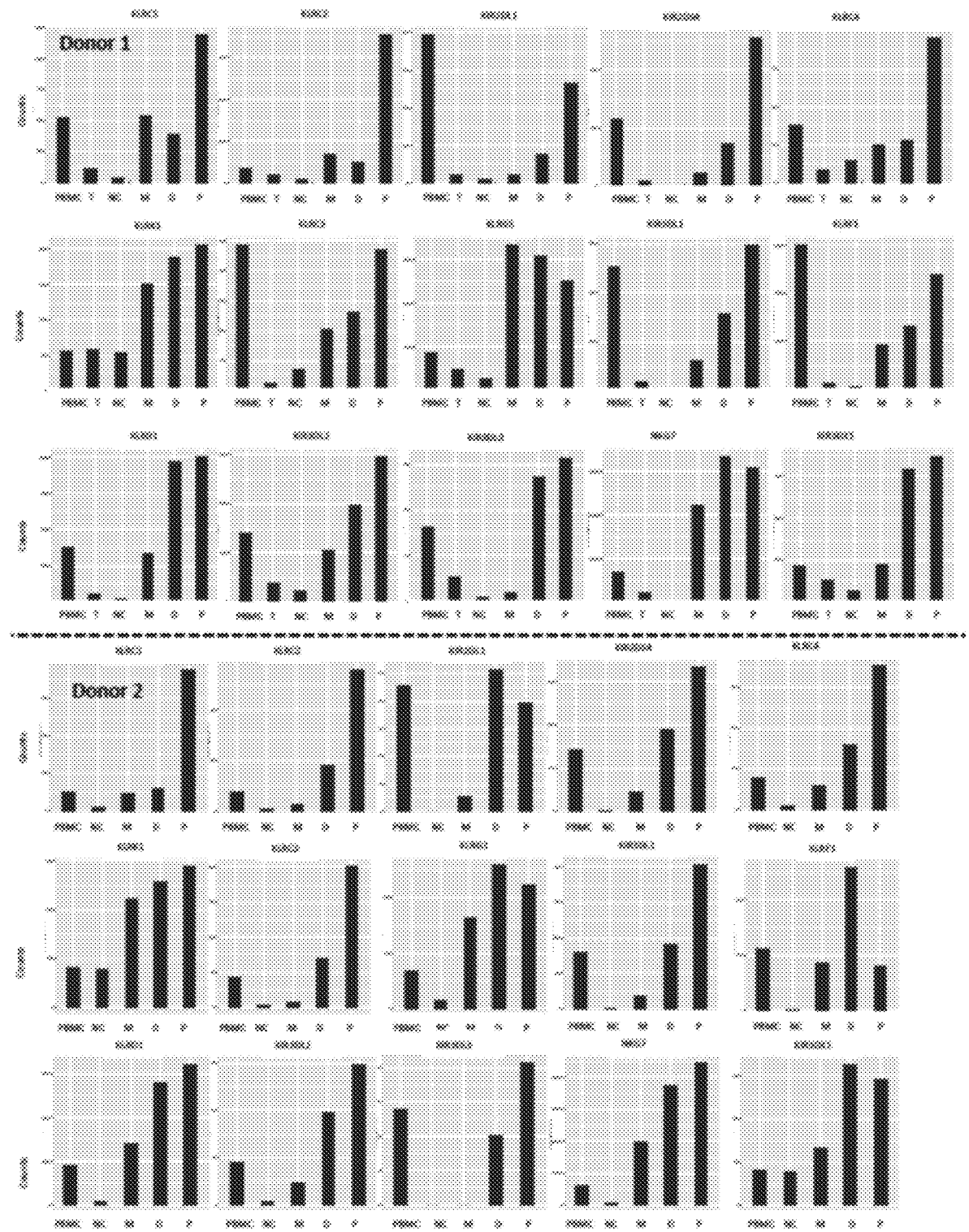
FIG. 15: Comparison of all identified NK receptors between cytotoxic cell populations. Relative counts of all identified NK cell receptors on P-CTL as compared with D-CTL, M-CTL, N-CTL and PBMCs reveal several receptors as potential candidates which mark the P-CTL population.

In keeping with canonical pathway analysis, sorting the P-CTL signature by surface expressed genes revealed numerous candidate surface markers, which strikingly include many modulatory NK receptors (FIG. 14). Importantly, there has been excellent corroboration of these markers between the two donors analyzed (FIG. 15). Analysis of surface NK receptors revealed the striking finding that modulator NK receptor expression correlated with cytotoxic molecule expression. Specifically, it was observed that as the number of cytotoxic molecules increased within a population, the number of modulatory NK receptors that population expressed also increased (FIG. 6), suggesting that as a population gains cytotoxic ability it gains more checks and balances to control function. Finally, to determine whether P-CTLs represent polyclonal or monoclonal populations, TCRs expressed by the population were examined between the two donors analyzed (See below). Primarily, αβ TCR combinations were represented within the P-CTL compartments, and it was found that these TCRs were different between the two donors. This suggests P-CTLs originate from a diverse CD8$^+$ T cell population.

| TCRs Expressed | |
|---|---|
| Donor 1 | Donor 2 |
| TRAV12-2 | TRGV1 |
| TRDV2 | TRBV5-3 |
| TRBV7-3 | TRBV6-6 |
| TRBV7-8 | TRAV10 |
| TRBV7-1 | TRAV21 |
| TRBV7-6 | TRAV24 |
| | TRAJ4 |
| | TRBV5-4 |
| | TRAV30 |

Figure 7:
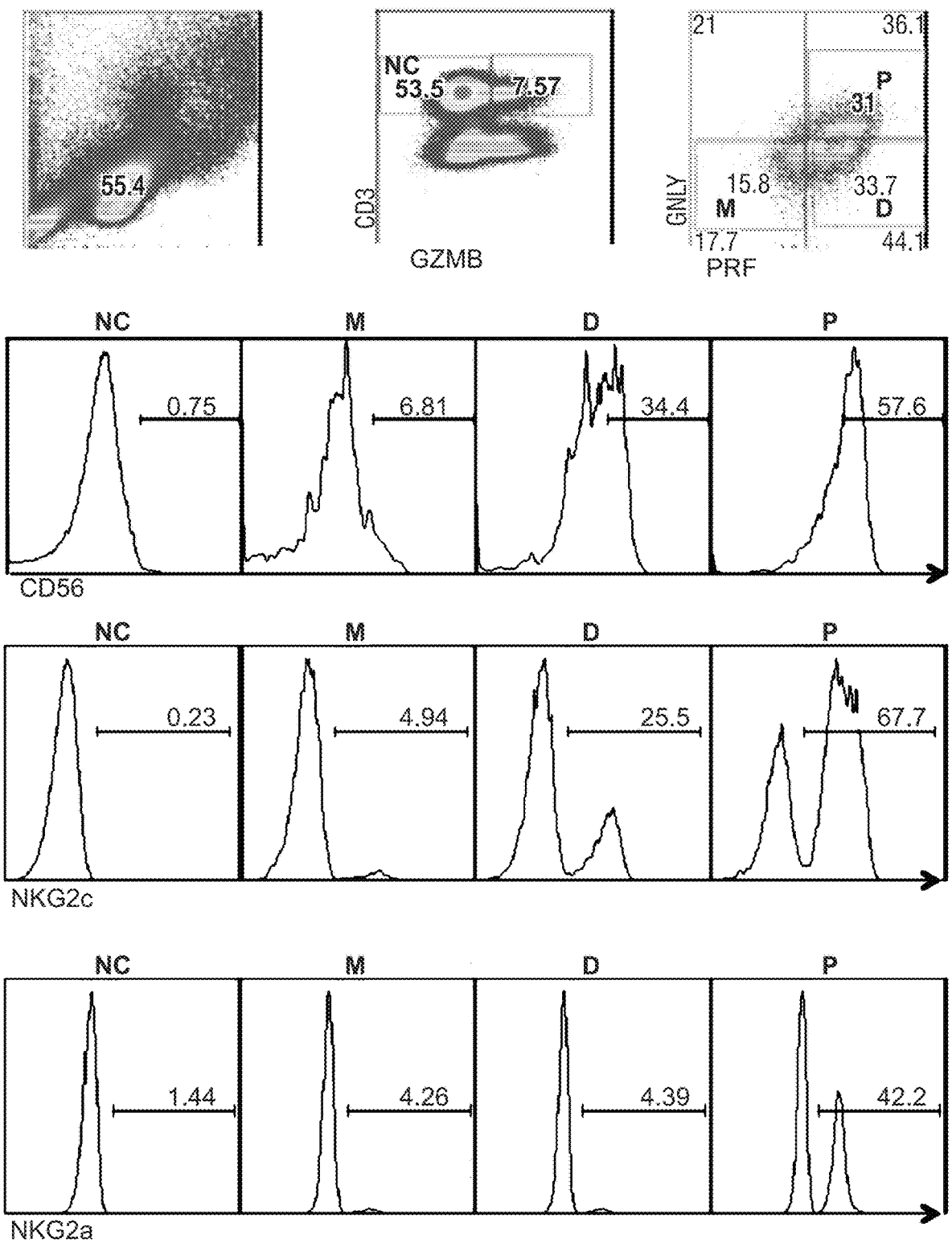
Figure 8:
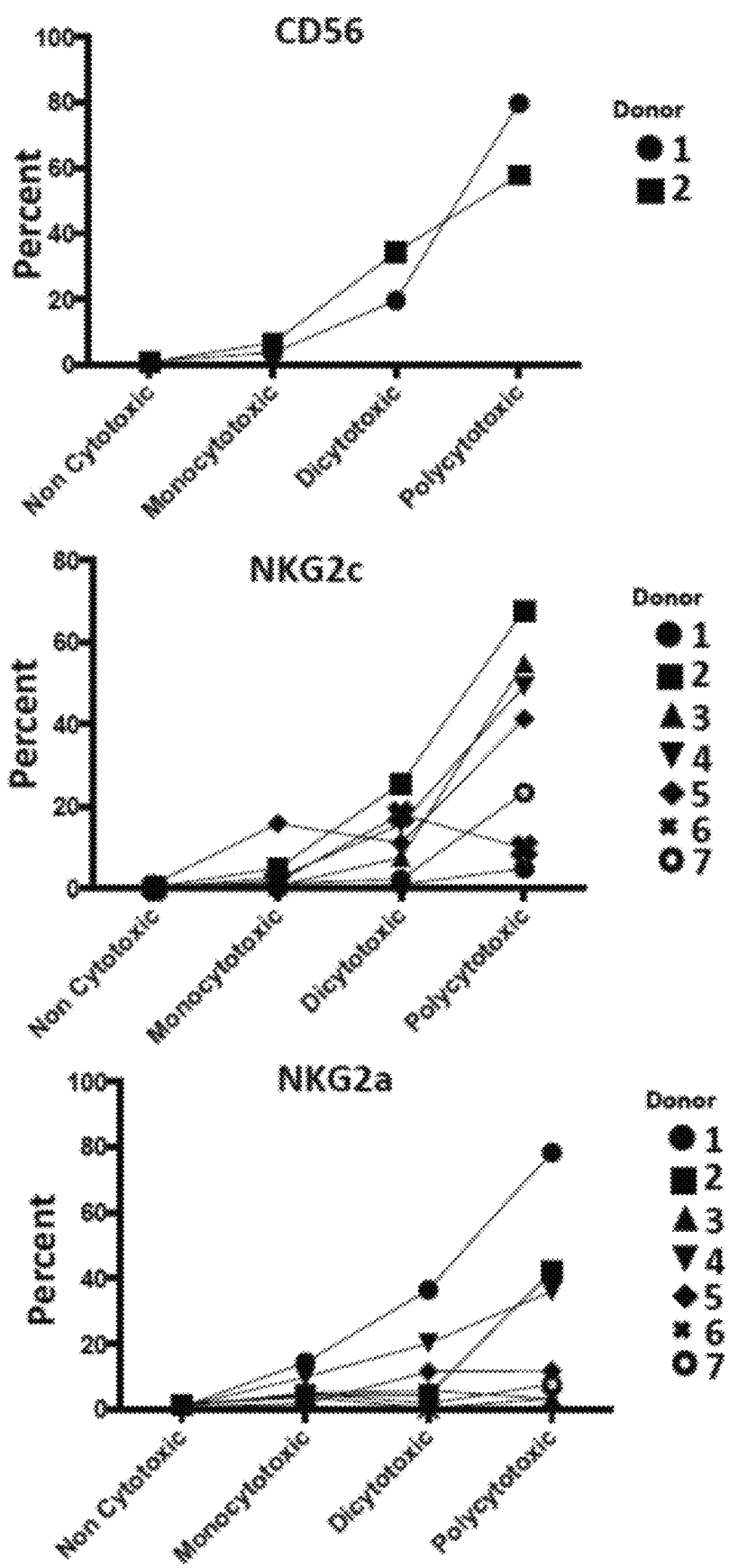
FIG. 8: CD56, NKG2c and NKG2a selectively mark P-CTLs. 7 donors (NKG2c, a) and 2 donors (CD56) were analyzed for the selected NK markers. The percent P-CTL, D-CTL, M-CTL and N-CTL cells expressing these markers in each respective donor is graphed. Lines between symbols delineate donors to facilitate observing the trend.
Figure 9A:
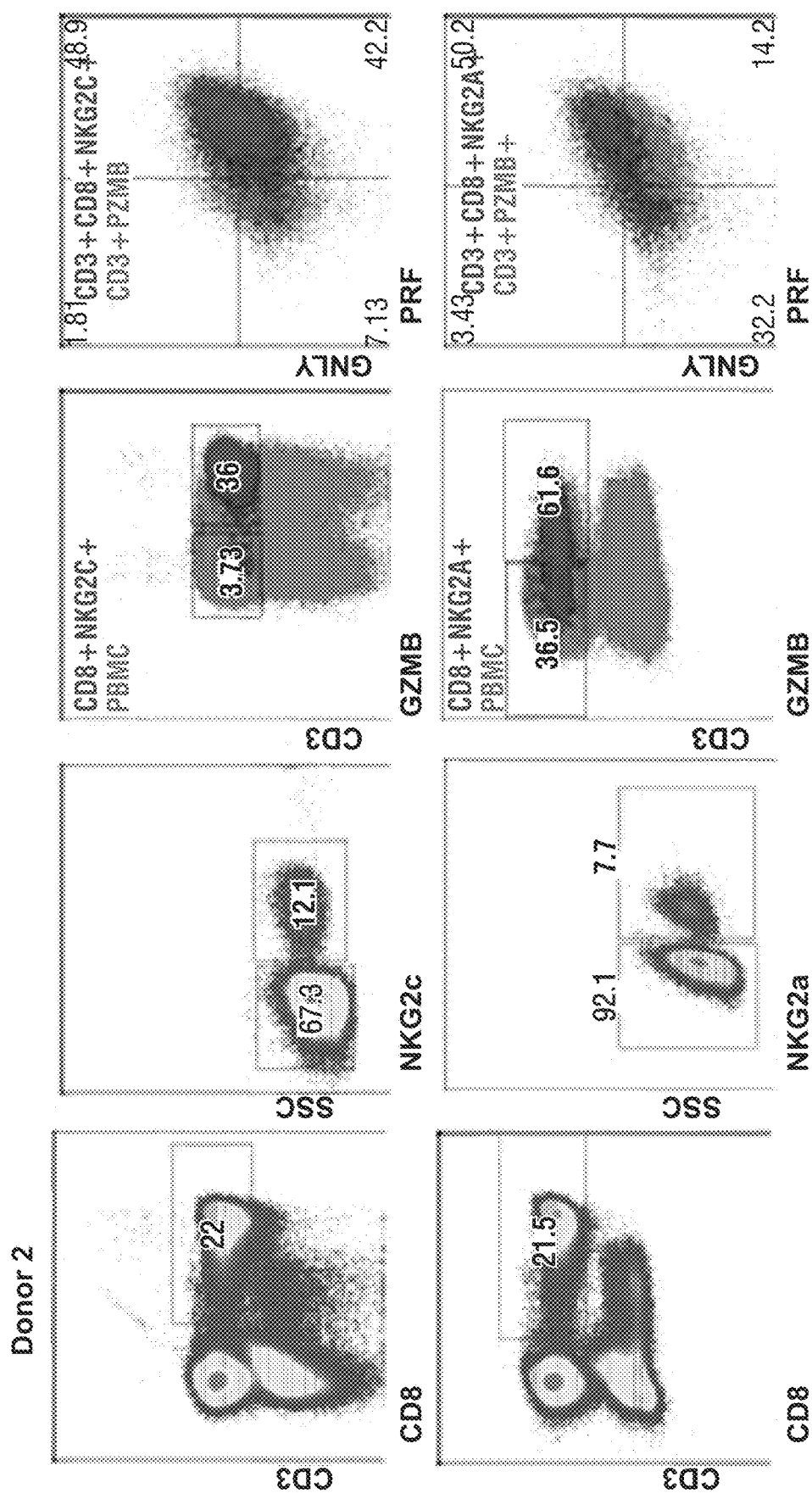
FIG. 9A: NKG2c and NKG2a specifically enrich for P-CTLs in $CD8^+$ T cells but sensitivity and specificity of the markers differ between donors. PBMCs were stained with CD3 and CD8 and double positive cells were interrogated for expression of either NKG2c or NKG2a. Cells were concomitantly stained with GZMB, PRF and GNLY, and $CD3^+$ $CD8^+$ and $NKG2c^+$ or $NKG2a^+$ Triple positive cells were back gated over either PBMCs looking at GZMB expression or over $CD3^+$ $GZMB^+$ cells looking at PRF and GNLY expression. To determine the percentage of P-CTLs within the CD8 population labeled by these NK surface markers.
Figure 9B:
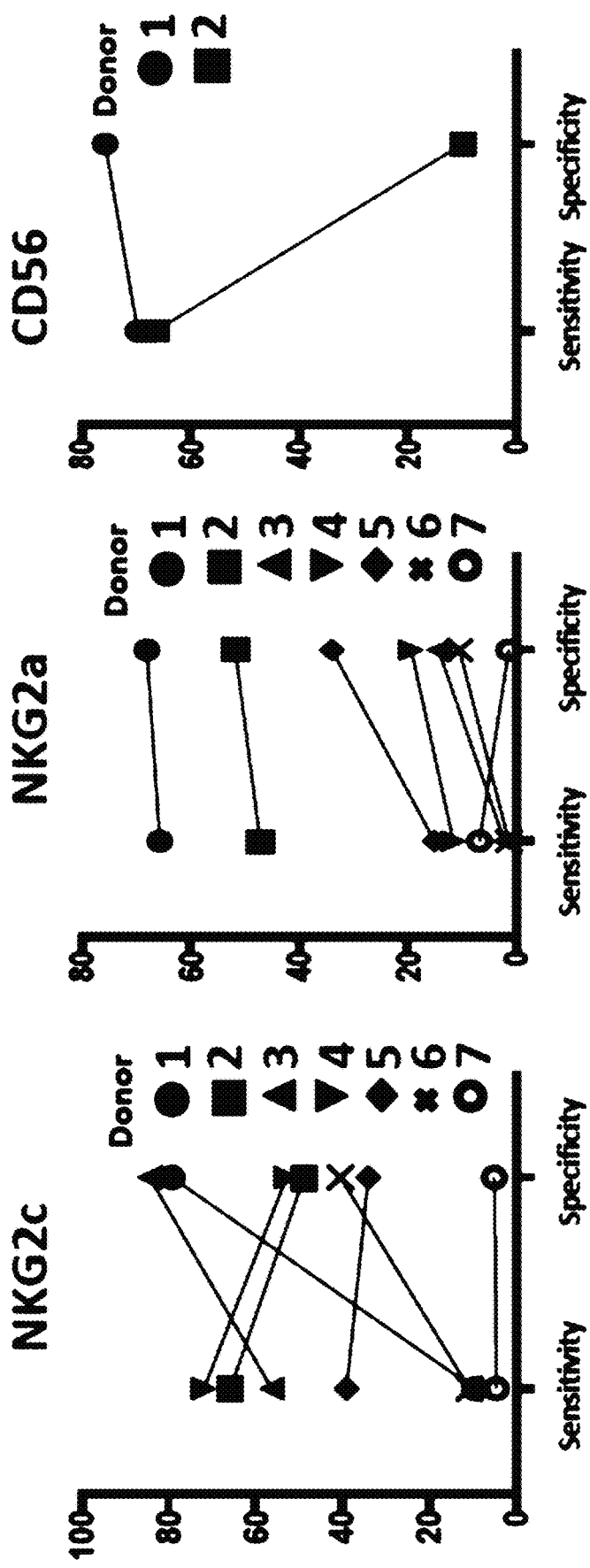
FIG. 9B: Results from "A" for multiple donors were used to calculate the sensitivity (% of CD8 Polys labeled by NKG2a) and specificity (% of CD3 CD8 NKG2a labeled cells that are Polys) of these surface NK markers.

Confirmation of NK cell surface marker expression on P-CTL. Expression of several modulatory NK receptors on P-CTLs from several donors were validated. It was found that KLRC1 (NKG2a) and KLRC2 (NKG2c) as well as NCAM1 (CD56) to be specifically enriched on the P-CTL population (FIG. 7) and examined expression of these surface markers across multiple healthy donors to establish a statistically significant trend (FIG. 8 and FIG. 16). It was next confirmed that NKG2a and NKG2c could be used to sort the P-CTL population. To this end, it was found that NKG2c marked P-CTL and D-CTL cells while, NKG2a marked P-CTL cells and N-CTL cells (FIG. 9A). Several donors were screened and found that while in almost every case NKG2a and NKG2c were enriched on the P-CTL compartment over other compartments (FIG. 7, FIG. 8, and FIG. 9B) the sensitivity and specificity of these markers labeling the P-CTL compartment differed between donors (FIG. 9B). For further functional studies donors were chosen in which sorting on these markers provided a high enough yield to permit testing.

Figure 10:
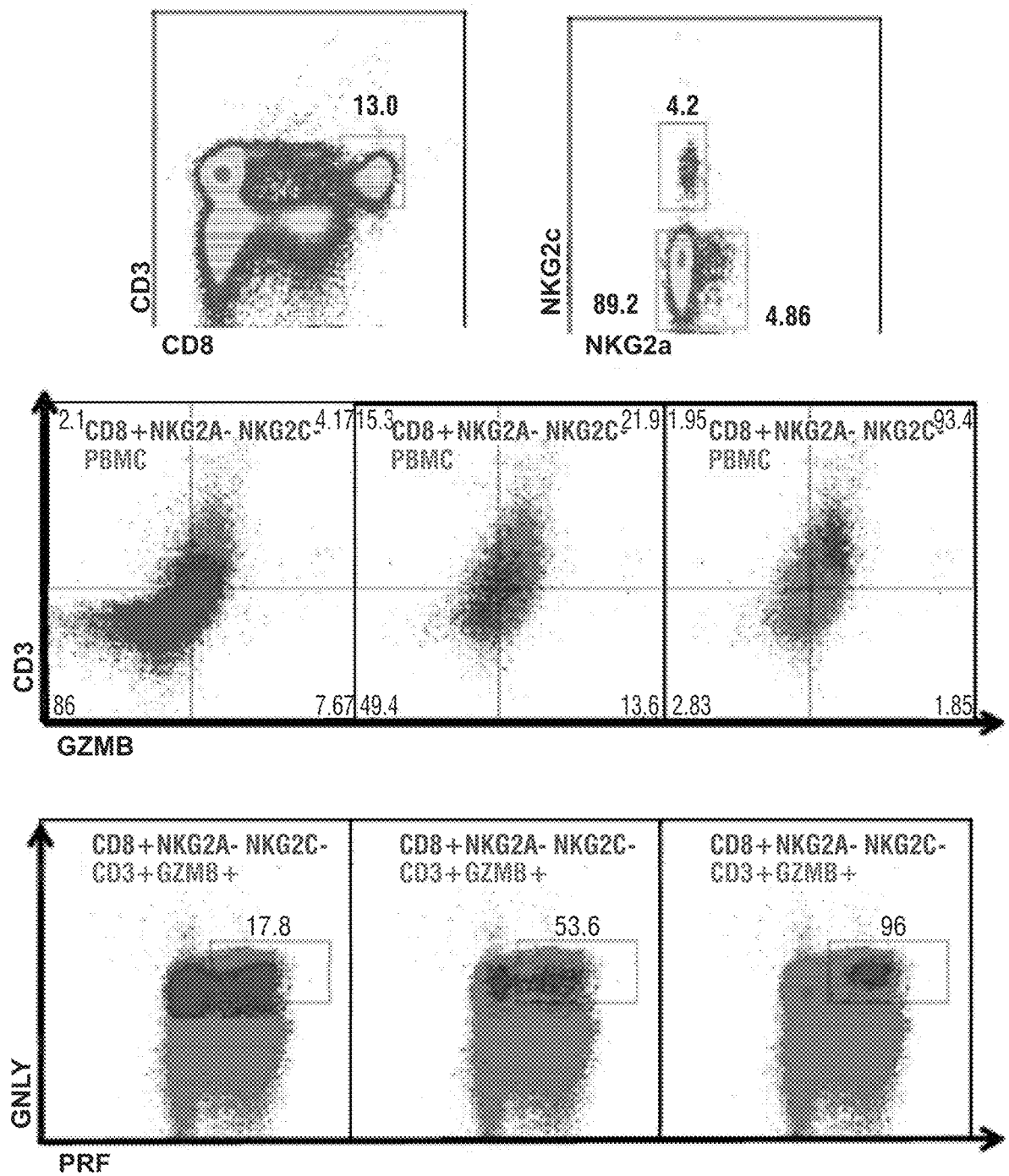
FIG. 10: NKG2c and NKG2a permit effective sorting of live P-CTLs. PBMCs were stained with CD3, CD8, NKG2c and NKG2a and sorted based on surface staining. P-CTLs were effectively enriched from populations of these cells based on the staining pattern shown and subsequently used for functional assays.
Figure 17A:
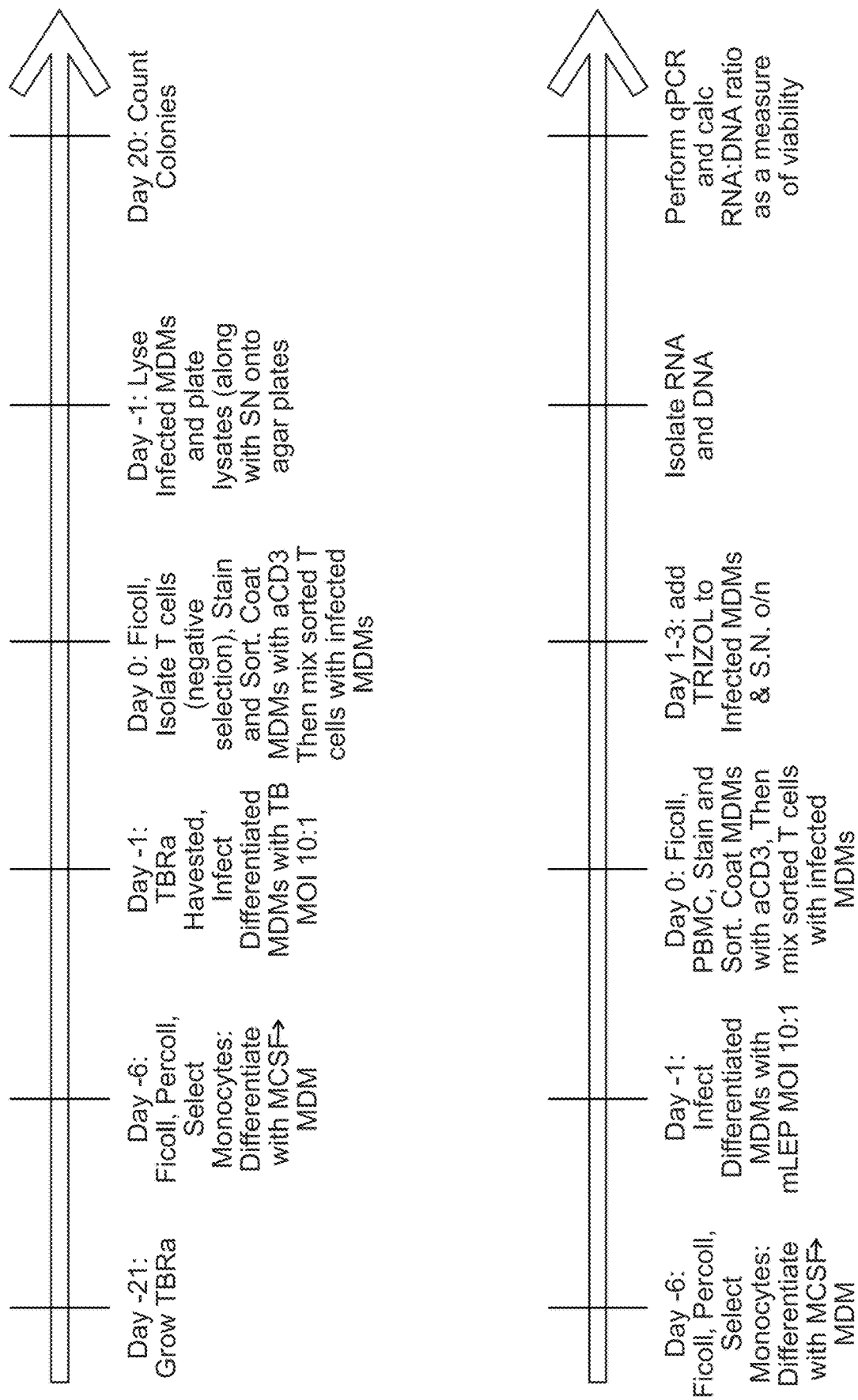
FIG. 17A: Outline of experiments showing P-CTL cells kill intracellular mycobacteria more efficiently than other $CD8^+$ subsets.

P-CTL cells kill intracellular mycobacteria more efficiently than other CD8$^+$ subsets. To determine whether P-CTL cells kill intracellular bacteria more efficiently than other CTL subsets P-CTL were sorted cells from other CD8$^+$ cells using markers for CD3, CD8, NKG2a and NKG2c, (FIG. 10) and admixed these sorted cells with infected M-CSF derived MDM cells coated with αCD3 used as targets as outlined in FIG. 17A. After 24 hours we measured bacterial viability. Killing was tested against both M. tuberculosis and M. leprae as outlined in FIG. 17A.

Figure 17B:
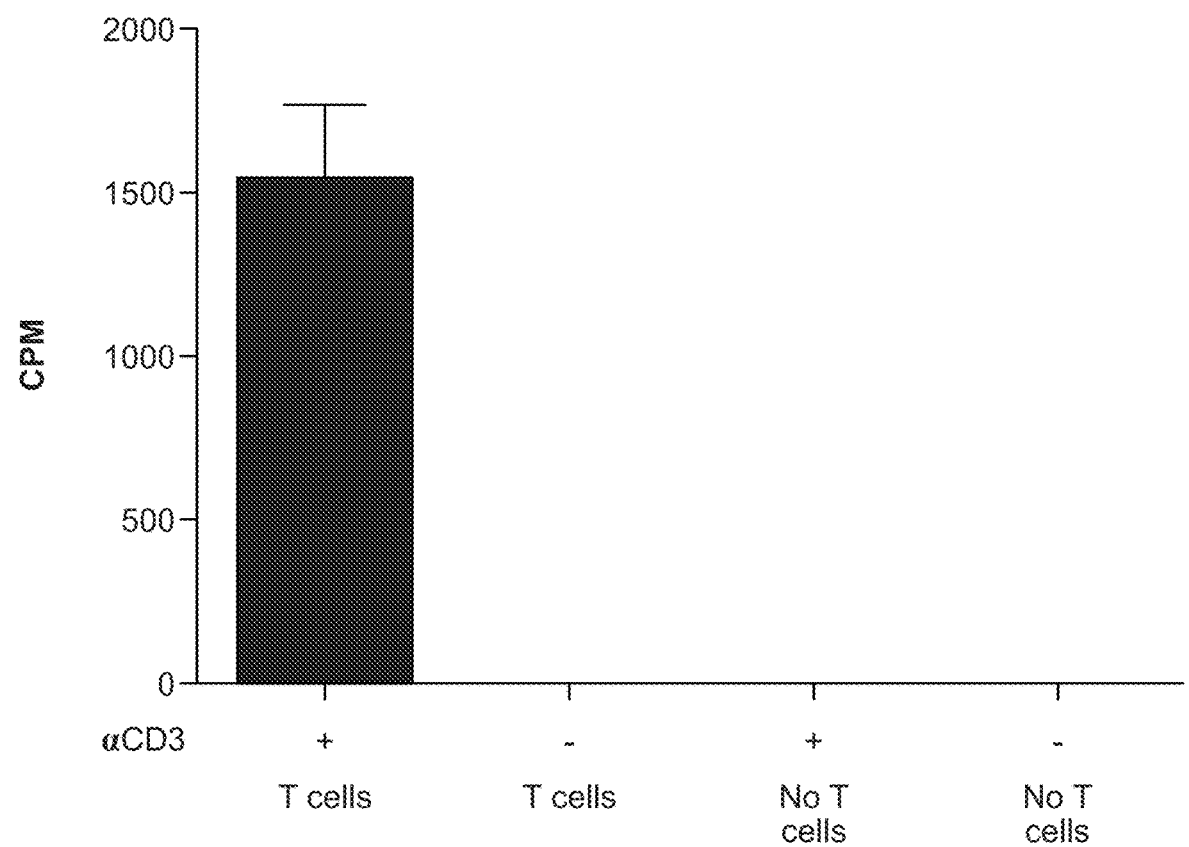
FIG. 17B: T cells were admixed with differentiated MDMs either coated or not coated with αCD3. $^3H$-thymidine was used to determine proliferation of cells after 88 hours of growth with pulsing for the final 16 hours.

Because specificity of sorted P-CTLs was diverse αCD3 was used to coat target cells to ensure reactivity. Coated MDMs elicited robust responses from T cells (FIG. 17B). Results clearly demonstrate that as the percentage of P-CTL cells increase in culture with targets, the percentage killing of bacteria also increases (FIG. 11A, and FIG. 11B), this is true for both M. leprae (FIG. 11A), and M. tuberculosis (FIG. 11B). Additionally, killing is contingent upon P-CTL activation because uncoated MDMs exhibited baseline killing (FIG. 11C and FIG. 11D). Together the results show that P-CTLs are more efficient at killing than other CD8$^+$ T cells.

The P-CTL signature is enriched in Steven-Johnson syndrome (SJS) and Toxic Epidermal Necrolysis (TEN). Multiple lines of evidence point to a role for P-CTLs in SJS/TEN. First, recent studies have suggested anti TNFα therapy as an emerging treatment for SJS/TEN (26). Second, it is known that anti TNFα therapy leads to a decrease of $T_{EMRA}$ cells and this population contains P-CTLs. Third, other independent studies have implicated granulysin, perforin and granzyme B as playing a pathogenic role in the development of SJS/TEN (27). Fourth and finally, modulatory NK receptors have been identified on isolated CD8+ T cells from blister fluid of patients with SJS/TEN (28). Together this implicates the P-CTL compartment as mediating a role in TEN. This possibility was investigated by in-silica analysis using DermDB (ref) and indeed show that the P-CTL signature is enriched in the SJS/TEN signature (FIG. 12A and FIG. 12B). As expected, this strongly implicates a role for P-CTLs in the disease process of SJS/TEN.

Discussion

Although CD8+ CTLs have been studied as a single population, the data disclosed herein provide evidence that these CTLs are heterogeneous, differing by their expression of GZMB, PRF, and GNLY. To date heterogeneity within the cytotoxic T cell compartment is not well studied. But recent studies suggest that the cytotoxic molecules GZMB, PRF and GNLY act in concert to control infection (2, 3) and a cytotoxic T cell subset expressing all three molecules (P-CTL) may be important in controlling intracellular infection to M. tuberculosis (25). That the cytotoxic molecule GNLY is not expressed in mice (5, 29) likely adds to the under appreciation of this molecule in host defense in general and particularly of the subsets of cytotoxic cells in which it may be expressed.

The data indicate that P-CTLs, are the cells responsible for mediating the protective effect against intracellular bacterium. It was found that these cells are a subset of $T_{EMRA}$ cells controlled by IL-15, IL-7, and IL-2. These cells are shown directly kill intracellular bacterium better than other CD8+ T-cells. Additionally, it was found that subsets of cytotoxic T cells can be distinguished by the expression pattern of surface modulatory NK receptors. The finding that the number of these modulatory receptors is correlated with cytotoxic potential of a population has far reaching implications. It is reasonable to hypothesize that multiple checks and balances have evolved to help curtail the immune function of dangerous subsets of cytotoxic cells. The data suggests that this control not only comes in the form of TCR antigen recognition, but also may come with modulation of the signal through activating and inhibitory NK receptors. Of note, previous studies have implicated several of these NK receptors to be functional (18, 30-32), however whether these receptors are functional on P-CTLs, and whether they may signal independently of the TCR-antigen complex remains to be determined. Importantly, the association of P-CTL with host defense in leprosy and tuberculosis (4) suggests that a combination of their cell surface receptors could be used as biomarkers to monitor protective immunity in vaccine trails.

P-CTLs may be cells that not only mediate protection against intracellular pathogens, but also which directly cause the tissue injury seen in SJS/TEN. Multiple lines of evidence support this hypothesis and point to a role for P-CTLs in SJS/TEN. A strong association between the gene signatures for P-CTLs with the gene signatures for SJS/TEN is shown herein. Second, recent studies have suggested anti TNFα therapy as an emerging treatment for SJS/TEN (26) and it is known that anti TNFα therapy leads to a decrease of $T_{EMRA}$ cells (1), which contains the P-CTLs. Third, other studies have implicated granulysin, perforin and granzyme B as playing a pathogenic role in the development of SJS/TEN (27). Fourth and finally, modulatory NK receptors have been identified on isolated CD8+ T cells from blister fluid of patients with SJS/TEN (28). Together this suggests a strong association at least between the disease and the P-CTLs and opens the door for new possible therapies directed at these cells towards the goal of shutting down the aberrant immune responses seen in SJS/TEN.

Together these findings raise many possibilities for application and therapy development. NK surface markers on cytotoxic subsets may be used as biomarkers for protective immunity against bacterial and/or parasitic infection. Modulation of these biomarkers may provide possible vaccine targets. The finding that P-CTLs are influenced by cytokines raises the possibility that these cells may be directed to expand or contract through manipulation and the cytokine milieu. It may be possible to develop immune mediated therapies combating intracellular infection through selective expansion of this compartment by stimulation with IL-15 for example. Conversely therapy towards TEN/SJS or other inflammatory conditions may be approached through inhibiting IL-15 or other cytokines, causing a contraction in the P-CTL compartment. Furthermore, cytotoxic cells and the surface markers (particularly NK) which mark them may provide numerous receptors for targeted blockade in drug reactions. SJS/TEN may be treated, for example, through targeted depletion of the P-CTL more specifically than Infliximab or Etanercept subset with complement fixing antibodies that may target NKG2a, NKG2c or CD94 (the common signaling molecule between the two). Modulation of these cells may be beneficial in cancer immunotherapy. For example, selectively expanding populations of cytotoxic T cells, particularly the P-CTL population, may allow for targeted treatment of melanoma or other cancers that have been previously shown to respond to immune therapy. Finally, it has also been shown that GZMB, PRF and GNLY may act in concert to kill extracellular bacteria such as E. coli in certain model systems including (2). Given this it may be feasible that P-CTLs contribute to extracellular host defense as well as intracellular host defense. Therefore, P-CTLs may be viable therapeutic targets for modulation in order to facilitate extracellular bacterial clearance. Treatments may center around stimulation of these cells and would therefore bypass the problem of development of antibiotic resistance.

The gene expression profiles for polycytotoxic T cells were compared to the gene expression profiles for all CD3+ T cells. The following genes were upregulated in polycytotoxic T cells relative to CD3+ T cells, wherein the first number in parentheses corresponds to the expression level, the second number corresponds to the fold-change for polycytotoxic T cells relative to all CD3+ T cells, and the third number corresponds to the p-value: GZMB (11597; 13.5; 0.00), NME8 (343; 13.1; 0.02), FCGR2C (194; 12.3; 0.04), GPR141 (130; 11.7; 0.02), FCGR3A (6755; 11.1; 0.00), GPR97 (61; 10.6; 0.04), SGCD (60; 10.6; 0.04), CCL4L1 (51; 10.4; 0.04), ISL2 (49; 10.3; 0.04), FGFBP2 (9047; 10.3; 0.00), SORCS2 (42; 10.1; 0.05), KIR2DL1 (39; 10.0; 0.06), RAB38 (37; 9.9; 0.05), LILRB5 (37; 9.9; 0.06), SLC1A7 (915; 9.8; 0.01), GZMH (25043; 9.7; 0.00), GPR56 (25448; 9.3; 0.00), FCGR3B (24; 9.3; 0.09), CD300LB (22; 9.2; 0.16), CMKLR1 (2812; 9.1; 0.00), CX3CR1 (8260; 9.1; 0.00), LGALS9B (20; 9.0; 0.08), KIR2DL3 (531; 9.0; 0.00), TYROBP (2572; 9.0; 0.01), GNLY (193248; 8.9; 0.00), KIR3DL1 (407; 8.6; 0.00), SIGLEC7 (14; 8.6; 0.18), GLT1D1 (13; 8.5; 0.18), HBA1 (10; 8.1; 0.27), TFCP2L1 (1239; 7.9; 0.02), CXCR1 (223; 7.8; 0.01), B3GAT1 (4593; 7.6; 0.01), MAFB (7; 7.6; 0.28), PDGFRB (1268; 7.5; 0.02), KIR2DS4 (334; 7.3; 0.00), ASCL2 (1500; 7.3; 0.00), FGR (12319; 7.3; 0.00), SETBP1 (763; 7.2; 0.00), NUAK1 (152;

7.2; 0.01), TRDV2 (148; 7.2; 0.00), FAM20C (5; 7.1; 0.21), LILRA1 (5; 7.1; 0.32), LYN (822; 7.1; 0.03), TMCC3 (400; 7.0; 0.00), LILRB1 (3193; 7.0; 0.00), C1orf21 (2805; 6.9; 0.00), MLC1 (491; 6.9; 0.00), LRRC16B (1215; 6.9; 0.00), PODN (451; 6.8; 0.00), EMR3 (4; 6.8; 0.39), LILRA3 (4; 6.8; 0.34), KLRC2 (557; 6.8; 0.00), TRGV2 (439; 6.7; 0.00), PCDH1 (211; 6.7; 0.01), CCL4 (2112; 6.6; 0.00), S1PR5 (6198; 6.5; 0.00), NKG7 (44305; 6.5; 0.01), NMUR1 (2832; 6.4; 0.00), SH3RF1 (3; 6.4; 0.31), SLCO4C1 (575; 6.3; 0.00), CLDND2 (3688; 6.1; 0.00), NCR1 (577; 6.1; 0.00), ZNF683 (14293; 6.1; 0.03), PRSS23 (2880; 6.1; 0.00), NCAM1 (765; 6.1; 0.01), KLRC3 (200; 6.0; 0.01), C19orf35 (130; 6.0; 0.01), ZEB2 (3311; 5.8; 0.00), ITGAM (12128; 5.8; 0.00), GSC (58; 5.8; 0.02), NCS1 (58; 5.8; 0.02), GPR153 (972; 5.8; 0.00), QPCT (2; 5.8; 0.47), CYP1B1 (2; 5.8; 0.47), FAM49A (505; 5.8; 0.00), RCAN2 (107; 5.7; 0.01), FCRL6 (9905; 5.6; 0.00), TRGJP2 (51; 5.6; 0.03), KLRF1 (403; 5.6; 0.01), PIK3AP1 (1095; 5.5; 0.00), RASSF4 (1141; 5.5; 0.04), KLRD1 (6448; 5.5; 0.00), FCGR2A (228; 5.5; 0.12), ITGAX (5332; 5.5; 0.05), PROK2 (262; 5.4; 0.01), TBX21 (14226; 5.3; 0.00), KLRC1 (1121; 5.3; 0.01), PDGFD (279; 5.3; 0.01), CCL3 (316; 5.3; 0.00), TRGV9 (354; 5.3; 0.00), SPRY2 (39; 5.3; 0.04), SPON2 (11004; 5.2; 0.00), MGAM (37; 5.2; 0.04), KIR3DL2 (148; 5.2; 0.01), TM6SF1 (36; 5.1; 0.14), MYOM2 (10647; 5.1; 0.01), HHEX (71; 5.1; 0.17), PRF1 (37013; 5.1; 0.00), MYO3B (177; 5.1; 0.01), CTBP2 (318; 5.1; 0.02), KLRC4 (176; 5.1; 0.01), SH2D1B (35; 5.1; 0.23), GAS7 (3488; 5.1; 0.00), TMEM255A (69; 5.1; 0.02), ATP8B4 (69; 5.1; 0.06), LRFN2 (34; 5.0; 0.07), BTBD17 (67; 5.0; 0.03), LGR6 (1863; 5.0; 0.01), ARHGEF28 (163; 5.0; 0.02), COLGALT2 (585; 5.0; 0.01), IL7 (63; 4.9; 0.03), CD244 (2988; 4.9; 0.00), CST7 (13751; 4.9; 0.00), HSPA6 (147; 4.8; 0.04), RGS9 (1376; 4.8; 0.01), EFNA5 (203; 4.8; 0.02), KIFC3 (435; 4.8; 0.01), NGFR (86; 4.8; 0.02), HCAR3 (1; 4.8; 0.50), IGLC2 (1; 4.8; 0.46), ZNF503 (1; 4.8; 0.44), PLA2G7 (1; 4.8; 0.45), FZD1 (1; 4.8; 0.55), VNN1 (1; 4.8; 0.55), FOLR3 (1; 4.8; 0.55), CLEC10A (1; 4.8; 0.55), CD1D (1; 4.8; 0.55), CLEC12B (1; 4.8; 0.51), PPBP (1; 4.8; 0.55), IGHG1 (1; 4.8; 0.55), CD86 (1; 4.8; 0.55), TTC38 (4663; 4.8; 0.01), ADRB1 (337; 4.8; 0.02), GPR114 (4098; 4.7; 0.00), C1orf177 (135; 4.7; 0.03), CST3 (418; 4.7; 0.18), LILRB2 (104; 4.6; 0.27), CLIC3 (927; 4.6; 0.00), TRGC1 (5444; 4.6; 0.01), EPDR1 (75; 4.6; 0.04), PLEK (11625; 4.6; 0.00), ADRB2 (1354; 4.6; 0.00), OSBPL5 (7558; 4.6; 0.01), CXCR2 (460; 4.6; 0.01), MMP23B (674; 4.5; 0.01), DAB2 (236; 4.5; 0.02), UBXN10 (187; 4.5; 0.01), GOLIM4 (117; 4.5; 0.02), GLB1L2 (1454; 4.5; 0.02), SLAMF7 (6689; 4.4; 0.01), SLAMF8 (265; 4.4; 0.01), FRMPD3 (1088; 4.4; 0.01), B3GNT7 (298; 4.4; 0.01), FCGR2B (126; 4.3; 0.04), ATP9A (398; 4.3; 0.01), GOLM1 (418; 4.3; 0.02), CCL5 (59948; 4.3; 0.01), FASLG (479; 4.3; 0.01), TP53I11 (1901; 4.3; 0.00), DOCK5 (673; 4.3; 0.13), SPHK1 (79; 4.3; 0.03), CACNA2D2 (3132; 4.2; 0.01), PTMS (1930; 4.2; 0.01), PHOSPHO1 (19; 4.2; 0.12), HOPX (2459; 4.2; 0.01), CD300A (9991; 4.2; 0.01), KIF19 (997; 4.2; 0.03), LCNL1 (257; 4.2; 0.01), TM4SF19 (141; 4.1; 0.05), EFHD2 (29405; 4.1; 0.01), TRPC3 (52; 4.1; 0.06), METRNL (1518; 4.1; 0.01), TRBV5-4 (2094; 4.1; 0.07), ACTN3 (68; 4.0; 0.05), PLCG2 (376; 4.0; 0.03), PTGS1 (34; 4.0; 0.31), GPR27 (119; 4.0; 0.02), MATK (9988; 4.0; 0.01), TRAV21 (1543; 4.0; 0.04), DRAXIN (1235; 4.0; 0.02), TSHZ3 (216; 4.0; 0.01), CXXC4 (33; 4.0; 0.06), AOAH (2730; 4.0; 0.01), IER5L (1169; 4.0; 0.01), KLRG1 (2240; 4.0; 0.01), SYNGR1 (1062; 3.9; 0.01), OASL (1158; 3.9; 0.01), C8G (172; 3.9; 0.03), BNC2 (109; 3.9; 0.04), F2R (1473; 3.9; 0.01), CERCAM (288; 3.9; 0.03), BFSP1 (438; 3.9; 0.03), PLOD1 (1296; 3.9; 0.01), FAM131B (210; 3.9; 0.02), TST (30; 3.9; 0.12), AGAP1 (1455; 3.9; 0.01), PTGDS (2384; 3.9; 0.01), GZMA (8115; 3.8; 0.01), EPB41L4A (250; 3.8; 0.01), STYK1 (337; 3.8; 0.02), ITGAD (58; 3.8; 0.03), DLG5 (524; 3.8; 0.01), CEBPA (28; 3.8; 0.12), PDLIM1 (489; 3.8; 0.01), C17orf66 (694; 3.7; 0.02), FHAD1 (214; 3.7; 0.03), CD300C (53; 3.7; 0.16), NPTX1 (170; 3.7; 0.06), STEAP3 (26; 3.6; 0.23), SOX13 (2601; 3.6; 0.02), DAPK2 (373; 3.6; 0.01), TRBV5-3 (114; 3.6; 0.14), FCRLB (139; 3.6; 0.02), TGFBR3L (76; 3.6; 0.07), PALLD (377; 3.6; 0.03), ERBB2 (2001; 3.6; 0.02), PNMT (87; 3.6; 0.06), LRRC43 (50; 3.6; 0.04), CD160 (297; 3.6; 0.06), XPNPEP2 (283; 3.6; 0.03), IL5RA (86; 3.6; 0.04), C3AR1 (208; 3.6; 0.02), PPP2R2B (693; 3.6; 0.01), HDGFRP3 (121; 3.6; 0.02), CHRNE (723; 3.5; 0.03), TBKBP1 (4679; 3.5; 0.02), MYO6 (867; 3.5; 0.01), CDHR1 (419; 3.5; 0.01), CXXC11 (469; 3.5; 0.06), SESN2 (1656; 3.5; 0.01), PTGDR (1341; 3.5; 0.01), IQSEC2 (259; 3.4; 0.03), TRGC2 (2817; 3.4; 0.03), GNGT2 (310; 3.4; 0.01), SLC4A4 (133; 3.4; 0.03), RHOC (1727; 3.4; 0.01), LGALS9C (43; 3.4; 0.06), CCR1 (43; 3.4; 0.22), ABI3 (2491; 3.4; 0.01), ENC1 (534; 3.4; 0.04), PROCR (155; 3.3; 0.03), C9orf172 (1699; 3.3; 0.02), GFPT2 (92; 3.3; 0.06), ENPP5 (204; 3.3; 0.02), PPM1L (437; 3.3; 0.02), CXXC5 (761; 3.3; 0.01), DNAH10 (51; 3.3; 0.08), PAK6 (91; 3.3; 0.05), HOXA1 (40; 3.3; 0.04), PRR5L (3432; 3.3; 0.01), MAP3K8 (979; 3.3; 0.01), FGFR2 (228; 3.3; 0.03), USP28 (3117; 3.2; 0.01), COPZ2 (107; 3.2; 0.04), TRPM2 (441; 3.2; 0.03), LATS2 (276; 3.2; 0.03), SERTAD3 (1183; 3.2; 0.02), TGFBR3 (3794; 3.2; 0.02), APOBEC3G (7616; 3.2; 0.01), APOBEC3H (502; 3.2; 0.03), MXRA7 (2042; 3.2; 0.02), VAV3 (854; 3.2; 0.01), EPHX4 (36; 3.1; 0.12), IFNG (297; 3.1; 0.10), PLA2G16 (675; 3.1; 0.02), CTSW (22553; 3.1; 0.02), TRGV8 (89; 3.1; 0.07), LAG3 (2228; 3.1; 0.04), FES (18; 3.1; 0.52), KIAA1671 (1733; 3.1; 0.02), XCL2 (79; 3.1; 0.07), B4GALT6 (43; 3.1; 0.05), GAB3 (4725; 3.1; 0.02), TTC16 (6334; 3.0; 0.03), CEP78 (5909; 3.0; 0.02), ADAP1 (1212; 3.0; 0.01), C12orf75 (1449; 3.0; 0.02), FEZ1 (245; 3.0; 0.03), PIF1 (355; 3.0; 0.04), SIGLEC9 (370; 3.0; 0.07), ARSD (640; 3.0; 0.01), FZD2 (17; 3.0; 0.27), NFIL3 (372; 3.0; 0.02), B4GALNT4 (1030; 3.0; 0.05), SUSD1 (957; 3.0; 0.02), PDE4A (1801; 3.0; 0.01), ADAMTS1 (114; 3.0; 0.04), SYTL2 (3154; 2.9; 0.02), FOSL2 (3988; 2.9; 0.01), VANGL1 (326; 2.9; 0.02), NTNG2 (1162; 2.9; 0.02), ST3GAL4 (400; 2.9; 0.02), VSIG10L (45; 2.8; 0.05), NCALD (1771; 2.8; 0.02), YPEL1 (3009; 2.8; 0.02), TRDC (727; 2.8; 0.02), MANEAL (191; 2.8; 0.05), SMAD7 (1756; 2.8; 0.02), GPRIN1 (87; 2.8; 0.05), FOXD2 (72; 2.8; 0.06), C17orf58 (65; 2.8; 0.07), TNNI2 (14; 2.8; 0.33), LPCAT1 (10152; 2.8; 0.02), GPR68 (1527; 2.8; 0.02), CCL3L3 (71; 2.8; 0.05), KLRC4-KLRK1 (263; 2.8; 0.03), CRIM1 (183; 2.8; 0.03), CYP4F22 (182; 2.8; 0.02), MYBL2 (28; 2.8; 0.15), CHN2 (293; 2.8; 0.02), RASSF1 (15114; 2.8; 0.02), PHPT1 (2425; 2.7; 0.03), CDK2AP1 (111; 2.7; 0.05), RAB27B (173; 2.7; 0.04), C9orf139 (373; 2.7; 0.08), SGCE (41; 2.7; 0.09), PODXL (110; 2.7; 0.03), PSD2 (34; 2.7; 0.10), MCTP2 (573; 2.7; 0.02), CADM1 (163; 2.7; 0.04), L3MBTL4 (176; 2.7; 0.02), TPST2 (4108; 2.7; 0.02), FGD2 (351; 2.7; 0.42), SLC2A8 (317; 2.7; 0.02), CLCF1 (1002; 2.7; 0.03), CLIC4 (20; 2.7; 0.34), CHST12 (3156; 2.7; 0.03), FUT11 (2482; 2.7; 0.02), RGS3 (3002; 2.7; 0.02), B4GALT2 (200; 2.6; 0.04), ZSCAN9 (288; 2.6; 0.02), TK1 (45; 2.6; 0.07), ST6GALNAC2 (226; 2.6; 0.03), HLA-DQA1 (119; 2.6; 0.18), SYNGR3 (163; 2.6; 0.07), LGALS1 (4060; 2.6; 0.03), ARVCF (534; 2.6; 0.07), RTKN (68; 2.6; 0.06), BSPRY (37; 2.6; 0.09), PDZD4 (5403; 2.6; 0.05), TFEB (1516; 2.6; 0.02), C10orf128 (1260; 2.6; 0.04), ARHGEF25 (121; 2.6; 0.08), MYO1F (37304; 2.5; 0.02), HES6 (192; 2.5; 0.05), SLC15A4 (1502; 2.5; 0.02), ITPRIPL2 (287; 2.5; 0.05), DPF3 (125; 2.5; 0.11), RBFOX3 (167; 2.5; 0.10), APOBEC3C (8514; 2.5; 0.02), SAMD3 (4283; 2.5; 0.04), TESC (302; 2.5; 0.03), RUNX3 (36199; 2.5; 0.04), SLC27A3 (3184; 2.5; 0.02), COL6A2 (16120; 2.5; 0.04), WIPI1 (516; 2.5; 0.03), MZB1 (69; 2.5; 0.16), HS6ST1 (1317; 2.5; 0.02), CD63 (3092; 2.5; 0.02), DUSP8 (1967; 2.4; 0.07), AMOT (207; 2.4; 0.04), IKZF2 (1408; 2.4; 0.07), F8 (134; 2.4; 0.04), CCDC50 (593; 2.4; 0.08), EOMES (1467; 2.4; 0.07), FAM179A (1168; 2.4; 0.04), TMC4 (358; 2.4; 0.06), GOLGA8I (698; 2.4; 0.03), RAP2A (1147; 2.4; 0.05), IL18RAP (1388; 2.4; 0.03), RAB11FIP5 (1559; 2.4; 0.07), FCHO2 (104; 2.4; 0.06), ITPRIPL1 (604; 2.4; 0.04), TRAV24 (87; 2.4; 0.11), RHBDF2 (6111; 2.4; 0.02), LAIR2 (178; 2.4; 0.11), GFI1 (1806; 2.4; 0.06), SMKR1 (108; 2.4; 0.06), RRAS2 (517; 2.4; 0.02), PLEKHF1 (1844; 2.4; 0.04), SPRED2 (64; 2.4; 0.05), NDST1 (32; 2.4; 0.35), CORO1C (379; 2.4; 0.17), MSC (298; 2.4; 0.10), CASKIN2 (80; 2.4; 0.08), JAKMIP2 (574; 2.4; 0.03), ELOVL6 (796; 2.4; 0.04), GATA6 (42; 2.4; 0.13), PCDHGB6 (53; 2.4; 0.11), CD8A (13345; 2.4; 0.06), SDSL (63; 2.3; 0.05), ZDHHC14 (358; 2.3; 0.03), TRPV3 (176; 2.3; 0.08), ST8SIA6 (72; 2.3; 0.10), IGFBP7 (10; 2.3; 0.44), RAB31 (5; 2.3; 0.64), CLEC12A (5; 2.3; 0.67), BHLHE40 (6228; 2.3; 0.03), JAZF1 (707; 2.3; 0.05), ZNF365 (310; 2.3; 0.05), SKAP2 (443; 2.3; 0.09), TRBV6-6 (381; 2.3; 0.15), MYBL1 (2672; 2.3; 0.04), HLA-DRB5 (413; 2.3; 0.19), ANXA4 (755; 2.3; 0.03), TPRG1 (290; 2.3; 0.07), AKR1C3 (163; 2.3; 0.06), LLGL2 (8814; 2.3; 0.06), PLEKHG3 (6221; 2.3; 0.03), RASGEF1A (630; 2.3; 0.06), NUGGC (831; 2.3; 0.05), BMF (577; 2.3; 0.09), HLA-DRB1 (865; 2.3; 0.14), BAI2 (376; 2.3; 0.06), PAQR4 (267; 2.3; 0.03), LAT2 (618; 2.3; 0.21), SLC1A4 (425; 2.3; 0.03), CAMK2N1 (404; 2.3; 0.07), PTPN12 (2106; 2.2; 0.03), RAP1GAP2 (9875; 2.2; 0.03), GAS1 (49; 2.2; 0.19), CDKN2A (150; 2.2; 0.07), UCK2 (344; 2.2; 0.03), PATL2 (3609; 2.2; 0.06), SEPT4 (106; 2.2; 0.09), HLA-DPA1 (2870; 2.2; 0.13), ATP10D (134; 2.2; 0.15), LYAR (2540; 2.2; 0.04), MT1E (90; 2.2; 0.17), PDXP (52; 2.2; 0.09), GNAZ (70; 2.2; 0.08), IL2RB (12650; 2.2; 0.02), METTL7A (610; 2.2; 0.16), APOBR (8002; 2.2; 0.02), SYT11 (1724; 2.2; 0.03), GTSE1 (56; 2.2; 0.12), IRF6 (37; 2.2; 0.13), ICAM5 (9; 2.2; 0.34), TRAV38-1 (125; 2.2; 0.16), PRICKLE4 (120; 2.2; 0.07), TRGV10 (303; 2.2; 0.08), PIGZ (96; 2.2; 0.06), SSBP3 (7662; 2.1; 0.06), FAM46A (626; 2.1; 0.04), DMKN (132; 2.1; 0.06), TNS4 (36; 2.1; 0.15), PEG10 (36; 2.1; 0.19), ATP1A3 (1004; 2.1; 0.05), RRM2 (104; 2.1; 0.05), NCR3 (842; 2.1; 0.03), BMP1 (486; 2.1; 0.03), ZNF296 (206; 2.1; 0.04), APMAP (4505; 2.1; 0.04), B4GALT5 (1629; 2.1; 0.03), ST7 (237; 2.1; 0.05), MAN1A1 (433; 2.1; 0.07), ETFB (2180; 2.1; 0.06), GFOD1 (387; 2.1; 0.10), OSCAR (62; 2.1; 0.53), AGPAT4 (1920; 2.1; 0.03), C4orf50 (66; 2.1; 0.10), SPIRE1 (106; 2.1; 0.07), HLA-DQA2 (132; 2.1; 0.25), VCL (3667; 2.1; 0.04), JAKMIP1 (1443; 2.1; 0.08), ZNF35 (39; 2.1; 0.11), GSTA4 (61; 2.1; 0.07), TRIM17 (130; 2.1; 0.08), MIDN (6411; 2.1; 0.02), VIPR2 (91; 2.1; 0.14), PTRH1 (523; 2.1; 0.06), ARL4D (78; 2.1; 0.13), ABHD17C (150; 2.1; 0.08), SATB2 (30; 2.1; 0.17), FBXO6 (585; 2.0; 0.03), STX11 (294; 2.0; 0.16), PYHIN1 (2820; 2.0; 0.07), HES7 (47; 2.0; 0.19), TSPAN2 (424; 2.0; 0.08), KIF21A (1236; 2.0; 0.07), PSEN2 (185; 2.0; 0.04), FCRL3 (2868; 2.0; 0.08), ACTN4 (12543; 2.0; 0.03), SH2D2A (3553; 2.0; 0.05), EPS8L1 (153; 2.0; 0.09), and ID2 (4674; 2.0; 0.05). The foregoing genes may be used, for example, to identify, sort, select, kill, or otherwise target a polycytotoxic T cell. For example, an antibody that specifically binds the protein product of any one of the foregoing genes may be used to distinguish a polycytotoxic T cell from other CD3$^+$ T cells, e.g., by fluorescence-activated cell sorting or immunohistochemistry. Similarly, an antibody that specifically binds the extracellular portion of a membrane protein encoded by any one of the foregoing genes may be administered to a subject to kill polycytotoxic T cells in the subject.

The gene expression profiles for polycytotoxic T cells were compared to the gene expression profiles for non-cytotoxic CD3$^+$ T cells. The following genes were upregulated in polycytotoxic T cells relative to non-cytotoxic CD3$^+$ T cells, wherein the first number in parentheses corresponds to the expression level, the second number corresponds to the fold-change for polycytotoxic T cells relative to non-cytotoxic CD3$^+$ T cells, and the third number corresponds to the p-value: SLC1A7 (1595; 15.6; 0.05), NME8 (1197; 15.2; 0.05), PCDH1 (419; 13.7; 0.08), COL13A1 (218; 12.7; 0.02), ADAMTS14 (94; 11.5; 0.04), PPP1R14C (75; 11.2; 0.05), SORCS2 (73; 11.2; 0.05), FZD2 (72; 11.2; 0.05), SH2D1B (71; 11.1; 0.05), CCL4L2 (69; 11.1; 0.05), STXBP6 (52; 10.7; 0.07), RCVRN (43; 10.4; 0.08), GZMB (22892; 10.4; 0.03), LIM2 (33; 10.0; 0.10), IGFBP7 (30; 9.9; 0.10), NUAK1 (772; 9.8; 0.00), GZMH (40024; 9.7; 0.04), SPRY2 (24; 9.6; 0.13), FCGR3A (6549; 9.4; 0.04), CMKLR1 (3903; 9.3; 0.05), GNLY (244692; 9.3; 0.05), FAM20C (19; 9.2; 0.15), FCGR3B (17; 9.1; 0.17), HBA2 (17; 9.1; 0.17), KIR2DS4 (1277; 8.9; 0.00), GPR56 (29058; 8.8; 0.05), FGFBP2 (14484; 8.8; 0.05), LILRA2 (13; 8.7; 0.20), LOXL3 (12; 8.6; 0.21), CD86 (11; 8.4; 0.23), TM6SF1 (11; 8.4; 0.23), CATSPER1 (10; 8.2; 0.25), IGLV3-10 (10; 8.2; 0.25), TYROBP (3609; 8.2; 0.06), PDGFRB (1271; 8.2; 0.00), CX3CR1 (9394; 8.2; 0.06), CCL3 (987; 8.2; 0.00), NCAM1 (730; 8.1; 0.00), LILRB2 (460; 8.1; 0.00), LILRA1 (8; 8.1; 0.28), TNNI2 (8; 8.1; 0.28), IGLV2-11 (8; 8.1; 0.28), EFNA5 (457; 8.1; 0.00), GPR97 (219; 8.0; 0.01), ASCL2 (3163; 7.9; 0.06), KIR2DL3 (594; 7.8; 0.00), CXCR1 (341; 7.6; 0.00), FGR (20278; 7.6; 0.07), C1orf21 (3431; 7.6; 0.00), S1PR5 (7951; 7.4; 0.07), GPR141 (272; 7.3; 0.01), STEAP3 (5; 7.2; 0.36), MLC1 (1681; 7.2; 0.00), LILRB2 (129; 7.2; 0.02), LILRB1 (7917; 7.2; 0.00), NKG7 (61760; 7.0; 0.08), LYN (737; 6.9; 0.00), FCRL6 (11800; 6.9; 0.00), CCL4 (6287; 6.9; 0.00), KIR3DL1 (593; 6.8; 0.00), TNS1 (4; 6.8; 0.39), TCL1A (4; 6.8; 0.39), IL1RN (4; 6.8; 0.39), FBN2 (4; 6.8; 0.39), CD300LB (4; 6.8; 0.39), KLRF1 (2377; 6.8; 0.00), HSPA6 (182; 6.7; 0.01), ZEB2 (5626; 6.7; 0.00), CXXC4 (87; 6.7; 0.03), NCR1 (1362; 6.6; 0.00), HHEX (164; 6.6; 0.01), ZNF683 (12174; 6.5; 0.00), F7 (80; 6.5; 0.04), SIGLEC7 (80; 6.5; 0.04), TRDV2 (884; 6.4; 0.00), BFSP1 (441; 6.4; 0.01), CTBP2 (1784; 6.3; 0.00), LRP3 (2; 6.2; 0.43), SERPING1 (2; 6.2; 0.43), SETBP1 (977; 6.2; 0.00), TMCC3 (572; 6.2; 0.00), SLCO4C1 (885; 6.1; 0.00), TM4SF19 (177; 6.1; 0.02), KLRD1 (10036; 6.1; 0.00), FCGR2C (230; 6.1; 0.01), LGR6 (3250; 6.0; 0.00), FCGR2A (282; 6.0; 0.01), ITGAM (20064; 6.0; 0.00), TRGV8 (437; 6.0; 0.01), SGCE (53; 5.9; 0.07), CLDND2 (3834; 5.9; 0.00), TRGV9 (623; 5.9; 0.01), BOK (51; 5.9; 0.07), NCS1 (100; 5.9; 0.03), DAB2 (298; 5.8; 0.01), PLEK (14777; 5.8; 0.00), PODN (378; 5.8; 0.01), NMUR1 (2294; 5.8; 0.00), TBX21 (18220; 5.8; 0.00), RASSF4 (2508; 5.8; 0.00), GLT1D1 (89; 5.7; 0.04), FAM49A (800; 5.7; 0.01), BTBD17 (87; 5.7; 0.04), FASLG (688; 5.6; 0.01), TFCP2L1 (471; 5.6; 0.01), GSC (84; 5.6; 0.04), PDGFD (372; 5.6; 0.01), RGS9 (2083; 5.6; 0.00), LRRC16B (831; 5.5; 0.01), CD160 (1340; 5.5; 0.00), RAB38 (77; 5.5; 0.05), SLAMF7 (9801; 5.5; 0.00), CST7 (20761; 5.4; 0.00), PRSS23 (2082; 5.4; 0.00), ADRB2

(2193; 5.4; 0.00), CD244 (3569; 5.4; 0.00), PRF1 (54506; 5.3; 0.00), KLRC2 (707; 5.3; 0.01), FAM131B (370; 5.3; 0.01), TRDC (7447; 5.3; 0.00), ARHGEF10L (1; 5.2; 0.51), LGALS2 (1; 5.2; 0.51), VNN1 (1; 5.2; 0.51), CSTA (1; 5.2; 0.51), CDC42EP1 (1; 5.2; 0.51), TLR4 (1; 5.2; 0.51), STON2 (1; 5.2; 0.51), CD1D (1; 5.2; 0.51), ASGR2 (1; 5.2; 0.51), SDPR (1; 5.2; 0.51), OLIG1 (1; 5.2; 0.51), CLEC17A (1; 5.2; 0.51), IGHV1-69 (1; 5.2; 0.51), HBA1 (64; 5.2; 0.07), CEBPA (31; 5.2; 0.14), C1orf177 (273; 5.1; 0.02), KYNU (30; 5.1; 0.14), PLOD1 (3878; 5.1; 0.00), FCGR2B (202; 5.1; 0.02), KIF19 (2503; 5.0; 0.01), GPR114 (8870; 5.0; 0.00), FRMPD3 (1325; 5.0; 0.01), PIK3AP1 (1271; 5.0; 0.01), C19orf35 (54; 5.0; 0.09), KIR2DL1 (53; 4.9; 0.09), KLRC1 (1191; 4.9; 0.01), CXXC11 (1985; 4.9; 0.01), SGCD (131; 4.9; 0.04), B3GAT1 (2843; 4.9; 0.01), CCL5 (123486; 4.9; 0.00), MEIS1 (25; 4.9; 0.17), C17orf66 (1284; 4.8; 0.01), B3GNT7 (637; 4.8; 0.01), TTC38 (7377; 4.8; 0.01), ISL2 (48; 4.8; 0.10), APOBEC3B (48; 4.8; 0.10), SPON2 (14636; 4.8; 0.01), MMP23B (1114; 4.8; 0.01), TRGJP2 (47; 4.8; 0.11), ARHGEF28 (396; 4.8; 0.02), GAS7 (1579; 4.8; 0.01), CD300C (161; 4.7; 0.03), KIF13A (159; 4.7; 0.04), SLAMF8 (294; 4.7; 0.02), CACNA2D2 (5421; 4.7; 0.01), PTMS (2225; 4.7; 0.01), GPR153 (684; 4.7; 0.01), TRGC1 (5564; 4.7; 0.01), CCL4L1 (22; 4.7; 0.21), MGAM (22; 4.7; 0.21), STYK1 (429; 4.6; 0.02), TMEM255A (252; 4.6; 0.03), CXCR2 (965; 4.6; 0.01), DLG5 (2615; 4.6; 0.01), TRGC2 (7180; 4.6; 0.01), CLEC12A (20; 4.6; 0.22), GZMA (17114; 4.5; 0.01), CST3 (396; 4.5; 0.02), KIFC3 (601; 4.5; 0.01), IFNG (659; 4.5; 0.01), AGAP1 (1908; 4.5; 0.01), MYL9 (39; 4.5; 0.14), PTGDR (1784; 4.5; 0.01), FKBP10 (113; 4.5; 0.06), CLIC3 (1607; 4.4; 0.01), BNC2 (37; 4.4; 0.14), SOX13 (3519; 4.4; 0.01), F2R (2330; 4.4; 0.01), TRGV2 (352; 4.4; 0.02), ADRB1 (175; 4.3; 0.04), TSHZ3 (243; 4.3; 0.03), ITGAX (1671; 4.3; 0.01), FKBP1B (101; 4.3; 0.07), MAFB (17; 4.3; 0.27), CD300A (10364; 4.3; 0.01), PRR5L (5063; 4.3; 0.01), SERTAD3 (4226; 4.3; 0.01), FADS2 (466; 4.2; 0.02), METRNL (1674; 4.2; 0.01), EFHD2 (40985; 4.1; 0.01), TRBV7-1 (133; 4.1; 0.06), ABCB4 (14; 4.1; 0.31), MATK (12559; 4.1; 0.01), B4GALT6 (86; 4.0; 0.09), SPHK1 (199; 4.0; 0.04), EPB41L4A (619; 4.0; 0.02), PDLIM1 (322; 4.0; 0.03), C9orf172 (1511; 4.0; 0.01), TBKBP1 (6915; 3.9; 0.01), LAG3 (3581; 3.9; 0.01), IER5L (1767; 3.9; 0.01), FHAD1 (130; 3.9; 0.07), CERCAM (583; 3.9; 0.02), OSBPL5 (12674; 3.9; 0.01), ATP8B4 (64; 3.9; 0.12), XPN-PEP2 (445; 3.9; 0.03), NGFR (88; 3.9; 0.09), MANEAL (249; 3.9; 0.04), ENC1 (3261; 3.8; 0.01), KIR3DL2 (1475; 3.8; 0.02), SLC4A4 (205; 3.8; 0.05), CDC20 (72; 3.8; 0.11), TP53I11 (1809; 3.8; 0.02), KIR3DX1 (869; 3.8; 0.02), OASL (1246; 3.8; 0.02), TGFBR3 (7270; 3.8; 0.01), PLA2G16 (946; 3.8; 0.02), PTGDS (6352; 3.8; 0.01), PAK6 (223; 3.8; 0.05), CASKIN2 (70; 3.8; 0.12), GFOD1 (1599; 3.8; 0.02), PROK2 (104; 3.7; 0.09), LAIR2 (511; 3.7; 0.03), RAPGEF3 (57; 3.7; 0.14), ABI3 (4502; 3.7; 0.01), APOBEC3H (1370; 3.7; 0.02), PPP2R2B (1079; 3.7; 0.02), DTL (100; 3.7; 0.09), VIPR2 (199; 3.7; 0.05), EFCAB4A (208; 3.7; 0.05), GOLIM4 (120; 3.7; 0.08), CPVL (11; 3.7; 0.39), CTSW (24163; 3.7; 0.01), RHOC (1866; 3.6; 0.02), CHRNE (700; 3.6; 0.03), ACTN3 (73; 3.6; 0.12), CTIF (534; 3.6; 0.03), TRPC3 (82; 3.6; 0.11), MAP3K8 (2367; 3.6; 0.02), EPHX4 (112; 3.6; 0.09), TK1 (241; 3.5; 0.05), PLCG2 (399; 3.5; 0.04), LCNL1 (664; 3.5; 0.03), APOBEC3G (12300; 3.5; 0.02), SATB2 (116; 3.5; 0.09), TNFSF9 (276; 3.5; 0.05), PKMYT1 (161; 3.5; 0.07), FEZ1 (673; 3.5; 0.03), C9orf139 (549; 3.5; 0.03), ADAMTS1 (375; 3.4; 0.04), SIGLEC9 (642; 3.4; 0.03), GNGT2 (377; 3.4; 0.04), GOLM1 (284; 3.4; 0.05), SEPT4 (190; 3.4; 0.07), PALLD (499; 3.4; 0.04), SYNGR1 (1477; 3.4; 0.02), CLCF1 (1714; 3.4; 0.02), EOMES (3162; 3.4; 0.02), COL-GALT2 (308; 3.4; 0.05), MXRA7 (2144; 3.3; 0.02), CXXC5 (894; 3.3; 0.03), LATS2 (364; 3.3; 0.05), SYNGR3 (251; 3.3; 0.06), HLA-DQA2 (129; 3.3; 0.09), XCL2 (170; 3.3; 0.08), TYMS (278; 3.3; 0.05), CCDC170 (17; 3.3; 0.34), SLC2A8 (554; 3.3; 0.04), UBXN10 (158; 3.3; 0.08), C2orf48 (58; 3.3; 0.17), TNFRSF12A (41; 3.3; 0.21), IGLV3-12 (245; 3.2; 0.06), MSC (513; 3.2; 0.04), ANKRD35 (33; 3.2; 0.24), GLB1L2 (528; 3.2; 0.04), NFIL3 (1397; 3.2; 0.03), KLRG1 (2508; 3.2; 0.02), JAKMIP2 (743; 3.2; 0.03), TDRD9 (214; 3.2; 0.07), ERBB2 (2976; 3.2; 0.02), PPM1L (841; 3.2; 0.03), SMKR1 (202; 3.2; 0.07), MYO6 (2005; 3.2; 0.03), FCRL3 (4313; 3.2; 0.02), ATP9A (131; 3.2; 0.10), ZSCAN9 (347; 3.2; 0.05), PLXDC2 (39; 3.2; 0.23), HLA-DRB1 (4587; 3.2; 0.02), IL18RAP (5039; 3.1; 0.02), CDHR1 (565; 3.1; 0.04), GAB3 (8092; 3.1; 0.02), USP28 (4869; 3.1; 0.02), HOPX (2986; 3.1; 0.03), HLA-DRB5 (2427; 3.1; 0.03), MYO1F (74275; 3.1; 0.02), FAM179A (2301; 3.1; 0.03), DMKN (166; 3.1; 0.09), ACPP (14; 3.1; 0.39), VAV3 (1619; 3.0; 0.03), PHPT1 (3501; 3.0; 0.03), FGL2 (361; 3.0; 0.06), NTNG2 (2017; 3.0; 0.03), TNFRSF9 (99; 3.0; 0.13), NRXN2 (42; 3.0; 0.23), PDZD4 (14920; 3.0; 0.02), JAZF1 (1260; 3.0; 0.03), BZRAP1 (13283; 3.0; 0.03), CCR1 (54; 3.0; 0.20), HLA-DPA1 (5315; 3.0; 0.03), ACHE (81; 3.0; 0.15), TGFBR3L (81; 3.0; 0.15), FOXD2 (134; 3.0; 0.11), PROCR (200; 3.0; 0.08), DOCK5 (412; 2.9; 0.06), CORO1C (811; 2.9; 0.04), C12orf75 (2598; 2.9; 0.03), IL17C (110; 2.9; 0.13), ADAP1 (1814; 2.9; 0.03), ERRFI1 (251; 2.9; 0.08), YPEL1 (4624; 2.9; 0.03), CHST12 (4568; 2.9; 0.03), RGS3 (4711; 2.9; 0.03), FCRLB (76; 2.9; 0.17), UBE2C (25; 2.9; 0.32), GNAO1 (1232; 2.9; 0.04), ITPRIPL1 (982; 2.9; 0.04), HLA-DPB1 (8919; 2.9; 0.03), PLEKHG3 (9206; 2.9; 0.03), PLXND1 (4259; 2.9; 0.03), OSCAR (43; 2.8; 0.24), AKR1C3 (718; 2.8; 0.05), TTC16 (12792; 2.8; 0.03), LGALS1 (5685; 2.8; 0.03), KCNT1 (154; 2.8; 0.11), IQSEC2 (320; 2.8; 0.07), PAQR4 (455; 2.8; 0.06), WIPI1 (866; 2.8; 0.04), OTOF (442; 2.8; 0.06), RASSF1 (23039; 2.8; 0.03), BSPRY (98; 2.8; 0.15), TRPM2 (548; 2.8; 0.05), BMF (795; 2.8; 0.05), CAMK2N1 (960; 2.8; 0.04), MT1E (482; 2.8; 0.06), CSF1R (6; 2.8; 0.56), SLC8A1 (6; 2.8; 0.56), TFEB (2676; 2.8; 0.03), TESC (448; 2.8; 0.06), CPNE8 (65; 2.8; 0.19), TRAV12-2 (1070; 2.8; 0.04), RRM2 (388; 2.8; 0.07), KLRC3 (47; 2.8; 0.24), MCTP2 (861; 2.8; 0.05), SKAP2 (1047; 2.8; 0.04), TRAV38-2DV8 (152; 2.8; 0.11), RHBDF2 (11676; 2.8; 0.03), SLC27A3 (4840; 2.8; 0.03), ENPP5 (198; 2.8; 0.10), APOBEC3C (15980; 2.8; 0.03), HLA-DRA (2099; 2.7; 0.04), IL2RB (12401; 2.7; 0.03), JAKMIP1 (1682; 2.7; 0.04), ST3GAL4 (537; 2.7; 0.06), SESN2 (1623; 2.7; 0.04), ZNF365 (387; 2.7; 0.07), PLTP (34; 2.7; 0.29), LPCAT1 (16134; 2.7; 0.03), MYRF (319; 2.7; 0.08), KLRC4 (95; 2.7; 0.16), SERTAD1 (1759; 2.7; 0.04), BIRC7 (106; 2.7; 0.15), C8G (257; 2.7; 0.09), TRAV22 (284; 2.7; 0.08), ARAP3 (1025; 2.7; 0.05), CDC45 (126; 2.7; 0.14), HES6 (302; 2.7; 0.08), SMPD3 (835; 2.7; 0.05), CDCA5 (114; 2.7; 0.15), ABHD17C (223; 2.7; 0.10), TP73 (33; 2.7; 0.31), CYBB (11; 2.7; 0.49), SUSD1 (1250; 2.6; 0.05), CD8A (29394; 2.6; 0.03), GPR25 (466; 2.6; 0.07), PIF1 (672; 2.6; 0.06), KIF18B (37; 2.6; 0.29), LRRC4 (27; 2.6; 0.34), TPRG1 (417; 2.6; 0.07), EDARADD (316; 2.6; 0.08), PLEKHF1 (2692; 2.6; 0.04), FADS1 (446; 2.6; 0.07), FOSL2 (7309; 2.6; 0.04), PHLDB2 (590; 2.6; 0.06), GNAZ (99; 2.6; 0.17), CD63 (4580; 2.6; 0.04), TMC4 (1040; 2.6; 0.05), BHLHE40 (10045; 2.6; 0.04), RTKN (67; 2.6; 0.21), SMAD7 (1543; 2.6; 0.05), RTN4RL2 (36; 2.6; 0.30), KIAA1671 (1266; 2.6; 0.05), RGS17 (61; 2.6; 0.22), PRSS22 (137; 2.6; 0.14), FUT11 (4492; 2.6; 0.04), GFPT2 (166; 2.5; 0.12), COPZ2 (196; 2.5; 0.11), TPBGL (86; 2.5; 0.19), CHN2 (695; 2.5; 0.06), ZDHHC1 (35; 2.5; 0.31), RUNX3 (51471; 2.5; 0.04), CRIM1 (159; 2.5; 0.13), TNFSF14 (1111; 2.5; 0.05), PLD1 (142; 2.5; 0.14), TRPV3 (277; 2.5; 0.10), SLC15A4 (2324; 2.5; 0.05), LLGL2 (14761; 2.5; 0.04), MKI67 (913; 2.5; 0.06), CDC6 (92; 2.5; 0.18), PCDHGB6 (63; 2.5; 0.23), RCAN2 (10; 2.5; 0.53), SIRPA (10; 2.5; 0.53), P2RX1 (5; 2.5; 0.63), CALHM2 (2611; 2.5; 0.05), TPST2 (4852; 2.5; 0.04), UCK2 (560; 2.5; 0.07), RHOB (1631; 2.5; 0.05), CD70 (213; 2.5; 0.11), APMAP (8564; 2.5; 0.04), PYHIN1 (7736; 2.5; 0.04), RAB11FIP5 (1713; 2.4; 0.05), GTSE1 (122; 2.4; 0.16), ESPL1 (75; 2.4; 0.21), GSTA4 (125; 2.4; 0.16), ITPRIPL2 (431; 2.4; 0.08), CDKN2B (55; 2.4; 0.25), ACTN4 (16219; 2.4; 0.04), C17orf58 (73; 2.4; 0.22), SKA1 (92; 2.4; 0.19), RAD51AP1 (46; 2.4; 0.28), C10orf128 (3519; 2.4; 0.05), EPS8L1 (265; 2.4; 0.10), ST8SIA6 (151; 2.4; 0.14), BAI2 (593; 2.4; 0.07), LRRC43 (41; 2.4; 0.30), CHST10 (445; 2.4; 0.08), C4orf50 (54; 2.4; 0.26), NUGGC (726; 2.4; 0.07), DDN (49; 2.4; 0.28), C3AR1 (336; 2.4; 0.09), PDE4A (1705; 2.4; 0.05), PSD2 (45; 2.4; 0.29), PATE2 (45; 2.4; 0.29), SYCE1 (410; 2.4; 0.09), SLC27A2 (58; 2.4; 0.26), KLRC4-KLRK1 (151; 2.4; 0.15), ARSD (495; 2.4; 0.08), SLC22A1 (53; 2.4; 0.27), ZDHHC14 (467; 2.4; 0.08), CCR5 (1313; 2.4; 0.06), STOM (5127; 2.4; 0.05), TRGV10 (193; 2.3; 0.13), EPDR1 (92; 2.3; 0.20), DAPK2 (369; 2.3; 0.09), HOXA1 (43; 2.3; 0.30), CDC25A (43; 2.3; 0.30), TMEM171 (22; 2.3; 0.41), CCR3 (117; 2.3; 0.18), GNAL (229; 2.3; 0.12), CEBPD (513; 2.3; 0.08), GPR68 (1249; 2.3; 0.06), SAMD3 (7588; 2.3; 0.05), APOBR (12295; 2.3; 0.05), CLECL1 (120; 2.3; 0.17), RAP1GAP2 (15095; 2.3; 0.05), CLSPN (312; 2.3; 0.10), MYBL1 (5193; 2.3; 0.05), KLF10 (410; 2.3; 0.09), MYBL2 (102; 2.3; 0.19), RHEBL1 (371; 2.3; 0.10), MEX3D (225; 2.3; 0.12), SPIRE1 (143; 2.3; 0.16), RAB6B (126; 2.3; 0.17), HSPA2 (59; 2.3; 0.26), CHRNA7 (42; 2.3; 0.31), RBP7 (17; 2.3; 0.46), MYOF (8; 2.3; 0.57), NCALD (2690; 2.3; 0.05), C17orf96 (125; 2.3; 0.17), SYT11 (2297; 2.3; 0.06), CD72 (1114; 2.3; 0.07), NCR3 (963; 2.3; 0.07), B4GALNT4 (1173; 2.3; 0.06), HIVEP3 (1808; 2.3; 0.06), CYP4F22 (136; 2.3; 0.17), RASGEF1A (720; 2.3; 0.08), SCN4A (49; 2.3; 0.29), DNAH10 (82; 2.3; 0.23), AGPAT4 (3210; 2.2; 0.05), STX11 (217; 2.2; 0.13), LYNX1 (73; 2.2; 0.24), MIDN (9275; 2.2; 0.05), FBXO6 (947; 2.2; 0.07), KIF21A (2178; 2.2; 0.06), B4GALT5 (2733; 2.2; 0.06), SCDS (223; 2.2; 0.13), IDO2 (45; 2.2; 0.31), ZMYND10 (897; 2.2; 0.07), DTHD1 (105; 2.2; 0.20), CCNB3 (36; 2.2; 0.35), ADAM28 (12; 2.2; 0.53), TNF (638; 2.2; 0.08), MPST (1176; 2.2; 0.07), SEMA4A (366; 2.2; 0.10), PTPN12 (2688; 2.2; 0.06), ENPP4 (698; 2.2; 0.08), FCHO2 (151; 2.2; 0.16), RPL39L (139; 2.2; 0.17), NPTX1 (83; 2.2; 0.23), ELOVL6 (841; 2.2; 0.08), GNPTAB (6892; 2.2; 0.05), RNF165 (408; 2.2; 0.10), ACOT4 (245; 2.2; 0.13), SLC1A5 (1275; 2.2; 0.07), TST (54; 2.2; 0.29), GPRIN1 (93; 2.2; 0.22), TSPAN2 (420; 2.2; 0.10), HES7 (100; 2.2; 0.21), VCL (6497; 2.2; 0.06), SPRED2 (46; 2.1; 0.32), DRAXIN (557; 2.1; 0.09), DNAJC1 (2694; 2.1; 0.06), WNT1 (136; 2.1; 0.18), ZNF703 (136; 2.1; 0.18), PDE5A (34; 2.1; 0.37), CCNB2 (34; 2.1; 0.37), F8 (146; 2.1; 0.18), SLC35G2 (123; 2.1; 0.20), CDKN1C (255; 2.1; 0.13), SLC1A4 (428; 2.1; 0.11), GABARAPL1 (5043; 2.1; 0.06), FGFR2 (330; 2.1; 0.12), SAP30 (267; 2.1; 0.13), PIGZ (179; 2.1; 0.16), FAM214B (1706; 2.1; 0.07), CLIC1 (7718; 2.1; 0.06), ARHGEF12 (1428; 2.1; 0.07), C17orf72 (345; 2.1; 0.12), ZFPM1 (6573; 2.1; 0.06), ADCY9 (2068; 2.1; 0.07), PTTG1 (430; 2.1; 0.11), WDR63 (33; 2.1; 0.39), BANK1 (4; 2.1; 0.71), TPPP3 (4; 2.1; 0.71), LILRB4 (4; 2.1; 0.71), IGLV2-14 (4; 2.1; 0.71), PATL2 (5550; 2.1; 0.06), MTSS1 (3837; 2.1; 0.06), CDT1 (301; 2.1; 0.13), ARHGAP18 (287; 2.1; 0.13), ATP1A3 (1290; 2.1; 0.08), CTRC (286; 2.1; 0.13), CASZ1 (1394; 2.0; 0.08), LANCL3 (75; 2.0; 0.27), KIFC1 (67; 2.0; 0.28), NHSL2 (301; 2.0; 0.13), REEP2 (57; 2.0; 0.31), RRAS2 (608; 2.0; 0.10), ATF3 (53; 2.0; 0.32), IL12A (130; 2.0; 0.20), GTSF1 (345; 2.0; 0.12), CDKN3 (42; 2.0; 0.35), RAG1 (39; 2.0; 0.37), ATP10D (279; 2.0; 0.14), DNAJC28 (59; 2.0; 0.30), SAPCD2 (59; 2.0; 0.30), SYTL2 (4260; 2.0; 0.07), DUSP8 (3148; 2.0; 0.07), NPC1 (3810; 2.0; 0.07), KHDC1 (163; 2.0; 0.18), and SYNE1 (27629; 2.0; 0.06). The foregoing genes may be used, for example, to identify, sort, select, kill, or otherwise target a polycytotoxic T cell. For example, an antibody that specifically binds the protein product of any one of the foregoing genes may be used to distinguish a polycytotoxic T cell from non-cytotoxic T cells, e.g., by fluorescence-activated cell sorting or immunohistochemistry. Similarly, an antibody that specifically binds the extracellular portion of a membrane protein encoded by any one of the foregoing genes may be administered to a subject to kill polycytotoxic T cells in the subject.

REFERENCES

1. Bruns H, Meinken C, Schauenberg P, Harter G, Kern P, Modlin R L, Antoni C, Stenger S. Anti-TNF immunotherapy reduces CD8+ T cell-mediated antimicrobial activity against *Mycobacterium tuberculosis* in humans. J Clin Invest. 119:1167-1177, 2009. PubMed Central PMCID: PMCPMC2673881.
2. Walch M, Dotiwala F, Mulik S, Thiery J, Kirchhausen T, Clayberger C, Krensky A M, Martinvalet D, Lieberman J. Cytotoxic cells kill intracellular bacteria through granulysin-mediated delivery of granzymes. Cell. 157:1309-1323, 2014. PubMed Central PMCID: PMCPMC4090916.
3. Dotiwala F, Mulik S, Polidoro R B, Ansara J A, Burleigh B A, Walch M, Gazzinelli R T, Lieberman J. Killer lymphocytes use granulysin, perforin and granzymes to kill intracellular parasites. Nat Med. 2016.
4. Busch M, Herzmann C, Kallert S, Zimmermann A, Hofer C, Mayer D, Zenk S F, Muche R, Lange C, Bloom B R, Modlin R L, Stenger S, Network T B. Lipoarabinomannan-responsive Polycytotoxic T Cells are Associated With Protection in Human Tuberculosis. Am J Respir Crit Care Med. 2016.
5. Krensky A M, Clayberger C. Granulysin: a novel host defense molecule. Am J Transplant. 5:1789-1792, 2005.
6. Ridley D S, Jopling W H. Classification of leprosy according to immunity. A five-group system. Int J Lepr Other Mycobact Dis. 34:255-273, 1966.
7. Bloom B R. Learning from leprosy: a perspective on immunology and the Third World. J Immunol. 137:i-x, 1986.
8. Yamamura M, Uyemura K, Deans R J, Weinberg K, Rea T H, Bloom B R, Modlin R L. Defining protective responses to pathogens: cytokine profiles in leprosy lesions. Science. 254:277-279, 1991.
9. Montoya D, Cruz D, Teles R M, Lee D J, Ochoa M T, Krutzik S R, Chun R, Schenk M, Zhang X, Ferguson B G, Burdick A E, Sarno E N, Rea T H, Hewison M, Adams J S, Cheng G, Modlin R L. Divergence of macrophage phagocytic and antimicrobial programs in leprosy. Cell Host Microbe. 6:343-353, 2009. PubMed Central PMCID: PMCPMC2764558.

10. Cambier C J, Falkow S, Ramakrishnan L. Host evasion and exploitation schemes of *Mycobacterium tuberculosis*. Cell. 159:1497-1509, 2014.
11. Ochoa M T, Stenger S, Sieling P A, Thoma-Uszynski S, Sabet S, Cho S, Krensky A M, Rollinghoff M, Nunes Sarno E, Burdick A E, Rea T H, Modlin R L. T-cell release of granulysin contributes to host defense in leprosy. Nat Med. 7:174-179, 2001.
12. Stenger S, Hanson D A, Teitelbaum R, Dewan P, Niazi K R, Froelich C J, Ganz T, Thoma-Uszynski S, Melian A, Bogdan C, Porcelli S A, Bloom B R, Krensky A M, Modlin R L. An antimicrobial activity of cytolytic T cells mediated by granulysin. Science. 282:121-125, 1998.
13. Semple P L, Watkins M, Davids V, Krensky A M, Hanekom W A, Kaplan G, Ress S. Induction of granulysin and perforin cytolytic mediator expression in 10-week-old infants vaccinated with BCG at birth. Clin Dev Immunol. 2011:438463, 2011. PubMed Central PMCID: PMCPMC3018618.
14. Hrvatin S, Deng F, O'Donnell C W, Gifford D K, Melton D A. MARIS: method for analyzing RNA following intracellular sorting. PLoS One. 9:e89459, 2014. PubMed Central PMCID: PMCPMC3940959.
15. Fabri M, Stenger S, Shin D M, Yuk J M, Liu P T, Realegeno S, Lee H M, Krutzik S R, Schenk M, Sieling P A, Teles R, Montoya D, Iyer S S, Bruns H, Lewinsohn D M, Hollis B W, Hewison M, Adams J S, Steinmeyer A, Zugel U, Cheng G, Jo E K, Bloom B R, Modlin R L. Vitamin D is required for IFN-gamma-mediated antimicrobial activity of human macrophages. Sci Transl Med. 3:104ra102, 2011. PubMed Central PMCID: PMCPMC3269210.
16. Yuk J M, Shin D M, Lee H M, Yang C S, Jin H S, Kim K K, Lee Z W, Lee S H, Kim J M, Jo E K. Vitamin D3 induces autophagy in human monocytes/macrophages via cathelicidin. Cell Host Microbe. 6:231-243, 2009.
17. Yang C S, Shin D M, Kim K H, Lee Z W, Lee C H, Park S G, Bae Y S, Jo E K. NADPH oxidase 2 interaction with TLR2 is required for efficient innate immune responses to mycobacteria via cathelicidin expression. J Immunol. 182:3696-3705, 2009.
18. Arlettaz L, Villard J, de Rham C, Degermann S, Chapuis B, Huard B, Roosnek E. Activating C D94:NKG2C and inhibitory CD94:NKG2A receptors are expressed by distinct subsets of committed CD8+ TCR alphabeta lymphocytes. Eur J Immunol. 34:3456-3464, 2004.
19. Liu P T, Wheelwright M, Teles R, Komisopoulou E, Edfeldt K, Ferguson B, Mehta M D, Vazirnia A, Rea T H, Sarno E N, Graeber T G, Modlin R L. MicroRNA-21 targets the vitamin D-dependent antimicrobial pathway in leprosy. Nat Med. 18:267-273, 2012. PubMed Central PMCID: PMCPMC3274599.
20. Hogg A E, Bowick G C, Herzog N K, Cloyd M W, Endsley J J. Induction of granulysin in CD8+ T cells by IL-21 and IL-15 is suppressed by human immunodeficiency virus-1. J Leukoc Biol. 86:1191-1203, 2009.
21. White L, Krishnan S, Strbo N, Liu H, Kolber M A, Lichtenheld M G, Pahwa R N, Pahwa S. Differential effects of IL-21 and IL-15 on perforin expression, lysosomal degranulation, and proliferation in CD8 T cells of patients with human immunodeficiency virus-1 (HIV). Blood. 109:3873-3880, 2007. PubMed Central PMCID: PMCPMC1874576.
22. Liu K, Catalfamo M, Li Y, Henkart P A, Weng N P. IL-15 mimics T cell receptor crosslinking in the induction of cellular proliferation, gene expression, and cytotoxicity in CD8+ memory T cells. Proc Natl Acad Sci USA. 99:6192-6197, 2002. PubMed Central PMCID: PMCPMC122925.
23. Jullien D, Sieling P A, Uyemura K, Mar N D, Rea T H, Modlin R L. IL-15, an immunomodulator of T cell responses in intracellular infection. J Immunol. 158:800-806, 1997.
24. Schluns K S, Lefrancois L. Cytokine control of memory T-cell development and survival. Nat Rev Immunol. 3:269-279, 2003.
25. Busch M, Herzmann C, Kallert S, Zimmermann A, Hoefer C, Mayer D, Zenk S F, Muche R, Lange C, Bloom B R, Modlin R L, Stenger S. Lipoarabinomannan-responsive polycytotoxic T cells contribute to protection in human tuberculosis. American journal of Resipiratory And Critical Care Medicine Accepted for publication: 2016.
26. Paradisi A, Abeni D, Bergamo F, Ricci F, Didona D, Didona B. Etanercept therapy for toxic epidermal necrolysis. J Am Acad Dermatol. 71:278-283, 2014.
27. Chung W H, Hung S I, Yang J Y, Su S C, Huang S P, Wei C Y, Chin S W, Chiou C C, Chu S C, Ho H C, Yang C H, Lu C F, Wu J Y, Liao Y D, Chen Y T. Granulysin is a key mediator for disseminated keratinocyte death in Stevens-Johnson syndrome and toxic epidermal necrolysis. Nat Med. 14:1343-1350, 2008.
28. Le Cleach L, Delaire S, Boumsell L, Bagot M, Bourgault-Villada I, Bensussan A, Roujeau J C. Blister fluid T lymphocytes during toxic epidermal necrolysis are functional cytotoxic cells which express human natural killer (NK) inhibitory receptors. Clin Exp Immunol. 119:225-230, 2000. PubMed Central PMCID: PMCPMC1905549.
29. Jongstra J, Schall T J, Dyer B J, Clayberger C, Jorgensen J, Davis M M, Krensky A M. The isolation and sequence of a novel gene from a human functional T cell line. J Exp Med. 165:601-614, 1987. PubMed Central PMCID: PMCPMC2188281.
30. Angelini D F, Zambello R, Galandrini R, Diamantini A, Placido R, Micucci F, Poccia F, Semenzato G, Borsellino G, Santoni A, Battistini L. NKG2A inhibits NKG2C effector functions of gammadelta T cells: implications in health and disease. J Leukoc Biol. 89:75-84, 2011.
31. Guma M, Busch L K, Salazar-Fontana L I, Bellosillo B, Morte C, Garcia P, Lopez-Botet M. The CD94/NKG2C killer lectin-like receptor constitutes an alternative activation pathway for a subset of CD8+ T cells. Eur J Immunol. 35:2071-2080, 2005.
32. Braud V M, Aldemir H, Breart B, Ferlin W G. Expression of CD94-NKG2A inhibitory receptor is restricted to a subset of CD8+ T cells. Trends Immunol. 24:162-164, 2003.

INCORPORATION BY REFERENCE

All patents, published patent applications, and other publications mentioned in the description above are incorporated by reference herein in their entirety.

EQUIVALENTS

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

What is claimed is:

1. A method for monitoring an immune response in a subject, comprising determining the concentration of polycytotoxic T cells in the blood of the subject, wherein the polycytotoxic T cells express CD3, granzyme B, perforin, and granulysin.

2. The method of claim 1, wherein the polycytotoxic T cells further express one or more of CD45RA, IL-15α receptor, IL-15β receptor, NKG2a, NKG2c, KIR2DL1, KIR2DS4, KIR3DL1, KLRC4, KLRF1, KLRC3, COL13A1, CHRNA7, TRDV2, LGR4, LAT2, ADAM28, SCN4A, GPR25, GPR75, KCNA6, TYROBP, ITGAX, RAMP1, KCNT1, CCR3, SIGLEC7, OTOF, ABCB4, CD300A, CD300C, CD8, CD56, and CD94.

3. The method of claim 1, wherein the polycytotoxic T cells further express one or more of ASCL2, ATP8B4, B3GAT1, BTBD17, C19orf35, C1orf21, CCL3, CCL4, CCL4L1, CD300LB, CLDND2, CMKLR1, CTBP2, CX3CR1, CXCR1, CYP1B1, EMR3, FAM20C, FAM49A, FCGR2A, FCGR2C, FCGR3A, FCGR3B, FCRL6, FGFBP2, FGR, GAS7, GLT1D1, GNLY, GPR141, GPR153, GPR56, GPR97, GSC, GZMB, GZMH, HBA1, HHEX, ISL2, ITGAM, ITGAX, KIR2DL1, KIR2DL3, KIR2DS4, KIR3DL1, KIR3DL2, KLRC1, KLRC2, KLRC3, KLRC4, KLRD1, KLRF1, LGALS9B, LILRA1, LILRA3, LILRB1, LILRB5, LRFN2, LRRC16B, LYN, MAFB, MGAM, MLC1, MYO3B, MYOM2, NCAM1, NCR1, NCS1, NKG7, NME8, NMUR1, NUAK1, PCDH1, PDGFD, PDGFRB, PIK3AP1, PODN, PRF1, PROK2, PRSS23, QPCT, RAB38, RASSF4, RCAN2, S1PR5, SETBP1, SGCD, SH2D1B, SH3RF1, SIGLEC7, SLC1A7, SLCO4C1, SORCS2, SPON2, SPRY2, TBX21, TFCP2L1, TM6SF1, TMCC3, TMEM255A, TRDV2, TRGJP2, TRGV2, TRGV9, TYROBP, ZEB2, and ZNF683.

4. The method of claim 1, wherein the polycytotoxic T cells further express one or more of ADAMTS14, ADRB2, ARHGEF10L, ASCL2, ASGR2, BFSP1, BOK, BTBD17, C1orf177, C1orf21, CATSPER1, CCL3, CCL4, CCL4L2, CD160, CD1D, CD244, CD300LB, CD86, CDC42EP1, CEBPA, CLDND2, CLEC17A, CMKLR1, COL13A1, CST7, CSTA, CTBP2, CX3CR1, CXCR1, CXXC4, DAB2, EFNA5, F7, FAM131B, FAM20C, FAM49A, FASLG, FBN2, FCGR2A, FCGR2B, FCGR2C, FCGR3A, FCGR3B, FCRL6, FGFBP2, FGR, FRMPD3, FZD2, GLT1D1, GNLY, GPR114, GPR141, GPR56, GPR97, GSC, GZMB, GZMH, HBA1, HBA2, HHEX, HSPA6, IGFBP7, IGHV1-69, IGLV2-11, IGLV3-10, IL1RN, ITGAM, KIF19, KIR2DL3, KIR2DS4, KIR3DL1, KLRC2, KLRD1, KLRF1, KYNU, LGALS2, LGR6, LILRA1, LILRA2, LILRB1, LILRB2, LILRB5, LIM2, LOXL3, LRP3, LRRC16B, LYN, MLC1, NCAM1, NCR1, NCS1, NKG7, NME8, NMUR1, NUAK1, OLIG1, PCDH1, PDGFD, PDGFRB, PIK3AP1, PLEK, PLOD1, PODN, PPP1R14C, PRF1, PRSS23, RAB38, RASSF4, RCVRN, RGS9, S1PR5, SDPR, SERPING1, SETBP1, SGCE, SH2D1B, SIGLEC7, SLAMF7, SLC1A7, SLCO4C1, SORCS2, SPRY2, STEAP3, STON2, STXBP6, TBX21, TCL1A, TFCP2L1, TLR4, TM4SF19, TM6SF1, TMCC3, TNNI2, TNS1, TRDC, TRDV2, TRGV8, TRGV9, TYROBP, VNN1, ZEB2, and ZNF683.

5. The method of claim 1, wherein the subject received an immune-modulating therapy prior to determining the concentration of polycytotoxic T cells.

6. The method of claim 5, wherein the immune-modulating therapy is a vaccine, interleukin, cytokine, chemokine, adoptive cell therapy, or immunosuppressive therapy.

7. The method of claim 6, wherein the interleukin therapy is IL-2, IL-7, or IL-15 therapy.

8. The method of claim 6, wherein the cytokine therapy is interferon or G-CSF.

9. The method of claim 6, wherein the chemokine therapy is CCL3, CCL26, or CXCL7.

10. The method of claim 6, wherein the adoptive cell therapy is TIL or CAR-T therapy.

11. The method of claim 6, wherein the immunosuppressive therapy is corticosteroid, cytostatic, or anti-TNFα antibody or other antibody-based immunosuppressive therapy.

12. The method of claim 1, further comprising administering an immune-modulating therapy to the subject before or after determining the concentration of polycytotoxic T cells.

13. The method of claim 1, wherein the subject has an infection caused by an intracellular pathogen, an extracellular pathogen, a bacterial infection, a parasitic infection, a pathogenic strain of *E. coli*, leprosy, tuberculosis, Stevens-Johnson syndrome, toxic epidermal necrolysis, melanoma, or other cancer.

14. The method of claim 1, wherein the subject has undergone an organ transplant.

15. The method of claim 1, further comprising administering an allogeneic transplant or a xenogeneic transplant to the subject before or after determining the concentration of polycytotoxic T cells.

16. A composition comprising T cells, wherein at least 10% of the T cells are polycytotoxic T cells or at least 10% of the cells in the composition are polycytotoxic T cells.

17. A method of treating or preventing a disease or condition in a subject, comprising administering to the subject a composition comprising T cells, wherein at least 10% of the T cells are polycytotoxic T cells.

18. The method of claim 17, wherein the T cells are autologous or allogenic.

19. The method of claim 17, wherein the disease or condition is an infection caused by an intracellular pathogen, an extracellular pathogen, a bacterial infection, a parasitic infection, a pathogenic strain of *E. coli*, leprosy, tuberculosis, melanoma, or other cancer.

20. The method of claim 17, further comprising administering an immune-modulating therapy to the subject.

* * * * *